United States Patent
Oh et al.

(10) Patent No.: US 9,150,829 B2
(45) Date of Patent: Oct. 6, 2015

(54) CULTURE OF PLURIPOTENT AND MULTIPOTENT CELLS ON MICROCARRIERS

(75) Inventors: Steve Oh, Centros (SG); Allen Chen, Centros (SG); Andre Choo, Centros (SG); Shaul Reuveny, Centros (SG)

(73) Assignee: AGENCY FOR SCIENCE, TECHNOLOY AND RESEARCH, Singapore (SG)

( * ) Notice: Subject to any disclaimer, the term of this patent is extended or adjusted under 35 U.S.C. 154(b) by 144 days.

(21) Appl. No.: 13/257,674

(22) PCT Filed: Mar. 12, 2010

(86) PCT No.: PCT/SG2010/000091
§ 371 (c)(1),
(2), (4) Date: Sep. 20, 2011

(87) PCT Pub. No.: WO2010/107392
PCT Pub. Date: Sep. 23, 2010

(65) Prior Publication Data
US 2012/0009645 A1 Jan. 12, 2012

Related U.S. Application Data

(60) Provisional application No. 61/161,786, filed on Mar. 20, 2009.

(51) Int. Cl.
*C12N 5/071* (2010.01)
*C12N 5/00* (2006.01)
*C12N 5/0735* (2010.01)
*C12N 5/074* (2010.01)

(52) U.S. Cl.
CPC ............ *C12N 5/0606* (2013.01); *C12N 5/0696* (2013.01); *C12N 2501/727* (2013.01); *C12N 2531/00* (2013.01)

(58) Field of Classification Search
None
See application file for complete search history.

(56) References Cited

U.S. PATENT DOCUMENTS

| | | | |
|---|---|---|---|
| 5,858,747 A | 1/1999 | Schinstine et al. | |
| 6,387,369 B1 | 5/2002 | Pittenger et al. | |
| 2007/0010011 A1 | 1/2007 | Parsons et al. | |
| 2007/0204351 A1 | 8/2007 | Davidson et al. | |
| 2007/0264713 A1 | 11/2007 | Terstegge et al. | |
| 2008/0187494 A1 | 8/2008 | Davidson et al. | |
| 2009/0202498 A1 | 8/2009 | Davidson et al. | |
| 2010/0093053 A1 | 4/2010 | Oh et al. | |
| 2010/0124781 A1 | 5/2010 | Nelson | |
| 2011/0014693 A1 | 1/2011 | Oh et al. | |
| 2011/0111498 A1 | 5/2011 | Oh et al. | |
| 2011/0129919 A1 | 6/2011 | Oh et al. | |
| 2011/0143433 A1 | 6/2011 | Oh et al. | |

FOREIGN PATENT DOCUMENTS

| | | |
|---|---|---|
| WO | 03/029418 A2 | 4/2003 |
| WO | 2005/007799 A2 | 1/2005 |
| WO | 2006/091921 A2 | 8/2006 |
| WO | 2007/030469 A2 | 3/2007 |
| WO | 2007/030870 A1 | 3/2007 |
| WO | 2007/070964 A1 | 6/2007 |
| WO | 2007/149926 A1 | 12/2007 |
| WO | 2008/004990 A2 | 1/2008 |
| WO | 2008/005520 A2 | 1/2008 |
| WO | 2008/015682 A2 | 2/2008 |
| WO | 2008/035110 A1 | 3/2008 |
| WO | 2009/006422 A1 | 1/2009 |
| WO | 2009/139703 A1 | 11/2009 |
| WO | 2010/002846 A1 | 1/2010 |
| WO | 2010/059775 A1 | 5/2010 |

OTHER PUBLICATIONS

Mitalipova (2005, Nature Biotechnology. 23:19-20).*
Chen, A.K. et al., Expansion of Human Embryonic Stem Cells on Cellulose Microcarriers, Current Protocols in Stem Cell Biology, 14:1C.11.1-1C.11.14 (2010).
Chen, A.K. et al., Inhibition of ROCK-Myosin II Signaling Pathway Enables Culturing of Human Pluripotent Stem Cells on Microcarriers Without Extracellular Matrix Coating, Tissue Engineering: Part C, pp. 1-12 (2013).
Chen, X. et al., Investigations into the Metabolism of Two-Dimensional Colony and Suspended Microcarrier Cultures of Human Embryonic Stem Cells in Serum-Free Media, Stem Cells and Development, 19(11):1781-1792 (2010).
Mitalipova, M. et al., Human Embryonic Stem Cell Lines Derived from Discarded Embryos, Stem Cells, 21: 521-526 (2003).
Alexis Biochemicals, Product flyer—ROCK Inhibitors, www.axxora.com, Nov. 1, 2006.
Chen et al., "Critical microcarrier properties affecting the expansion of undifferentiated human embryonic stem cells", Stem Cell Research, 7:(2):97-111, 2011.
Choo et al., "Immortalized feeders for the scale-up of human embryonic stem cells in feeder and feeder-free conditions", Journal of Biotechnology, 122:130-141, 2006.
Claassen et al., "ROCK Inhibition Enhances the Recovery and Growth of Cryopreserved Human Embryonic Stem Cells and Human Induced Pluripotent Stem Cells", Molecular Reproduction & Development, pp. 1-11, 2009.
Fernandes et al., "Maintenance of pluripotency of human embryonic stem cells expanded in microcarrier-based stirred cultures", poster presented at a 21st ESACT meeting on Jun. 7-10, 2009 in Dublin, Ireland.

(Continued)

*Primary Examiner* — Valarie Bertoglio
(74) *Attorney, Agent, or Firm* — Choate, Hall & Stewart LLP; Charles E. Lyon

(57) ABSTRACT

A method is disclosed for culturing pluripotent or multipotent cells in vitro, the method comprising attaching pluripotent or multipotent cells to a plurality of microcarriers to form microcarrier-cell complexes, and culturing the microcarrier-cell complexes in suspension culture in the presence of a ROCK inhibitor.

18 Claims, 31 Drawing Sheets

(56) References Cited

OTHER PUBLICATIONS

Fernandes et al., "Mouse embryonic stem cell expansion in a microcarrier-based stirred culture system", Journal of Biotechnology, 132:227-236, 2007.
Fernandes et al., "Successful scale-up of human embryonic stem cell production in a stirred microcarrier culture system", Brazilian Journal of Medical and Biological Research, 42:515-522, 2009.
Fok et al., "Shear-controlled single-step mouse embryonic stem cell expansion and embryoid body-based differentiation", Stem Cells, 23:1333-1342, 2005.
Frauenschuh et al., "A Microcarrier-based Cultivation System for Expansion of Primary Mesenchymal Stem Cells", Biotechnol. Prog., 23:187-193, 2007.
Graichen et al., "Enhanced cardiomyogenesis of human embryonic stem cells by a small molecular inhibitor of p38 MAPK", Differentiation, pp. 1-14, 2007.
Harb et al., "The Rho-Rock-Myosin Signaling Axis Determines Cell-Cell Integrity of Self-Renewing Pluripotent Stem Cells", PLoS One, 3(8):1-13, 2008.
Hay et al., "Highly efficient differentiation of hESCs to functional hepatic endoderm requires ActivinA and Wnt3a signaling", PNAS, 105(34):12301-12306, 2008.
Ilic et al., "Derivation of human embryonic stem cell lines from biopsied blastomeres on human feeders with a minimal exposure to xenomaterials", Stem Cells Dev., 18(9):1343-1350, 2009.
Itskovitz-Eldor et al., "Differentiation of human embryonic stem cells into embryoid bodies comprising the three embryonic germ layers", Molecular Medicine, 6(2):88-95, 2000.
Jaenisch, R., "Celebrating 10 years of hESC Lines: An Interview with Rudolf Jaenisch", Stem Cells, 26(12):3005-3007, 2008.
Jo et al., "Fetal mesenchymal stem cells derived from human umbilical cord sustain primitive characteristics during extensive expansion", Cell Tissue Res., 334:423-433, 2008.
Kedong et al., "Simultaneous expansion and harvest of hematopoietic stem cells and mesenchymal stem cells derived from umbilical cord blood", J. Mater Sci.: Mater Med., 21:3183-3193, 2010.
Kehoe et al., "Scalable stirred-suspension bioreactor culture of human pluripotent stem cells", Tissue Eng. Part A., pp. 405-421, published online Oct. 17, 2009.
Kim et al., "Ex vivo characteristics of human amniotic membrane-derived stem cells", Cloning and Stem Cells, 9(4):581-594, 2007.
King et al., "Bioreactor development for stem cell expansion and controlled differentiation", Current Opinion in Chemical Biology, 11:394-398, 2007.
Krawetz et al., "Large-scale expansion of pluripotent human embryonic stem cells in stirred-suspension bioreactors", Tissue Eng. Part C, 16(4):573-582, published online Sep. 8, 2009.
Kroon et al., "Pancreatic endoderm derived from human embryonic stem cells generates glucose-responsive insulin-secreting cells in vivo", Nat Biotechnol., 26(4):443-452, 2008.
Lei et al., "Xeno-free derivation and culture of human embryonic stem cells: current status, problems and challenges", Cell Research, 17:682-688, 2007.
Li et al., "ROCK inhibitor improves survival of cryopreserved serum/feeder-free single human embryonic stem cells", Human Reproduction, 24(3):580-589, 2009.
Lian et al., "Derivation of Clinically Compliant MSCs from CD105+, CD24-Differentiated Human ESCs", Stem Cells, 25:425-436, 2007.
Lock et al., "Expansion and Differentiation of Human Embryonic Stem Cells to Endoderm Progeny in a Microcarrier Stirred-Suspension Culture", Tissue Engineering: Part A, 15:2051-2063, published online Jan. 13, 2009.
Lu et al., "Defined culture conditions of human embryonic stem cells", PNAS, 103(15):5688-5693, 2006.
Martin-Ibanez et al., "Novel Cryopreservation method for dissociated human embryonic stem cells in the presence of a ROCK inhibitor", Human Reproduction, 23(12):2744-2754, 2008.
Merck leaflet, "(R)-(+)-trans-N-(4-pyridyl)-4-(1-aminoethyl)-cyclohexanecarboxamide, 2HCI ROCK inhibitor", Calbiochem, downloaded Mar. 17, 2009.
Newman et al., "Poly(D,L lactic-co-glycolic acid) microspheres as biodegradable microcarriers for pluripotent stem cells", Biomaterials, 25:5763-5771, 2004.
Nie et al., "Scalable Culture and Cryopreservation of Human Embryonic Stem Cells on Microcarriers", Biotechnol. Prog., 25:20-31, 2009.
Niebruegge et al., "Generation of human embryonic stem cell-derived mesoderm and cardiac cells using size-specified aggregates in an oxygen-controlled bioreactor", Biotechnology and Bioengineering, 102(2):493-507, 2009.
Oh et al., "Human Embryonic Stem Cell Technology: Large Scale Cell Amplification and Differentiation", Cytotechnology, 50:181-190, 2006.
Oh et al., "Advances and perspectives in human and mouse embryonic stem cell bioprocessing", Drug Discovery Today: Technologies, pp. 1-6, 2008.
Oh et al., "Long term microcarrier suspension cultures of human embryonic stem cells", Stem Cell Research, 2(3):219-230, 2009.
Michael F. Olson, Applications for ROCK kinase inhibition, Current Opinion in Cell Biology, 20:242-248, 2008.
Pereira et al., "Reproducible methodology for the isolation of mesenchymal stem cells from human umbilical cord and its potential for cardiomyocyte generation", J. Tissue Eng. Regen. Med., 2:394-399, 2008.
Phillips et al., "Efficient expansion of clinical-grade human fibroblasts on microcarriers: cells suitable for ex vivo expansion of clinical-grade hESCs", Journal of Biotechnology, 134:79-87, 2008.
Phillips et al., "Attachment and growth of human embryonic stem cells on microcarriers", Journal of Biotechnology, 138:24-32, 2008.
Sart et al.,"Influence of culture parameters on ear mesenchymal stem cells expanded on microcarriers", Journal of Biotechnology, 150:149-160, 2010.
Schop et al., "Expansion of mesenchymal stem cells using a microcarrier-based cultivation system: growth and metabolism", J. Tissue Eng. Regen. Med., 2:126-135, 2008.
Sun et al., "Cell proliferation of human bone marrow mesenchymal stem cells on biodegradable microcarriers enhances in vitro differentiation potential,", Cell Prolif., 43:445-456, 2010.
Troyer et al., "Concise Review: Wharton's Jelly-Derived Cells Are a Primitive Stromal Cell Population", Stem Cells, 26:591-599, 2008.
Watanabe et al., "A ROCK inhibitor permits survival of dissociated human embryonic stem cells", Nature Biotechnology, 25(6):681-686, 2007.
Shinya Yamanaka, "Strategies and New Developments in the Generation of Patient-Specific Pluripotent Stem Cells", Cell Stem Cell, 1:39-49, 2007.
Yang et al., "Ev vivo expansion of rat bone marrow mesenchymal stromal cells on microcarrier beads in spin culture", Biomaterials, 28:3110-3120, 2007.
Yang et al., "Suspension Culture of Mammalian Cells Using Thermosensitive Microcarrier That Allows Cell Detachment Without Proteolytic Enzyme Treatment", Cell Transplantation, 19:1123-1132, 2010.

\* cited by examiner

Cytodex 1 + ROCK P5

DE53+Matrigel P5

DE53+ROCK P5

CULTURE OF PLURIPOTENT AND MULTIPOTENT CELLS ON MICROCARRIERS

FIELD OF THE INVENTION

The present invention relates to the culture of pluripotent and multipotent cells on microcarriers in the presence of a ROCK inhibitor.

BACKGROUND TO THE INVENTION

Stem cells, unlike differentiated cells have the capacity to divide and either self-renew or differentiate into phenotypically and functionally different daughter cells (Keller, Genes Dev. 2005; 19:1129-1155; Wobus and Boheler, Physiol Rev. 2005; 85:635-678; Wiles, Methods in Enzymology. 1993; 225:900-918; Choi et al, Methods Mol. Med. 2005; 105:359-368).

Human embryonic stem cells (hESC) are pluripotent cells with the capability of differentiating into a variety of stem cell types. The pluripotency of stem cells such as embryonic stem cells (ESCs) and their ability to differentiate into cells from all three germ layers makes these an ideal source of cells for regenerative therapy for many diseases and tissue injuries (Keller, Genes Dev. 2005; 19:1129-1155; Wobus and Boheler, Physiol Rev. 2005; 85:635-678).

Expansion of stem cells to large quantities, requiring one or more passages, is a pre-requisite for cell therapy.

Currently, stem cells (including human embryonic stem cells, hESC) which grow as colonies are routinely maintained on plastic culture surfaces in 2 dimensional (2D) growth. Expansion to larger quantities on 2D culture would necessitate the use of large surface areas. The manual nature of passaging the cells by repeated pipetting or enzymatic treatment to break up these 2D colonies to smaller sizes would become impractical. Preparing numerous plates for seeding large surface areas can become subject to handling errors. Furthermore, very large surface areas such as Nunc trays for example, would be needed.

Accordingly, the current methods of growing stem cells as 2D colony cultures on coated plastic surfaces are not amenable to scale up and the experimental conditions under which culture is carried out is generally not amenable to good control. The prior art includes a number of attempts to culture stem cells in a 3 dimensional ("3D") environment, such as on microcarriers in suspension culture. Except for a few studies of mouse embryonic stem cells on microcarriers (Fernandes et al., 2007; Abranches et al., 2007; King and Miller, 2007) and differentiating hESC in suspension culture as embryoid bodies (Dang et al., 2004; Fok and Zandstra, 2005; Cameron et al., 2006), there is no robust method of long term, serial culturing of hESC in suspension culture.

It is known in the art for embryonic stem cells to be differentiated as "embryoid bodies" in suspension culture. Such embryoid bodies comprise a mass of already differentiated cells. For example, Gerecht Nir et al (2004) described the use of a rotating-wall bioreactor to culture embryoid bodies. Embryoid body culture was also shown using agitation systems by Zandstra et al (2003), Dang et al (2004) and Wartenberg et al (1998). Embryoid body suspension culture has also been reported by Dang and Zandstra (2005) and King and Miller (2007). Such techniques are suitable for culturing these tissue-like embryoid body aggregates comprising differentiated stem cells, but not for undifferentiated stem cells.

Fok and Zandstra (2005) described stirred-suspension culture systems for the propagation of undifferentiated mouse embryonic stem cells (mESCs). The stirred-suspension culture systems comprised microcarrier and aggregate cultures. Mouse embryonic stem cells cultured on glass microcarriers had population doubling times comparable to tissue-culture flask controls. Upon removal of leukemia inhibitory factor, the mESC aggregates developed into embryoid bodies (EBs) capable of multilineage differentiation. Suspension cultures of mouse ESCs are also described in King and Miller (2005). However, King and Miller (2005) state that "expansion of undifferentiated human ESCs (hESCs) is more difficult than for mESCs and has not yet been reported in stirred cultures".

US2007/0264713 (Terstegge) discloses an attempt at culturing human embryonic stem cells on microcarriers. Human embryonic stem cells are introduced together with Cytodex3 (Amersham) microcarriers into a spinner or a bioreactor together with conditioned medium in various volumes. The culture is agitated at 20-30 rpm 30 minutes in an hour. The culture is maintained for various times between 10 days and 6 weeks. However, at no time were any of the cultures passaged or sub-cultured, which is an essential requirement for large scale continuous production of stem cells. Demonstration of continuous passaging and the ability to sub-culture along with 'good' (exponential) growth rate on microcarriers are essential requirements for large-scale production of stem cells. This was not demonstrated by the work of Terstegge et al.

WO2008/004990 describes attempts to culture stem cells in the absence of feeder cells and contemplates the use of microcarriers. It is concerned with cultures in which Matrigel is not used. WO2008/004990 describes the effect of positively charged surfaces in the inhibition of stem cell differentiation.

In Phillips et al., 2008 (Journal of Biotechnology 138 (2008) 24-32) an attempt to culture hESC on microcarriers by seeding aggregates as well as single cells is reported. Initially, 3-fold expansion was achieved over 5 days, however with each successive passage cell expansion was reduced until cells could not be passaged beyond week 6.

Previous attempts to use commercially available microcarriers such as Cytodex 1 and 3 for scale up culture of human embryonic stem cells (hESCs) were unsuccessful. The hESC cultures died or differentiated on the carriers and could not be propagated (Oh & Choo, 2006).

The ROCK Inhibitor Y-27632 has been proposed by Watanabe et at and Harb et at as a factor capable of permitting the survival of dissociated human embryonic stem cells in 2D culture (Watanabe et al. A ROCK inhibitor permits survival of dissociated human embryonic stem cells. Nature Biotechnology Vol. 25 No. 6 p 681-686 June 2007. WO 2008/035110. Harb et al. The Rho-Rock-Myosin Signaling Axis Determines Cell-Cell Integrity of Self-Renewing Pluripotent Stem Cells. PLoS ONE 3(8): e3001. doi:10:1371

ROCK Inhibitor has also been investigated as an agent that may improve cryopreservation of human embryonic stem cells (Xiangyun Li et al. ROCK inhibitor improves survival of cryopreserved serum/feeder-free single human embryonic stem cells. Human Reproduction, Vol. 24, No. 3 pp. 580-589, 2009. Martin-Ibanez et al. Novel cryopreservation method for dissociated human embryonic stem cells in the presence of a ROCK inhibitor. Human Reproduction. Vol. 23. No. 12 pp. 2744-2754, 2008. Claassen et al. ROCK Inhibition Enhances the Recovery and Growth of Cryopreserved Human Embryonic Stem Cells and Human Induced Pluripotent Stem Cells. Molecular Reproduction & Development 2009). However, in every case it is indicated for use in the context of 2D culture of human embryonic stem cells on Matrigel.

Using microcarriers coated in Matrigel we previously achieved stable and continuous growth in suspension of undifferentiated, pluripotent cells from primates, including human embryonic stem cells and human induced pluripotent cells, through successive passages (partially reported in Oh et al 2009 and further described in U.S. patent applications U.S. 61/069,694 filed 17 Mar. 2009, U.S. 61/110,256 filed 31 Oct. 2008, U.S. 61/148,064 filed 29 Jan. 2009 and U.S. 61/155, 940 filed 27 Feb. 2009). However, so far, this result has not been obtained using microcarriers that do not have a surface coating of an extracellular matrix derived material.

Since then, Lock et al have described growth of hESCs on Matrigel coated microcarriers, but without passage (Lock et al. expansion and Differentiation of Human Embyronic Stem Cells to Endoderm Progeny in a Microcarrier Stirred-Suspension Culture. Tissue Engineering: Part A Vol. 15, No. 00, 2009) and Nie et al investigated growth of hESCs on microcarriers having a matrix coating or feeder cell layer (Nie et al. Scalable Culture and Cryopreservation of Human Embyronic Stem Cells on Microcarriers. Biotechnol. Prog., 2009, Vol. 25, No. 1).

SUMMARY OF THE INVENTION

The inventors have now found that pluripotent stem cells can be successfully cultured and passaged in the presence of a ROCK Inhibitor on microcarriers that do not have a matrix coating, whilst maintaining the pluripotent status of the cultured and passaged cells.

The present invention provides a method for the stable and long term culturing of pluripotent and mulitpotent cells in in vitro culture in the presence of a ROCK Inhibitor.

Using this method human embryonic stem cells have been expanded and passaged, and the pluripotency of the expanded and passaged human embryonic stem cell population has been maintained beyond at least passage 9.

Accordingly, one aspect of the present invention relates to the growth and proliferation of pluripotent or multipotent cells on microcarriers in suspension culture. The method may involve culture through one or a plurality of passages whilst retaining the respective pluripotent or multipotent status of cells in the culture. The culture is conducted in the presence of a ROCK Inhibitor which may be added to the culture media as a culture supplement or additive.

By including a ROCK Inhibitor in the culture the inventors have found that it is not necessary to coat the surface of the microcarriers in a matrix, e.g. an extracellular matrix material. Until now, this has been considered an essential requirement to maintain the pluripotent or multipotent status of suspension microcarrier-cultured pluripotent or multipotent cells, particularly of human or primate embryonic stem cells and human or primate induced pluripotent cells.

Microcarriers are seeded with the pluripotent or multipotent cells. The microcarrier-cell complexes are then cultured in suspension culture, preferably to expand the number of pluripotent or multipotent cells in the culture. Cultured cells may be passaged, and passaged cells may also be seeded on microcarriers, e.g. for further culture or for differentiation.

In this way pluripotent or multipotent cells can be taken through a plurality of passages, e.g. at least 2 passages, with the cultured and passaged cells retaining the respective pluripotent or multipotent status. Using this method proliferation of pluripotent or multipotent cells is seen during each cycle of culture between passages and can be maintained over many (at least 9) passages.

This culture method permits the continuous growth and passaging of pluripotent or multipotent cells in in vitro culture thereby providing a method for expanding pluripotent or multipotent cells to therapeutically useful numbers.

Although continuous passage of pluripotent or multipotent cells on microcarriers will often be preferred, as part of the method of the present invention the pluripotent or multipotent cells may be transferred from culture on microcarriers to other culture systems, e.g. 2D colony culture, followed by return to suspension microcarrier culture.

In some embodiments the microcarriers are coated in a matrix, preferably having an extracellular component. In some embodiments the microcarriers are positively charged. The method preferably involves the steps of attachment of pluripotent or multipotent cells to microcarriers during each cycle of culture prior to passage. It is permissible for some cycles of culture to be undertaken on non-coated microcarriers and others on matrix coated microcarriers.

Although continuous passage of pluripotent or multipotent cells on microcarriers will often be preferred, as part of the method of the present invention the cultured cells may be transferred from culture on microcarriers to other culture systems, e.g. 2D colony culture, followed by return to suspension microcarrier culture.

A further aspect of the present invention relates to the differentiation of pluripotent or multipotent cells attached to microcarriers in suspension culture in the presence of a ROCK Inhibitor.

In some embodiments pluripotent or multipotent cells may be grown to a required cell density for differentiation by employing the microcarrier culture method described above. Once the required cell density is obtained the culture conditions may be changed to induce the differentiation of pluripotent or multipotent cells attached to the microcarriers. For differentiation the same or different microcarriers may be used compared with those used for growth of the pluripotent or multipotent cells. Similarly, where a matrix coating is used, the same or different matrix coating may be used. For example, a first microcarrier having a first coating may be used for the growth and proliferation of pluripotent or multipotent cells and a second microcarrier having a second coating may be used for the differentiation of those cells. The second microcarrier may be uncoated or may be surface coated in a matrix.

The use of microcarrier culture for both proliferation of pluripotent or multipotent cells and for their differentiation has the advantages of avoiding the need to re-seed the differentiation culture, of the proliferation culture providing a high number of pluripotent or multipotent cells for differentiation and the convenience of changing from proliferation to differentiation by changing the culture conditions.

In other embodiments pluripotent or multipotent cells for differentiation may be grown to a required cell density by other culture methods, for example by 2D colony culture. Those cells are then attached to microcarriers and cultured in suspension culture in the presence of a ROCK Inhibitor under conditions that induce the differentiation of the pluripotent or multipotent cells.

In some embodiments pluripotent or multipotent cells that have already undergone differentiation (but preferably not terminal differentiation) may be attached to microcarriers and cultured in suspension culture in the presence of a ROCK Inhibitor under conditions that induce the differentiation of the cells.

In the methods of the present invention the ROCK Inhibitor is preferably allowed to contact the cells being cultured or differentiated. The ROCK Inhibitor is also preferably allowed to contact the microcarriers to which the cells are attached, or are to be attached to. To allow such contact liquid, fluid, gel or other flowable culture media are preferred.

In one aspect of the present invention a method of culturing pluripotent or multipotent cells in vitro is provided, the method comprising:
(i) attaching pluripotent or multipotent cells to a plurality of microcarriers to form microcarrier-cell complexes, and
(ii) culturing the microcarrier-cell complexes in suspension culture in the presence of a ROCK inhibitor.

In some embodiments the method further comprises passaging the cultured cells from (ii), wherein cells after passaging are pluripotent or multipotent.

In some embodiments the method further comprises:
(iii) passaging the cultured cells from (ii); and
(iv) repeating steps (i)-(iii) through at least 2 passages,
wherein cells in the culture after step (iv) are pluripotent or multipotent. In some embodiments, in each repeat cycle the stem cells of step (i) are obtained from the passaged cells of step (iii) of the preceding repeat cycle.

In step (iv), steps (i)-(iii) may be repeated through one of: at least 3 passages, at least 4 passages, at least 5 passages, at least 6 passages, at least 7 passages, at least 8 passages, at least 9 passages, at least 10 passages, at least 11 passages, at least 12 passages, at least 13 passages, at least 14 passages, at least 15 passages, at least 16 passages, at least 17 passages, at least 18 passages, at least 19 passages, at least 20 passages, at least 21 passages, at least 22 passages, at least 23 passages, at least 24 passages, at least 25 passages, at least 30 passages, at least 40 passages, at least 50 passages, at least 60 passages, at least 70 passages, at least 80 passages, at least 90 passages, at least 100 passages.

In some embodiments, in step (ii) the cells are cultured for a period of time sufficient to expand the number of cells in the culture. In some embodiments, after step (iv) at least 60% of the cells in the culture are pluripotent or multipotent. In some embodiments, after step (iv) at least 60% of the cells in the culture express one, two, three or all of Oct4, SSEA4, TRA-1-60 and Mab84.

In some embodiments the propagated cells preferably retain at least one biological activity of pluripotent or multipotent cells after the stated number of passages. The biological activity may be chosen from the group consisting of: (i) expression of a pluripotency marker, (ii) cell viability; (iii) normal karyotype, (iv) ability to differentiate into endoderm, ectoderm or mesoderm. The biological activity may comprise expression of a pluripotency marker chosen from the group consisting of: OCT-4, SSEA-4, TRA-1-60 and Mab84.

In some embodiments the method comprises culturing the cells in serum free media, or stem cell conditioned media, or feeder cell free conditions. Feeder cell free conditions may include the absence of feeder cells coated on microcarriers present in the suspension culture and/or the complete absence of feeder cells from the suspension culture.

In some embodiments feeder cells are also attached to the microcarriers. In some embodiments the culture further comprises feeder cells attached to microcarriers which are different to the microcarriers to which the pluripotent or multipotent cells are attached.

Methods according to the present invention may comprise passaging into or from an alternative culture system, e.g. a 2D culture. Cells may be stored, e.g. frozen and thawed, in order to facilitate transfer between the culture systems.

In some embodiments the pluripotent or multipotent cells may be cultured on other particles/surfaces for a limited period of time. For example, pluripotent or multipotent cells from step (ii) or (iii) may be cultured in an alternative culture system (e.g. on 2D culture) for a limited number of passages (e.g. less than 5, more preferably less than 3, more preferably 1) before being returned to culture on microcarriers in the presence of a ROCK Inhibitor.

In other embodiments pluripotent or multipotent cells may be removed from the culture method and stored (e.g. as frozen cells) before being returned to suspension culture in accordance with the present invention. Cells may be stored (e.g. frozen) in the presence of a ROCK Inhibitor.

In such embodiments return to suspension culture in accordance with the present invention does not require a return to the same culture. The suspension culture according to the present invention may even be continued in a different geographical location, e.g. following freezing and transport of cells.

Methods according to the present invention may further comprise the step of separating the human embryonic stem cells from the microcarriers.

In some embodiments the method comprises the step of inducing differentiation of the pluripotent or multipotent cells obtained from the culture. Accordingly, in some embodiments the method comprises placing the microcarrier-cell complexes under conditions which induce the differentiation of the cells.

In some embodiments the method comprises the step of separating the pluripotent or multipotent cells obtained from the culture method from the microcarriers and culturing the separated cells in non-microcarrier culture under conditions which induce differentiation of the cells.

In some embodiments the method further comprises the in vitro differentiation of the pluripotent or multipotent cells obtained from the culture method, comprising:
(a) attaching pluripotent or multipotent cells obtained from the culture method to a plurality of second microcarriers to form microcarrier-cell complexes,
(b) culturing the microcarrier-cell complexes from (a) in suspension culture under conditions that induce the differentiation of the cells.

The method may further comprise:
(c) attaching differentiated cells obtained from step (b) to a plurality of third microcarriers to form microcarrier-cell complexes; and
(d) culturing the microcarrier-cell complexes from (c) in suspension culture under conditions that induce the further differentiation of the already differentiated cells.

In some embodiments the culture conditions for differentiation comprise culturing the cells in the presence of a ROCK inhibitor.

In other embodiments the culture conditions for differentiation comprise culturing the cells in the absence of a ROCK inhibitor.

Pluripotent or multipotent cell(s) obtained by the methods of the invention are provided. Differentiated cell(s) obtained by the methods of the invention are also provided. In some embodiments differentiated cells obtained by the methods of the invention are cultured to form an embryoid body. Accordingly, an embryoid body so obtained is also provided.

In one aspect of the present invention a method of differentiating pluripotent or multipotent cells in vitro is provided, the method comprising attaching pluripotent or multipotent cells to a plurality of microcarriers to form microcarrier-cell complexes, wherein the surface of the microcarriers is uncoated or is coated in a matrix, and culturing the microcarrier-cell complexes in suspension culture in the presence of a ROCK inhibitor and under conditions that induce the differentiation of the cells.

In another aspect of the present invention a suspension culture of pluripotent or multipotent cells is provided, wherein the cells are attached to a plurality of microcarriers thereby forming microcarrier-cell complexes and the suspension culture media contains a ROCK inhibitor.

In some embodiments a container, e.g. a bioreactor, or device for propagating pluripotent or multipotent cells comprising the suspension culture is provided. The suspension culture may be a spinner suspension culture.

In some embodiments the ROCK inhibitor is present in the culture media at a concentration of one of: at least 1 µM, at least 2 µM, at least 3 µM, at least 4 µM, at least 5 µM, at least 6 µM, at least 7 µM, at least 8 µM, at least 9 µM, at least 10 µM, at least 15 µM, at least 20 µM, at least 30 µM, at least 40 µM, or at least 50 µM. The ROCK inhibitor may optionally be present in the culture media at a concentration of less than one of: 100 µM, 90 µM, 80 µM, 70 µM, or 60 µM.

In a further aspect of the present invention the use of a ROCK inhibitor in the in vitro suspension culture of pluripotent or multipotent cells is provided, wherein the cells are in the form of microcarrier-cell complexes.

In yet another aspect of the present invention the use of a ROCK inhibitor in the differentiation of pluripotent or multipotent cells in suspension culture in vitro is provided, wherein the cells are in the form of microcarrier-cell complexes.

In a further aspect of the present invention a method of propagating pluripotent or multipotent cells is provided, the method comprising the steps of:
(a) providing a microcarrier;
(b) allowing a pluripotent or multipotent cell to attach to the microcarrier; and
(c) aggregating microcarriers with pluripotent or multipotent cells attached thereon to thereby propagate the pluripotent or multipotent cells,
wherein in one or more, or all, of steps (a), (b) or (c) the microcarrier and/or cells are contacted with a ROCK Inhibitor.

In another aspect of the present invention a method of propagating pluripotent or multipotent cells is provided, the method comprising:
(a) providing a first pluripotent or multipotent cell attached to a first microcarrier;
(b) providing a second pluripotent or multipotent cell attached to a second microcarrier;
(c) allowing the first pluripotent or multipotent cell to contact the second pluripotent or multipotent cell to form an aggregate of cells; and
(d) culturing the aggregate in the presence of a ROCK Inhibitor to propagate the pluripotent or multipotent cells for at least one passage.

In yet another aspect of the present invention, a method of propagating pluripotent or multipotent cells is provided, the method comprising the steps of:
(a) providing a first microcarrier with a pluripotent or multipotent cell attached thereto;
(b) allowing the first microcarrier to contact a second microcarrier comprising a second pluripotent or multipotent cell attached thereto to form an aggregate; and
(c) culturing the aggregate in the presence of a ROCK Inhibitor.

In another aspect of the present invention, a method of propagating pluripotent or multipotent cells is provided, the method comprising the steps of:
(a) providing a plurality of microcarriers with pluripotent or multipotent cells attached thereto;
(b) aggregating the plurality of microcarriers to form an aggregate; and
(c) culturing the aggregate in the presence of a ROCK Inhibitor.

In the aspects and embodiments described the ROCK inhibitor is preferably chosen from: Y-27632, HA-1077 (Fasudil), HA-1100 (HydroxyFasudil), H-1152, 3-(4-Pyridyl)-1H-indole, N-(4-Pyridyl)-N'-(2,4,6-trichlorophenyl) urea, Aurothioglucose, LY294002 or a salt, base, ester or prodrug thereof.

In preferred embodiments the microcarriers do not have a matrix coating.

In other embodiments the surface of the microcarriers may be coated in a matrix. The matrix may comprise an extracellular matrix component and may be one or more of Matrigel™ (BD Biosciences), hyaluronic acid, laminin, fibronectin, vitronectin, collagen, elastin, heparan sulphate, dextran, dextran sulphate, chondroitin sulphate. The matrix may comprise a mixture of laminin, collagen I, heparan sulfate proteoglycans, and entactin 1.

In some embodiments the pluripotent or multipotent cells are stem cells, and may be embryonic stem cells, induced pluripotent stem cells or adult stem cells. The cells may be mammalian (e.g. rabbit, guinea pig, rat, mouse or other rodent (including cells from any animal in the order Rodentia), cat, dog, pig, sheep, goat, cattle, horse, non-human mammal, non-human primate), primate or human.

In the aspects and embodiments described the microcarriers may comprise or consist of one or more of cellulose, dextran, hydroxylated methacrylate, collagen, gelatin, polystyrene, plastic, glass, ceramic, silicone. Alternatively, the microcarriers may be macroporous or microporous carboseed microcarriers.

In some embodiments the microcarriers are coupled with protamine or polylysine. In some embodiments the microcarriers are positively charged. In some embodiments the microcarriers have a positive surface charge. In some embodiments the microcarriers are hydrophilic. In some embodiments the microcarriers are rod-shaped. In other embodiments the microcarriers have a substantially spherical shape.

Methods according to the present invention may comprise continuous or intermittent agitation of the cell culture, e.g. from about 5 to about 200 rpm, about 5 to about 150 rpm, about 5 to about 100 rpm, about 30 rpm or more or about 50 rpm or more, or about 100 rpm or more. Alternatively the methods may comprise static culture.

In some embodiments an increase in the rate or amount of agitation may be used to induce differentiation of cells, whereas a lower rate or amount of agitation may be used to expand pluripotent or multipotent cell populations without inducing significant differentiation.

To culture pluripotent or multipotent cell populations without inducing significant differentiation, cultures may be agitated at from about 5 rpm to about 100 rpm, from about 5 rpm to about 50 rpm, from about 5 rpm to about 40 rpm, from about 5 rpm to about 30 rpm, from about 5 rpm to about 25 rpm, from about 5 rpm to about 20 rpm, from about 5 rpm to about 15 rpm, from about 5 rpm to about 10 rpm.

For the induction of significant differentiation, cultures may be agitated at from about 25 rpm to about 200 rpm or more, e.g. from about 30 rpm to about 200 rpm or more, from about 35 rpm to about 200 rpm or more, from about 40 rpm to about 200 rpm or more, from about 45 rpm to about 200 rpm or more, from about 50 rpm to about 200 rpm or more, from about 75 rpm to about 200 rpm or more, from about 100 rpm to about 200 rpm or more.

Significant differentiation of cells may include the situation where at least about 10% of cells in the culture differentiate. Alternatively, this may be where at least one of about 15%, 20%, 25%, 30%, 35%, 40%, 45% or 50% of cells in the culture differentiate.

Accordingly, methods of the invention may comprise conducting a first part of the method at a first rate or amount of agitation in order to culture cells whilst maintaining their pluripotent or multipotent status followed by a second part in which cells are cultured at a second rate or amount of agitation in order to allow cells in the culture to differentiate. The first rate or amount is preferably less than the second rate or amount. The first part of the method may therefore expand the population of pluripotent or multipotent cells and the second part of the method may begin the process of differentiation of some or all of those cells towards the endoderm, ectoderm or mesoderm lineage.

In a further aspect of the present invention a method of treating a disease in an individual in need of treatment is provided, the method comprising propagating a pluripotent or multipotent cell according to the methods described herein, producing a differentiated cell or embryoid body and administering the pluripotent or multipotent stem cell, differentiated cell or embryoid body into the individual.

DESCRIPTION OF PREFERRED EMBODIMENTS

The details of one or more embodiments of the invention are set forth in the accompanying description below including specific details of the best mode contemplated by the inventors for carrying out the invention, by way of example. It will be apparent to one skilled in the art that the present invention may be practiced without limitation to these specific details.

SUMMARY OF RESULTS

We have developed a method of culturing hESC on microcarriers in the absence of a matrix coating, e.g. Matrigel, for more than 5 consecutive passages using a variety of microcarriers (DE53, QA52, Tosoh, Cytodex 1, Cytodex 3) in the presence of a ROCK inhibitor supplement (e.g. Y27632, HA1077 (Fasudil) or Auriothioglucose). hESC retained their growth, final cell densities, expression of the pluripotent markers Oct4, Mab 84, and TRA-1-60, and normal karyotypes after 5 or more passages.

This improves on our earlier work on the use of microcarriers to culture pluripotent and multipotent cells using a range of microcarrier coatings (partially reported in Oh et al 2009 and further described in US patent applications U.S. 61/069,694 filed 17 Mar. 2009, U.S. 61/110,256 filed 31 Oct. 2008, U.S. 61/148,064 filed 29 Jan. 2009 and U.S. 61/155,940 filed 27 Feb. 2009, all incorporated herein by reference).

The present method is particularly promising as it avoids the need to coat the microcarriers in Matrigel, an animal derived matrix, or in other extracellular matrix components, to achieve expansion and differentiation of pluripotent hESC. This will assist in developing GMP compliant methods of expanding and differentiating hESC, as well as other pluripotent and multipotent cells, for use in research, therapeutic and diagnostic applications.

In particular, we have demonstrated:
1. Long term culture of hESC on cellulose DE53 microcarriers for 9 weeks (9 passages) using the ROCK inhibitor Y-27632 (FIG. 1).
2. Long term culture of hESC on spherical Tosoh microcarriers for 6 weeks (6 passages) with ROCK inhibitor Y-27632 (FIG. 4).
3. Comparison of long term culture of hESC on cellulose DE53, Tosoh, Cytodex1 and Cytodex 3 microcarriers for 5 weeks (5 passages) with ROCK inhibitor Y-27632 (FIG. 5).
4. Normal karyotypes of hESC on cellulose DE53, QA52, Tosoh, and Cytodex 3 microcarriers between 5 to 10 weeks with ROCK inhibitor Y-27632 (FIGS. 10 and 11).
5. Culture of hESC on cellulose DE53 microcarriers for 2 weeks with alternative ROCK inhibitors, HA1077 (Fasudil) and Aurothioglucose (FIGS. 12-14).

Suspension Culture and Passage of Stem Cells

We have previously demonstrated that it is possible to culture, propagate and passage primate and human stem cells and iPS cells on particles having a matrix coating. In particular, we have shown that stem cells may be grown continuously on matrix-coated microcarriers in suspension culture and passaged.

We now describe a method of propagating stem cells in suspension in the presence of a ROCK inhibitor. The method of propagating may comprise growing, propagating, proliferating, culturing, expanding or increasing stem cells. The propagating stem cells are able to be passaged for one or more passages, as described below. Such propagation may be achieved through the use of microcarriers or particles with certain properties. The microcarriers or particles may comprise a charge. The microcarriers or particles may optionally comprise a coating. A further property may comprise size.

The method of propagating stem cells may comprise the steps of providing particles. The particles may be uncoated or may comprise a matrix coated thereon. They may have a positive charge. The particles may have a size to allow aggregation of primate or human stem cells attached thereto. Stem cells are allowed to attach to the particle. The cells growing on different particles are allowed to contact each other and to form aggregates. The culture is passaged for at least one passage. The stem cells may be used attached to the carriers or detached or separated from them. They may be used in an undifferentiated or pluripotent state or both, or may be differentiated into a desired cell type. They may be used to form embryoid bodies.

In order for the particles to support continuous growth, they should have a size which is compatible with the dimensions of a primate or human stem cell, such as 10 µm, 20 µm, 30 µm, 40 µm, 50 µm, 60 µm, 70 µm, 80 µm, 90 µm, 100 µm, 110 µm, 120 µm, 130 µm, 140 µm, 150 µm, 160 µm, 170 µm, 180 µm, 190 µm, 200 µm, 210 µm, 220 µm, 230 µm, 240 µm, 250 µm or so. Culture of primate or human stem cells on such a particle with this order of size will enable cells growing thereon to aggregate with each other and support continuous growth. Suitable compositions, shapes and sizes of particles are described in further detail below.

The Examples show that stem cell cultures such as human embryonic stem cell 2D colony cultures may be inoculated onto microcarrier particles and grown in the presence of ROCK inhibitor for several generations with one or more passages. The stem cells may be passaged by dislodging from the surface by any means such as mechanical or enzymatic dissociation, or combination of both methods.

The microcarrier particle cultures may be grown from generation to generation on particles. Alternatively, or in addition, the cultures may be grown on conventional 2D cultures for one or more generations in between. Human stem cells growing on microcarriers may be transferred back to 2D colony cultures and vice versa.

The methods described here make available methods for efficient propagation of stem cells in undifferentiated form. The microcarrier cultures may be passaged onto microcarriers by mechanical or enzymatic dissociation with a splitting ratio of between 1 to 2 and 1 to 10, which is higher than possible for conventional 2D cultures. This enables more efficient utilisation of biomaterial with more rapid scale up of culture.

Volumetric yields of cells in microcarrier cultures are routinely 2 to 4 times more than 2D colony controls. The volumetric yield of human stem cells propagated by the methods described here may be up to 2 million cells/ml or more.

The methods described here enable the passaging of human stem cells from particles to particles for 9 passages or more, as described in further detail below.

The methods described here enable the propagation of stem cells that retain their pluripotent character. The Examples show that human embryonic stem cells propagated according to the methods and compositions described here are able to maintain one or more biological characteristics of stem cells. Thus, the propagated stem cells show expression of pluripotent markers, Oct-4, Tra-1-60 and mAb 84 for 5 or more passages equivalent to stem cells grown as 2D colony cultures, retain a normal karyotype.

Significantly, by anchoring stem cells on microcarriers, it is possible to serially passage the cells in larger scale spinner flasks.

Any stem cells may be propagated using the methods described here. These may comprise primate stem cells, such as monkey, ape or human stem cells. The stem cells may comprise embryonic stem cells or adult stem cells. The stem cells may comprise induced pluripotent stem cells. For example, the stem cells may comprise human embryonic stem cells (hESCs). These and other stem cells suitable for use in the methods and compositions described here are described in further detail below. The methods and compositions described here have various advantages over known "2D" culture methods. The particles are more efficient in attaching stem cells than 2D colony culture substrates. For this and other reasons, the suspension cultured cells are able to be passaged more effectively. The methods described here enable the stem cells to be frozen and thawed through several cycles. They may be frozen directly on the microcarriers and thawed onto growing medium (whether traditional plate culture, or on particulate microcarriers). The stem cells propagated on microcarriers may be grown in serum free media, which is GMP compliant.

The methods described here essentially enable the culture and maintenance of stem cells such as embryonic stem cells in an undifferentiated state. The propagated stem cells may be differentiated partially or totally, in culture (e.g., on microcarriers) or detached therefrom.

The propagated stem cells may be used to form embryoid bodies for further use. Stem cells growing on microcarriers may simply be transferred to differentiation medium to form embryoid bodies directly, in contrast with prior methods, which require an additional step of removing cells from a 2D growing surface prior to embryoid body formation.

Accordingly, the methods and compositions described here enable directed differentiation of stem cells on the growing surface or substrate without removal therefrom.

The methods and compositions described here enable expansion and scale up of cultured stem cells to larger volumes. The scale up to bioreactor or industrial scale enables more productive culture of stem cells. The ability to grow stem cells on microcarriers in agitated culture means that the cultures can be scaled up into suspension conditions. Controlled bioreactors such as the Wave Bioreactor or stirred cultures may be used. This enables cells to be expanded in larger volumes compared to the current limitations of anchorage dependent 2 dimensional colony cultures. Large scale suspension culture in bioreactors up to 100's of liters is possible.

ROCK Inhibitor

Methods according to the present invention concern the culture, growth, propagation, proliferation, population expansion and/or differentiation of pluripotent or multipotent cells in the presence of a ROCK inhibitor.

Rho kinase (Rho-associated coiled-coil kinase or ROCK; GenBank Accession No.: NM_005406), a serine/threonine kinase, serves as a target protein for Rho (of which three isoforms RhoA, RhoB and RhoC exist) and has been characterized as a mediator of the formation of RhoA-induced stress fibers and focal adhesions.

ROCK I (alternatively called ROK b) and ROCK II (also known as Rho kinase or ROK a) were originally isolated as RhoA-GTP interacting proteins. The two kinases have 64% overall identity in humans with 89% identity in the catalytic kinase domain. Both kinases contain a coiled-coil region (55% identity) and a pleckstrin homology (PH) domain split by a C1 conserved region (80% identity). See Olson et al (Current Opinion in Cell Biology 2008, 20:242-248, incorporated herein by reference) for a review of ROCK kinase inhibition.

ROCK promotes actin-myosin-mediated contractile force generation through the phosphorylation of downstream target proteins. ROCK phosphorylates LIM kinase-1 and kinase-2 (LIMK1 and LIMK2) at conserved threonines in their activation loops, increasing LIMK activity, and the subsequent phosphorylation of cofilin proteins, which blocks their F-actin-severing activity. ROCK also directly phosphorylates the regulatory myosin light chain (MLC) and the myosin-binding subunit (MYPT1) of the MLC phosphatase to inhibit catalytic activity. ROCK activation leads to a series of events that promote force generation and morphological changes. These events contribute directly to a number of actin-myosin-mediated processes, such as cell motility, adhesion, smooth muscle contraction, neurite retraction, and phagocytosis. In addition, ROCK kinases play roles in proliferation, differentiation, apoptosis, and oncogenic transformation, although these responses can be cell type-dependent.

In the present specification a "ROCK inhibitor" is a molecule, compound, substance or composition capable of inhibiting ROCK I and/or ROCK II, and preferably having an $IC_{50}$ of less than 100 μM, more preferably less than 10 μM, still more preferably less than 1 μM and still more preferably less than 900 nM or less than or equal to one of about 800 nM, 700 nM, 600 nM, or 500 nM. ROCK kinases useful in the present invention may have an $IC_{50}$ that is substantially the same as or better than (i.e. less than) that of Y-27632 or within 500 nM of the $IC_{50}$ of Y-27632, as measured in the same ROCK kinase assay.

In this specification a "ROCK Inhibitor" also refers to Aurothioglucose and LY294002, which are principally known as inhibitors of NFKappaB and PI3 kinase. As such, the use of a ROCK Inhibitor in the aspects and embodiments described herein includes the use of an inhibitor of NFKappaB and/or PI3 kinase.

ROCK Kinase inhibition assays are well known in the art. For example, the HTScan® ROCK2 Kinase Assay Kit #7508 (Cell Signalling Technology, Inc.), and the ROCK-II Assay Kits Product No.s R8163 and R8164 (Molecular Devices).

In the methods of the present invention the amount of ROCK inhibitor added to a culture will normally take account of the manufacturer's instructions and the size of the culture. For example, typical concentrations of ROCK inhibitor will be in the range 10-50 μM. ROCK Inhibitor may be added regularly to the culture media, e.g. daily, to maintain a desired concentration.

ROCK inhibitor may be added to the culture media so that the concentration of ROCK Inhibitor in the culture media is one of: at least 1 μM, at least 2 μM, at least 3 μM, at least 4 μM, at least 5 μM, at least 6 μM, at least 7 μM, at least 8 μM, at least 9 μM, at least 10 μM, at least 15 μM, at least 20 μM, at least 30 μM, at least 40 μM, or at least 50 μM. The ROCK inhibitor may optionally be present in the culture media at a concentration of less than one of: 100 μM, 90 μM, 80 μM, 70 μM, or 60 μM.

A ROCK Inhibitor may be provided as a salt, base, ester or prodrug of the active agent.

Examples of ROCK inhibitors include:

(A) Y-27632

Y-27632 is a highly potent, cell permeable, selective and ATP competitive inhibitor of ROCK I and ROCK II having an $IC_{50}$ of about 800 nM, and having the structure (1), as follows:

Y-27632 is commonly manufactured and sold as a dihydrochloride [(R)-(+)-trans-N-(4-Pyridyl)-4-(1-aminoethyl)-cyclohexanecarboxamide.2HCl].

Y-27632 is reviewed in the following published papers, all of which are incorporated herein by reference:

Calcium sensitization of smooth muscle mediated by a Rho-associated protein kinase in hypertension: M. Uehata, et al.; Nature 389, 990 (1997)

Molecular dissection of the Rho-associated protein kinase (p160ROCK)-regulated neurite remodeling in neuroblastoma N1E-115 cells: M. Hirose, et al.; J. Cell Biol. 141, 1625 (1998)

Signaling from Rho to the actin cytoskeleton through protein kinases ROCK and LIM-kinase: M. Maekawa, et al.; Science 285, 895 (1999)

Specificity and mechanism of action of some commonly used protein kinase inhibitors: S. P. Davies, et al.; Biochem. J. 351, 95 (2000)

Use and properties of ROCK-specific inhibitor Y-27632: S, Narumiya, et al.; Meth. Enzymol. 325, 273 (2000)

Pharmacological properties of Y-27632, a specific inhibitor of rho-associated kinases: T. Ishizaki, et al.; Mol. Pharmacol. 57, 976 (2000)

A p160ROCK-specific inhibitor, Y-27632, attenuates rat hepatic stellate cell growth: H. Iwamoto, et al.; J. Hepatol. 32, 762 (2000)

Y-27632, an inhibitor of rho-associated protein kinase, suppresses tumor cell invasion via regulation of focal adhesion and focal adhesion kinase: F. Imamura, et al.; Jpn. J. Cancer Res. 91, 811 (2000)

The effect of a Rho kinase inhibitor Y-27632 on superoxide production, aggregation and adhesion in human polymorphonuclear leukocytes: A. Kawaguchi, et al.; Eur. J. Pharmacol. 403, 203 (2000)

Antagonism of Rho-kinase stimulates rat penile erection via a nitric oxide-independent pathway: K. Chitaley, et al.; Nat. Med. 7, 119 (2001)

Inhibition of intrahepatic metastasis of human hepatocellular carcinoma by Rho-associated protein kinase inhibitor Y-27632: M. Takamura, et al.; Hepatology 33, 577 (2001)

Inhibition of high K+-induced contraction by the ROCKs inhibitor Y-27632 in vascular smooth muscle: possible involvement of ROCKs in a signal transduction pathway: K. Sakamoto, et al.; J. Pharmacol. Sci. 92, 56 (2003).

(B) HA-1077 (Fasudil)

HA-1077 is an inhibitor of myosin light chain kinase and $Ca^{2+}$/calmodulin-dependent protein kinase II. It inhibits translocation of PKCβ1, PKCβ11 and PKCζ and is a cell permeable $Ca^{2+}$ antagonist with antivasospastic properties. It has a molecular weight of ~291.36. It inhibits ROCK by competing with ATP. $IC_{50}$ for ROCK 1 of 1.2 mmol/l and $IC_{50}$ for ROCK2 of 0.82 mmol/l. It also has non-specific inhibitory effects on other serine/threonine kinases, e.g. $IC_{50}$ for PKA of 5.3 mmol/l and $IC_{50}$ for PKCa of >100 mmol/l. The dihydrochloride has the structure (2) as follows:

HA-1077 is reviewed in the following published papers, all of which are incorporated herein by reference:

The effects of an intracellular calcium antagonist HA 1077 on delayed cerebral vasospasm in dogs: 0. Shibuya, et al.; Acta Neurochir. 90, 53 (1988)

Vasodilator actions of HA 1077 in vitro and in vivo putatively mediated by the inhibition of protein kinase: T. Asano, et al.; Br. J. Pharmacol. 98, 1091 (1989).

(C) HA-1100 (HydroxyFasudil)

HA-1100 is a cell permeable, hydroxylated metabolite of HA-1077 that acts as an ATP-competitive and reversible inhibitor of Rho kinase (ROCK) with ~100-fold greater selectivity over MLCK, MRCKIβ and PKC. Molecular weight of ~343.8. It has a more selective inhibitory effect on ROCK than Fasudil: $IC_{50}$ for ROCK 1 of 0.73 mmol/l and $IC_{50}$ for ROCK2 of 0.72 mmol/l. It also has non-specific inhibitory effects on other serine/threonine kinases, e.g. $IC_{50}$ for PKA of 37 mmol/l and $IC_{50}$ for PKCa of >100 mmol/l. The hydrochloride has the structure (3) as follows:

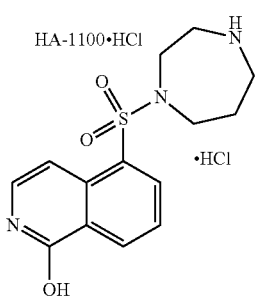 [SMILES: O=S(=O)(c1cccc2c(O)nccc12)N1CCCNCC1 ; Cl]

HA-1100 is reviewed in the following published papers, all of which are incorporated herein by reference:

Rho-kinase-mediated pathway induces enhanced myosin light chain phosphorylations in a swine model of coronary artery spasm: H. Shimokawa, et al.; Cardiovasc. Res. 43, 1029 (1999)

Hydroxyfasudil, an active metabolite of fasudil hydrochloride, relaxes the rabbit basilar artery by disinhibition of myosin light chain phosphatase: K. Nakamura, et al.; J. Cereb. Blood Flow Metab. 21, 876 (2001)

Pitavastatin enhanced BMP-2 and osteocalcin expression by inhibition of Rho-associated kinase in human osteoblasts: K. Ohnaka, et al.; BBRC 287, 337 (2001)

Antianginal effects of hydroxyfasudil, a Rho-kinase inhibitor, in a canine model of effort angina: T. Utsunomiya, et al.; Br. J. Pharmacol. 134, 1724 (2001).

(D) H-1152 (Rho Kinase Inhibitor I)

H-1152 [(S)-(+)-2-Methyl-1-[(4-methyl-5-isoquinolinyl)sulfonyl]homopiperazine] is a cell permeable, highly specific, potent and ATP-competitive inhibitor of Rho kinase (ROCK) ($K_i$=1.6 nM). It is more potent and selective than Y-27632. $K_i$ ROCK of 1.6 nM ($K_i$ PKA:630 nM, $K_i$ PKC:9.27 μM, K, MLCK: 10.1 μM). Molecular weight of ~392.3. The dihydrochloride of H-1152 has the structure (4) as follows:

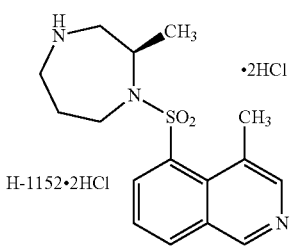 [SMILES: Cc1cncc2cccc(S(=O)(=O)N3CCCNC[C@H]3C)c12]

HA-1152 is reviewed in the following published papers, all of which are incorporated herein by reference:

Inhibition of rho-kinase-induced myristoylated alanine-rich C kinase substrate (MARCKS) phosphorylation in human neuronal cells by H-1152, a novel and specific Rho-kinase inhibitor: M. Ikenoya, et al.; J. Neurochem. 81, 9 (2002)

The novel and specific Rho-kinase inhibitor (S)-(+)-2-methyl-1-[(4-methyl-5-isoquinoline)sulfonyl]-homopiperazine as a probing molecule for Rho-kinase-involved pathway: Y. Sasaki, et al.; Pharmacol. Ther. 93, 225 (2002)

New aspects of neurotransmitter release and exocytosis: Rho-kinase-dependent myristoylated alanine-rich C-kinase substrate phosphorylation and regulation of neurofilament structure in neuronal cells: Y. Sasaki; J. Pharmacol. Sci. 93, 35 (2003)

Protein kinase A in complex with Rho-kinase inhibitors Y-27632, Fasudil, and H-1152P: structural basis of selectivity: C. Breitenlechner, et al.; Structure 11, 1595 (2003)

Involvement of Rho-kinase in inflammatory and neuropathic pain through phosphorylation of myristoylated alanine-rich C-kinase substrate (MARCKS): S. Tatsumi, et al.; Neuroscience 131, 491 (2005)

Rho-kinase mediates spinal nitric oxide formation by prostaglandin E2 via EP3 subtype: S. Matsumura, et al.; BBRC 338, 550 (2005).

(E) 3-(4-Pyridyl)-1H-indole 3-(4-Pyridyl)-1H-indole is a cell permeable, selective, and ATP-competitive inhibitor of Rho kinase (ROCK) (IC50=25 μM), shown to be less potent than Y-27632 and having the structure (5) as follows:

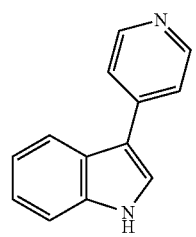

3-(4-Pyridyl)-1H-indole 3-(4-Pyridyl)-1H-indole is reviewed in the following published papers, all of which are incorporated herein by reference:

Screening for cell migration inhibitors via automated microscopy reveals a Rho-kinase inhibitor: J.C. Yarrow, et al.; Chem. Biol. 12, 385 (2005)

Scratch n' screen for inhibitors of cell migration: J. Soderholm & R. Heald; Chem. Biol. 12, 263 (2005).

(F) N-(4-Pyridyl)-N'-(2,4,6-trichlorophenyl)urea (Rho Kinase Inhibitor II)

N-(4-Pyridyl)-N'-(2,4,6-trichlorophenyl) urea is a potent, selective, and ATP-competitive inhibitor of Rho kinase (ROCK) ($IC_{50}$=0.2 μM), having the structure (6) as follows:

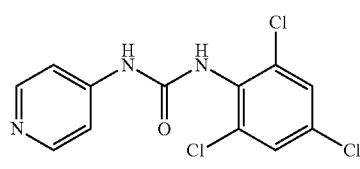

N-(4-Pyridyl)-N'-(2,4,6-trichlorophenyl)urea

N-(4-Pyridyl)-N'-(2,4,6-trichlorophenyl) urea is reviewed in the following published paper, which is incorporated herein by reference:

Design and synthesis of Rho kinase inhibitors (I): A. Takami, et al.; Bioorg. Med. Chem. 12, 2115 (2004).

(G) Aurothioglucose

Aurothioglucose, also known as gold thioglucose, has the formula $AuSC_6H_{11}O_5$:

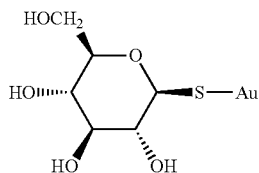

Aurothioglucose is a PKCiota-Par6 interaction inhibitor. Disruption of this interaction disrupts the Rac I signaling pathway required for transformed growth in non-small lung cell cancer. $IC_{50}$: 1 µM.

Aurothioglucose inhibits induced NF-kB and AP-1 activity by acting as an IL-1 functional antagonist.

Aurothioglucose is known for its action in reducing inflammation and swelling due to arthritis. And has been used in the treatment of early stages of adult or juvenile rheumatoid arthritis.

Gold (I)-containing compounds, including aurothioglucose (ATG), are potent in vitro inhibitors of several selenocysteine-containing enzymes. (Smith et al J. Nutr. 1999 January; 129(1):194-8). Aurothioglucose is implicated in Protein Kinase C mediated inhibition (Stallings-Mann M et al. A novel small-molecule inhibitor of protein kinase C blocks transformed growth of non-small cell lung cancer cells. Cancer Res 2006; 66:1767-74 and Beverly A. Teicher. Protein Kinase C as a Therapeutic Target. Clin Cancer Res 2006; 12(18) Sep. 15, 2006).

Aurothioglucose has been shown to inhibit induced NF-kB and AP-1 activity by acting as an IL-1 functional antagonist (Williams, D H: Jeffery, L J: Murray, E J Biochim-Biophys-Acta. 1992 Oct. 13; 1180(1): 9-14).

Aurothioglucose has also been shown to inhibit TPA-induced NF-kappaB nuclear translocation (Yamashita M et al. Inhibition of TPA-induced NF-kappaB nuclear translocation and production of NO and PGE2 by the anti-rheumatic gold compounds. J Pharm Pharmacol. 2003 February; 55(2):245-51).

(H) LY294002

LY294002 has the structure (7) as follows:

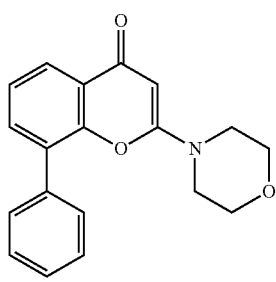 [SMILES: O=c1cc(N2CCOCC2)oc2c(-c3ccccc3)cccc12]

LY294002 (a phosphatidylinositol 3 kinase Inhibitor) has been shown to act in vivo as a highly selective inhibitor of phosphatidylinositol 3 (PI3) kinase. Used at a concentration of 50 µM, it specifically abolished PI3 kinase activity ($IC_{50}$=0.43 µg/ml; 1.40 µM) but did not inhibit other lipid and protein kinases such as P14 kinase, PKC, MAP kinase or c-Src (Vlahos, C. (1994) J. Biol. Chem. 269, 5241-5248).

Other ROCK Inhibitors include Wf-536 (Nakajima et al., Cancer Chemother Pharmacol. 52(4): 319-324 (2003)) and Y-30141 (see U.S. Pat. No. 5,478,838) as well as antisense nucleic acids for ROCK, RNA interference nucleic acids for ROCK (e.g. siRNA).

Positive Charge

The particle or microcarrier may comprise a positive charge at for example neutral pH or physiologically relevant pH such as pH 7.4 or pH 7.2. The particle may comprise a chromatography resin such as an anion exchange resin.

The quantity of positive charge may vary, but in some embodiments is intended to be high enough to enable cells to attach to the particle. For example, where the particles are charged by coupling with amines, such as quaternary or tertiary amines, the charge on the particle may correspond to a small ion exchange capacity of about 0.5 to 4 milli-equivalents per gram dry material (of the particle), for example between about 1 to 3.5 milli-equivalents per gram dry material (of the particle) or between about 1 to 2 milli-equivalents per gram dry material (of the particle).

The positive charge may be such that that the pKa of the particle is greater than 7 (e.g., greater than 7.4, e.g., 7.5, 8, 8.5, 9, 9.5, 10, 10.5, 11, 11.5 or more).

The particle may be derivatised by coupling for example to protamine sulphate or poly-L-lysine hydrobromide at a concentration of up to 20 mg/ml particles.

Without wishing to be bound by theory, we believe that the presence of a positive charge on the particles assists attachment of cells thereto.

The particle may carry a positive charge through any means known in the art. The particle may comprise positively charged groups, or it may be derivatised to carry these.

The particle may comprise diethylaminoethyl-cellulose (DEAE-cellulose) or a derivative thereof. DEAE-cellulose comprises a microgranular cellulose which has been chemically modified such that the —$CH_2OH$ groups of the carbohydrate have been converted to an ionizable tertiary amine group. It is positively charged at neutral pH.

The particle may comprise a Sephadex bead, such as DEAE-Sephadex. The particle may comprise agarose bead which may be covalently cross-linked, such as Sepharose (i.e., DEAE-Sepharose). The particle may comprise DEAE-Sephacel. DEAE-Sepharose, DEAE-Sephacel and DEAE-Sephadex are available from Sigma-Aldrich. The particle may comprise Q-Sepharose Fast Flow or S-Sepharose Fast Flow. The charged group of Q-Sepharose is a quarternary amine which carries a non-titratable positive charge.

The particle may be derivatised to carry positive charges. For example, the particle may comprise amine groups attached thereto. The amine groups may be primary amine groups, secondary amine groups, tertiary amine groups or quaternary amine groups. The amine groups may be attached to the particle by coupling the particle with amine containing compounds. Methods of coupling are well known in the art. For example, the amine may be coupled to the particle by the use of cyanogen bromide.

Crosslinkers may also be used. These are divided into homobifunctional crosslinkers, containing two identical reactive groups, or heterobifunctional crosslinkers, with two different reactive groups. Heterobifunctional crosslinkers allow sequential conjugations, minimizing polymerization. Coupling and crosslinking reagents may be obtained from a number of manufacturers, for example, from Calbiochem or Pierce Chemical Company. The particle may be activated prior to coupling, to increase its reactivity. The compact particle may be activated using chloroacetic acid followed by coupling using EDAC/NHS—OH. Particles may also be activated using hexane di isocyanate to give a primary amino group. Such activated particles may be used in combination with any heterobifunctional cross linker. The compact particle in certain embodiments is activated using divinyl sulfon. Such activated compact particles comprise moieties which can react with amino or thiol groups, on a peptide, for example.

The particle may also be activated using tresyl chloride, giving moieties which are capable of reacting with amino or thiol groups. The particle may also be activated using cyanogen chloride, giving moieties which can react with amino or thiol groups.

Cytodex 1 is based on a cross-linked dextran matrix which is substituted with positively charged N,N-diethylaminoethyl groups. The charged groups are distributed throughout the microcarrier matrix.

Uncharged Particles

The particle or microcarrier may be uncharged, or charge neutral at for example neutral pH or physiologically relevant pH such as pH 7.4 or pH 7.2.

Examples of uncharged particles include gelatine or collagen particles. For example, Cytodex 3 consists of a thin layer of denatured collagen chemically coupled to a matrix of cross-linked dextran.

Matrix Coating

It is central to the present invention that the use of a ROCK inhibitor has been found by the inventors to enable the successful culture and passaging of pluripotent and multipotent cells on microcarriers in the absence of a matrix coating on the microcarriers. Until now, it had been thought that microcarrier culture of pluripotent and multipotent cells required the microcarriers to have a matrix coating and the present invention opens the door to uncoated microcarrier culture which is more amenable for GMP compliance. Accordingly, in many embodiments the microcarriers are uncoated, or do not have a matrix coating but may be otherwise coated or derivatised to provide a charge to the surface of the microcarrier. However, in other embodiments, as described below, it is possible to include a matrix coating.

Accordingly, the particle may be coated with a matrix, which in the context of this document refers to a layer (e.g. a thin layer or film) of substance attached to the particle such as on its surface. The matrix may comprise a biologically or compatible or physiologically relevant matrix capable of supporting growth of cells. It may comprise a substrate for cell growth.

The matrix may comprise a component of the extracellular matrix (ECM). Any of the known components of the ECM such as those capable of supporting growth of stem cells may be used. Components of the extracellular matrix are known in the art and are described in for example Alberts et at (2002), Molecular Biology of the Cell, Chapter IV and references cited therein.

The ECM component may be attached or coupled to or coated on the particle through conventional means. For example, any of the coupling reagents and crosslinkers described above may be used to couple the ECM component to the particle.

The ECM component may comprise a macromolecule such as a polysaccharide, protein, proteoglycan, glycoprotein, glycosaminoglycan (GAG), usually found covalently linked to protein in the form of proteoglycans, a fibrous protein, including elastin, fibronectin, and laminin, collagen (e.g. collagen I, collagen III, collagen IV, collagen VI) etc.

The matrix coating may comprise a glycosaminoglycan (GAG). Glycosaminoglycans comprise unbranched polysaccharide chains composed of repeating disaccharide units. One of the two sugars in the repeating disaccharide is always an amino sugar (N-acetylglucosamine or N-acetylgalactosamine), which in most cases is sulfated. The second sugar is usually a uronic acid (glucuronic or iduronic).

The matrix coating may comprise hyaluronan (also called hyaluronic acid or hyaluronate) or a derivative thereof. The hyaluronic acid may be derived from any number of sources, such as from bovine vitreous humor. A salt or base of hyaluronic acid may be employed, such as hyaluronic acid sodium. This may be from streptococcus.

The matrix coating may comprise laminin. The matrix coating may comprise fibronectin. The matrix coating may comprise vitronectin.

The matrix coating may comprise for example a GAG such as chondroitin sulfate, dermatan sulfate, heparan sulfate and keratan sulfate, for example as linked to a protein as a proteoglycan. The ECM component may comprise aggrecan, decorin, etc.

The matrix coating may comprise heparan or its derivatives such as bases or salts. The matrix coating may comprise heparan sulphate proteoglycan. The heparan sulphate proteoglycan may be derived from any number of sources, such as from bovine kidney.

The matrix coating may comprise a dextran such as dextran sulphate or dextran sulphate sodium. The matrix coating may comprise fibronectin, laminin, nidogen or Type IV collagen. The matrix coating may comprise chondroitin sulphate.

The matrix may comprise gelatin, polyornithine, or binding motifs of the RGD binding domain of fibronectin.

The matrix coating may comprise a mixture of any two or more of these components in various proportions. The matrix coating may comprise a purified or substantially purified component of the ECM. The matrix component may comprise a partially purified component of the ECM. It may comprise an ECM extract such as Matrigel.

A cell culture may comprise particles having different matrix coatings. For example, a first particle population having a first matrix coating selected from those described above and a second particle population having a second coating selected from those described above.

Matrigel

The particle may be coated with a matrix coating comprising Matrigel.

Matrigel is the trade name for a gelatinous protein mixture secreted by mouse tumor cells and marketed by BD Biosciences (Bedford, Mass., USA). This mixture resembles the complex extracellular environment found in many tissues and is used by cell biologists as a substrate for cell culture.

BD Matrigel™ Matrix is a solubilised basement membrane preparation extracted from EHS mouse sarcoma, a tumor rich in ECM proteins. Its major component is laminin (about 56%), followed by collagen IV (about 31%), heparan sulfate proteoglycans, and entactin 1 (about 8%). At room temperature, BD Matrigel™ Matrix polymerizes to produce biologically active matrix material resembling the mammalian cellular basement membrane.

A common laboratory procedure is to dispense small volumes of chilled (4° C.) Matrigel onto a surface such as plastic tissue culture labware. When incubated at 37° C. (body temperature) the Matrigel proteins self-assemble producing a thin film that covers the surface.

Matrigel provides a physiologically relevant environment with respect to cell morphology, biochemical function, migration or invasion, and gene expression.

The ability of Matrigel to stimulate complex cell behaviour is a consequence of its heterogeneous composition. The chief components of Matrigel are structural proteins such as laminin and collagen which present cultured cells with the adhesive peptide sequences that they would encounter in their natural environment. Also present are growth factors that promote differentiation and proliferation of many cell types. Matrigel comprises the following growth factors (range of concentrations, average concentration): EGF (0.5-1.3 ng/ml, 0.7 ng/ml), bFGF (<0.1-0.2 pg/ml, unknown), NGF (<0.2 ng/ml, unknown), PDGF (5-48 pg/ml, 12 pg/ml), IGF-1 (11-24 ng/ml, 16 ng/ml), TGF-β (1.7-4.7 ng/ml, 2.3 ng/ml). Matrigel contains numerous other proteins in small amounts.

Alternating Matrix Coatings

In some embodiments cells may be cultured on a particle having a first matrix coating for one or more passages (e.g. 1, 2, 3, 4, 5, 6, 7, 8, 9, or 10 passages or more), before being transferred to particles having a different (second) matrix coating for one or more passages (e.g. 1, 2, 3, 4, 5, 6, 7, 8, 9, or 10 passages or more). Optionally the cells may then be transferred to particles having a matrix coating different to the second coating, e.g. back to the first matrix coating or to another matrix coating or to uncoated particles.

Particle Composition

In the methods and compositions described here, stem cells are propagated on particles or microcarriers. As the term is used in this document, a "particle" comprises any support on which a stem cell can attach or grow. The particle may be of any shape or configuration, as described below.

The particle may comprise a microcarrier, as described in the IUPAC Compendium of Chemical Terminology (2nd Edition, 1992, Vol. 64, p. 160).

The particle may comprise any material, so long as it has the physical properties which allow it to serve its purposes as described above, for example as a point of attachment or support for the stem cells. The particle may therefore comprise material which is stiff, rigid, malleable, solid, porous or otherwise, for this purpose. It may comprise a solid material, or a semi-solid, gel, etc material.

The material is at least reactive to allow attachment of positive charges and/or a matrix coating, or capable of being made reactive by an activator, but may otherwise comprise a generally inert substance. The particle may comprise a composite, such that more than one material may make up the particle. For example, the core of the particle may comprise a different material from surface portions. Thus, the core of the particle may comprise a generally inert material, while the surface portions may comprise material reactive for attachment or chemical coupling of the matrix or positive charges. The particle may be natural in origin, or synthetic. Natural and synthetic materials and sources for obtaining them are well known in the art. The particle may have at least some mechanical resistance, at least some resistance to chemical attack, or to heat treatment, or any combination of these.

In an alternative embodiment, the particle may comprise a "non-biological" object, by which term we mean a particle which is free or substantially free of cellular material. Such a non-biological or non-cellular particle may therefore comprise a synthetic material, or a non-naturally occurring material. Various particles of various shapes are known in the art, and include for example, beads of various kinds. Embodiments of particles include microbeads, such as agarose beads, polyacrylamide beads, silica gel beads, etc. For example, the material from which the particle is made may comprise plastic, glass, ceramic, silicone, gelatin, dextran, cellulose, hydroxylated methacrylate, polystyrene, collagen or others. For example, the particle may be made of cellulose or a derivative, such as DEAE-cellulose (as described below). The particles may comprise cellulose, modified hydrophilic beads and carbon based microcarriers.

The particle may comprise a commercially available matrix or carrier, such as a bead or microbead. The particle may comprise a resin sold for use as a chromatography matrix, such as an anion exchange resin.

The particle may comprise a cellulose microcarrier. The particle may comprise DE-52 (Whatman), DE-53 (Whatman) or QA-52 (Whatman). The particle may comprise a hydrophilic microcarrier, a hydroxylated methacrylic matrix microcarrier or derivatised hydrophilic beaded microcarrier. The particle may comprise TSKgel Tresyl-5Pw (Tosoh) or Toyopearl AF-Tresyl-650 (Tosoh). The particle may comprise a macroporous or microporous carboseed microcarrier, for example, SM1010 (Blue Membranes) or SH1010 (Blue Membranes).

The particle may be a dextran based microcarrier. The particle may comprise Cytodex 1 (GE Healthcare) or Cytodex 3 (GE Healthcare). Cytodex 1 is based on a cross-linked dextran matrix which is substituted with positively charged N,N-diethylaminoethyl groups. The charged groups are distributed throughout the microcarrier matrix. Cytodex 3 consists of a thin layer of denatured collagen chemically coupled to a matrix of cross-linked dextran.

The particle may be a polystyrene based microcarrier. The particle may comprise Hillex or Hillex II (SoloHill Engineering, Inc.). Hillex and Hillex II are modified polystyrene microcarriers having a cationic trimethyl ammonium coating.

The particle may be treated prior to allowing cells to grow thereon. Such treatment may seek to achieve greater adherence, availability of charges, biocompatibility, etc, as described elsewhere in this document.

Cellulose microcarriers such as DE-53, DE-52 and QA-52 may be rod-shaped.

A cell culture may comprise a mixture of more than one type of particle. For example, a first particle population (e.g. of compact shape particles) and a second particle population (e.g. of elongate shape particles). In some embodiments a first cell type, e.g. feeder cells, may be attached to the first particles and a second cell type, e.g. hESCs, may be attached to the second particles. Each particle type may have the same or a different matrix coating. Optionally one or both particle types may not have a matrix coating.

Beads

Beads or microbeads suitable for use include those which are used for gel chromatography, for example, gel filtration media such as Sephadex. Suitable microbeads of this sort include Sephadex G-10 having a bead size of 40-120 (Sigma Aldrich catalogue number 27, 103-9), Sephadex G-15 having a bead size of 40-120 μm (Sigma Aldrich catalogue number 27, 104-7), Sephadex G-25 having a bead size of 20-50 μm (Sigma Aldrich catalogue number 27, 106-3), Sephadex G-25 having a bead size of 20-80 μm (Sigma Aldrich catalogue number 27, 107-1), Sephadex G-25 having a bead size of 50-150 μm (Sigma Aldrich catalogue number 27, 109-8), Sephadex G-25 having a bead size of 100-300 μm (Sigma Aldrich catalogue number 27, 110-1), Sephadex G-50 having a bead size of 20-50 μm (Sigma Aldrich catalogue number 27, 112-8), Sephadex G-50 having a bead size of 20-80 μm (Sigma Aldrich catalogue number 27, 113-6), Sephadex G-50 having a bead size of 50-150 μm (Sigma Aldrich catalogue number 27, 114-4), Sephadex G-50 having a bead size of 100-300 μm (Sigma Aldrich catalogue number 27, 115-2), Sephadex G-75 having a bead size of 20-50 μm (Sigma Aldrich catalogue number 27, 116-0), Sephadex G-75 having a bead size of 40-120 μm (Sigma Aldrich catalogue number 27, 117-9), Sephadex G-100 having a bead size of 20-50 μm (Sigma Aldrich catalogue number 27, 118-7), Sephadex G-100 having a bead size of 40-120 μm (Sigma Aldrich catalogue number 27, 119-5), Sephadex G-150 having a bead size of 40-120 µm (Sigma Aldrich catalogue number 27, 121-7), and Sephadex G-200 having a bead size of 40-120 µm (Sigma Aldrich catalogue number 27, 123-3), so long as they are compatible in terms of size, as explained elsewhere in this document.

Sepharose beads, for example, as used in liquid chromatography, may also be used. Examples are Q-Sepharose, S-Sepharose and SP-Sepharose beads, available for example from Amersham Biosciences Europe GmbH (Freiburg, Germany) as Q Sepharose XL (catalogue number 17-5072-01), Q Sepharose XL (catalogue number 17-5072-04), Q Sepharose XL (catalogue number 17-5072-60), SP Sepharose XL (catalogue number 17-5073-01), SP Sepharose XL (catalogue number 17-5073-04) and SP Sepharose XL (catalogue number 117-5073-60) etc.

Particle Shape

The particle may comprise any suitable shape for cell growth, e.g., a compact shape or an elongate shape.

Compact Shape

Examples of compact shapes are generally spherical shaped particles, ellipsoid shaped particles, or granular shaped particles.

By "compact", we mean a shape which is not generally elongate. In other words, "compact" shapes are those which are generally non-elongate or unextended, or which are not extended in any one dimension. The compact shape may be one which is not generally spread out, or not long or spindly. Therefore, such "compact shapes" generally possess linear dimensions which may be generally similar, or which do not differ by a large amount.

Thus, the ratio of any two dimensions of the compact shape may be 5:1 or less, such as 4:1 or less, such as 3:1, 2.5:1, 2.4:1, 2.3:1, 2.2:1, 2.1:1, 2:1, 1.9:1, 1.8:1, 1.7:1, 1.6:1, 1.5:1, 1.4:1, 1.3:1, 1.2:1, 1.1:1, or less. For example, no two pairs of dimensions may have a ratio of 5:1 or more.

In some embodiments, the longest dimension of the compact shape is less than five times the shortest dimension of the compact shape. In other embodiments, the longest dimension of the compact shape is not significantly greater than the shortest dimension, i.e., the shape is relatively uniform.

The "longest dimension" as the term is used in this document should be taken to mean the length of the major axis, i.e., the axis containing the longest line that can be drawn through the particle. Similarly, the "shortest dimension" is the length of the minor axis, which is the axis containing the shortest line that can be drawn through the particle.

Regular shapes in which the linear dimensions are approximately the same, or are comparable, or in which the ratio of the longest dimension to the shortest dimension is less than 5:1 are included in the compact particles described here. The above ratios may therefore relate to the ratio of the longest dimension to the shortest dimension. In some embodiments, the ratio of two dimensions (such as the longest dimension to the shortest dimension) is less than 1.1:1, such as 1:1 (i.e., a regular or uniform shape).

Therefore, where applicable, the length of the particle may be less than 5× its width or diameter, such as less than 4× its width or diameter, such as less than 3×, such as less than 2× or less.

The compact shape may comprise a regular solid, a sphere, a spheroid, an oblate spheroid, a flattened spheroid, an ellipsoid, a cube, a cone, a cylinder, or a polyhedron. Polyhedra include simple polyhedra or regular polyhedra. Polyhedra include, for example, a hexahedron, holyhedron, cuboid, deltahedron, pentahedron, tetradecahedron, polyhedron, tetraflexagon, trapezohedron, truncated polyhedron, geodesic dome, heptahedron and hexecontahedron. Any of the above shapes may be used such that they are "compact", according to the definition provided above. For example, where the shape comprises an oblate spheroid, this has the appropriate oblateness such that the spheroid is compact, and not elongate.

In some embodiments, the compact shape may comprise a balloon shape, a cigar shape, a sausage shape, a disc shape, a teardrop shape, a ball shape or an elliptical shape, so long as the dimensions are as given above. The compact shape may also comprise a sphere shape, a cube shape, a cuboid shape, a tile shape, an ovoid shape, an ellipsoid shape, a disc shape, a cell shape, a pill shape, a capsule shape, a flat cylinder shape, a bean shape, a drop shape, a globular shape, a pea shape, a pellet shape, etc.

Elongate Shape

The particle may have a generally elongate shape. Examples of elongate shapes are generally rod shaped particles, cylindrical shaped particles, or stick shaped particles. The elongate particles may comprise hollow fibres.

By "elongate", we mean a shape which is not generally compact. In other words, "elongate" shapes are those which are generally extended in one dimension relative to another. The elongate shape may be one which is spread out, long or spindly. Therefore, such "elongate shapes" generally possess linear dimensions which generally differ from one another to a greater or lesser extent.

Thus, the ratio of any two dimensions of the elongate shape may be 5:1 or more, 4:1 or less, such as 1.1:1 or more, 1.2:1 or more, 1.3:1 or more, 1.4:1 or more, 1.5:1 or more, 1.6:1 or more, 1.7:1 or more, 1.8:1 or more, 1.9:1 or more, 2:1 or more, 2.1:1 or more, 2.2:1 or more, 2.3:1 or more, 2.4:1 or more, 2.5:1 or more, 3:1 or more, 4:1 or more, or 5:1 or more.

For example, any two pairs of dimensions may have a ratio of 5:1 or more. Thus, in some embodiments, the longest dimension of the elongate shape is more than five times the shortest dimension of the elongate shape.

Therefore, where applicable, the length of the particle may be more than 2× its width or diameter, such as more than 3× its width or diameter, such as more than 4×, such as more than 5× or more than 10×.

Elongate or rod-shaped microcarriers are especially preferred for use in the methods of the present invention. They are observed to provide a better attachment matrix for the generation of cell-microcarrier aggregates. Whilst not being limited or bound by theory, it is considered that the long axis of a rod-shaped microcarrier provides a superior attachment compared to bead (spherical) microcarriers due to the large surface area that is available for attachment enabling cell-carrier aggregation within a few hours that is stable during agitation.

Particle Size

In order for the particles to support continuous growth, they may have a size which enables cells to grow on the particles. The size of the particles also enables cells to aggregate with other cells growing on other particles. For example, it may be necessary for the size of the particle to be such that at least one dimension is compatible with the dimensions of a primate or human stem cell.

The size of the particles may be chosen empirically by selecting a particle, allowing stem cells to attach on and grow, and assaying any of a number of parameters such as growth, viability, retention of biological characters of stem cells, karyotype, etc.

As an example, the particle may comprise a compact microcarrier having a generally spherical or granular shape.

Where this is the case, the compact microcarrier may have a dimension ranging between about 20 µm and about 250 µm.

The upper limit of the range of dimensions for the compact microcarrier may be about 250 µm, about 240 µm, about 230 µm, about 220 µm, about 210 µm, about 200 µm, about 190 µm, about 180 µm, about 170 µm, about 160 µm, about 150 µm, about 140 µm, about 130 µm, about 120 µm, about 110 µm, about 100 µm, about 90 µm, about 80 µm, about 70 µm, about 60 µm, about 50 µm, about 40 µm or about 30 µm.

The lower limit of the range of dimensions of the compact microcarrier may be about 20 µm, about 30 µm, 40 µm, about 50 µm, about 60 µm, about 70 µm, about 80 µm, about 90 µm, about 100 µm or about 110 µm.

The compact microcarriers may have a dimension between 120 µm to 20 µm, 110 µm to 30 µm, 100 µm to 40 µm, 90 µm to 50 µm, 80 µm to 40 µm, 70 µm to 50 µm or between 90 to 30 µm, 80 to 40 µm, 70 to 40 µm, 70 to 30 µm, 60 to 40 µm, 60 to 30 µm, 60 to 50 µm, 50 to 40 µm, 50 to 30 µm, 50 to 5 µm, 50 to 10 µm, 60 to 10 µm, 70 to 10 µm, 60 to 20 µm, 70 to 20 µm.

The compact microcarrier may have a dimension of about 20 µm, about 30 µm, 40 µm, about 50 µm, about 60 µm, about 65 µm, about 70 µm, about 80 µm, about 90 µm, about 100 µm, about 110 µm or about 120 µm.

The dimensions of the compact microcarrier may for example be about 65 µm.

The dimension may be the diameter of the microcarrier.

The compact particle may for example comprise a hydrophilic microcarrier, a hydroxylated methacrylic matrix microcarrier or derivatised hydrophilic beaded microcarrier, such as TSKgel Tresyl-5Pw (Tosoh) or Toyopearl AF-Tresyl-650 (Tosoh). Information on TSKgel Tresyl-5Pw may be found at: http://www.separations.us.tosohbioscience.com/Products/HPLCColumns/ByMode/Affinity/TSKgel+Tresyl-5PW.htm Information on Toyopearl AF-Tresyl-650 may be found at: http://www.separations.us.tosohbioscience.com/Products/ProcessMedia/ByMode/AFC/To yopearlAF-Tresyl-650.htm As another example, the particle may comprise an elongate microcarrier having a generally rod- or cylindrical shape. Where this is the case, the elongate microcarrier may have a longest dimension ranging between about 400 µm and about 50 µm.

The upper limit of the range of longest dimensions for the elongate microcarrier may be about 2000 µm, about 1900 µm, about 1800 µm, about 1700 µm, about 1600 µm, about 1500 µm, about 1400 µm, about 1300 µm, about 1200 µm, about 1100 µm, about 1000 µm, about 900 µm, about 800 µm, about 700 µm, about 600 µm, about 500 µm, about 400 µm, about 390 µm, about 380 µm, about 370 µm, about 360 µm, about 350 µm, about 340 µm, about 330 µm, about 320 µm, about 310 µm, about 300 µm, about 290 µm, about 280 µm, about 270 µm, about 260 µm, about 250 µm, about 240 µm, about 230 µm, about 220 µm, about 210 µm, about 200 µm, about 190 µm, about 180 µm, about 170 µm, about 160 µm, about 150 µm, about 140 µm, about 130 µm, about 120 µm, about 110 µm, about 100 µm, about 90 µm, about 80 µm, about 70 µm, about 60 µm or about 50 µm.

The lower limit of the range of longest dimensions of the elongate microcarrier may be about 20 µm, about 30 µm, about 40 µm, about 50 µm, about 60 µm, about 70 µm, about 80 µm, about 90 µm, about 100 µm, about 110 µm, about 120 µm, about 130 µm, about 140 µm, about 150 µm, about 160 µm, about 170 µm, about 180 µm, about 190 µm, about 200 µm, about 210 µm, about 220 µm, about 230 µm, about 240 µm, about 250 µm, about 260 µm, about 270 µm, about 280 µm, about 290 µm, about 300 µm, about 310 µm, about 320 µm, about 330 µm, about 340 µm, about 350 µm, about 360 µm, about 370 µm, about 380 µm or about 390 µm.

The elongate microcarrier may have a longest dimension between 2000 µm to 20 µm, for example between 400 µm to 50 µm, 390 µm to 60 µm, 380 µm to 70 µm, 370 µm to 80 µm, 360 µm to 90 µm, 350 µm to 100 µm, 340 µm to 110 µm, 330 µm to 120 µm, 320 µm to 130 µm, 310 µm to 140 µm, 300 µm to 150 µm, 290 µm to 160 µm, 280 µm to 170 µm, 270 µm to 180 µm, 260 µm to 190 µm, 250 µm to 200 µm, 240 µm to 210 µm or 230 µm to 220 µm. The longest dimension of the elongate microcarrier may for example be about 190 µm, 200 µm, 210 µm, 220 µm, etc.

The elongate microcarrier may have a shortest dimension ranging between 10 µm and 50 µm. The elongate microcarrier may have a shortest dimension of about 10 µm, about 15 µm, about 20 µm, about 25 µm, about 30 µm, about 35 µm, about 40 µm or about 45 µm.

An elongate microcarrier may be cylindrical or rod-shaped, having an approximately circular or ellipsoid cross-section, the shortest diameter of which may be in the range of about 5 µm to about 50 µm, for example one of about 10 µm, about 15 µm, about 20 µm, about 25 µm, about 30 µm, about 35 µm, about 40 µm, or about 45 µm. The diameter may be between one of: about 5 µm and 20 µm, about 10 µm and 25 µm, about 15 µm and 30 µm, about 20 µm and 35 µm, about 25 µm and 40 µm, about 30 µm and 45 µm, about 35 µm and 50 µm.

The elongate particle may for example comprise a cellulose cylindrical microcarrier, such as DE-52 (Whatman), DE-53 (Whatman) or QA-52 (Whatman).

The size and dimensions of any given microcarrier may vary, within or between batches. For example, for DE-53 rod-shaped cellulose microcarriers we measured the length and diameter of the microcarriers within a batch and found that the length of carrier can be between 50 and 250 µm (average length of 130±50 µm) and the diameter of the carrier can be between 17 µm and at least 50 µm (average diameter of 35±7 µm).

The particle may be porous or non-porous. Porous particles enable medium to circulate within and through the growing area and this may assist cell growth. For example, the particle may comprise a macroporous or microporous carboseed microcarrier. The particle may comprise SM1010 (Blue Membranes) or SH1010 (Blue Membranes).

Culture of Stem Cells

Any suitable method of culturing stem cells, for example as set out in the Examples, may be used in the methods and compositions described here.

Any suitable container may be used to propagate stem cells according to the methods and compositions described here. Suitable containers include those described in US patent Publication US2007/0264713 (Terstegge).

Containers may include bioreactors and spinners, for example. A "bioreactor", as the term is used in this document, is a container suitable for the cultivation of eukaryotic cells, for example animal cells or mammalian cells, such as in a large scale. A typical cultivation volume of a regulated bioreactor is between 20 ml and 500 ml.

The bioreactor may comprise a regulated bioreactor, in which one or more conditions may be controlled or monitored, for example, oxygen partial pressure. Devices for measuring and regulating these conditions are known in the art. For example, oxygen electrodes may be used for oxygen partial pressure. The oxygen partial pressure can be regulated via the amount and the composition of the selected gas mixture (e.g., air or a mixture of air and/or oxygen and/or nitrogen and/or carbon dioxide). Suitable devices for measuring and regulating the oxygen partial pressure are described by Bailey, J E. (Bailey, J E., Biochemical Engineering Fundamentals, second edition, McGraw-Hill, Inc. ISBN 0-07-003212-2 Higher Education, (1986)) or Jackson A T. Jackson A T., Verfahrenstechnik in der Biotechnologie, Springer, ISBN 3540561900 (1993)). Other suitable containers include spinners. Spinners are regulated or unregulated bioreactors, which can be agitated using various agitator mechanisms, such as glass ball agitators, impeller agitators, and other suitable agitators. The cultivation volume of a spinner is typically between 20 ml and 500 ml. Roller bottles are round cell culture flasks made of plastic or glass having a culture area of between 400 and 2000 cm$^2$. The cells are cultivated along the entire inner surface of these flasks; the cells are coated with culture medium accomplished by a "rolling" motion, i.e. rotating the bottles about their own individual axis.

Alternatively, culture may be static, i.e. where active agitation of the culture/culture media is not employed. By reducing agitation of the culture aggregates of cells/microcarriers may be allowed to form. Whilst some agitation may be employed to encourage distribution and flow of the culture media over the cultured cells this may be applied so as not to substantially disrupt aggregate formation. For example, a low rpm agitation, e.g. less than 30 rpm or less than 20 rpm, may be employed.

Propagation with Passage

The methods and compositions described here may comprise passaging, or splitting during culture. The methods may involve continuous or continual passage.

By "continual" or "continuous", we mean that our methods enable growth of stem cells on microcarriers in a fashion that enables them to be passaged, e.g., taken off the microcarriers on which they are growing and transferred to other microcarriers or particles, and that this process may be repeated at least once, for example twice, three times, four times, five times, etc (as set out below). In some cases, this may be repeated any number of times, for example indefinitely or infinitely. Most preferably the process is repeated 5 or more times, e.g. 6 or more time, 7 or more times, 8 or more times, 9 or more times, 10 or more times, 11 or more times, 12 or more times, 13 or more times, 14 or more times, 15 or more times, 16 or more times, 17 or more times, 18 or more times, 19 or more times, 20 or more times, 21 or more times, 22 or more times, 23 or more times, 24 or more times, 25 or more times. The terms "continual" or "continuous" may also be used to mean a substantially uninterrupted extension of an event, such as cell growth. For example, our methods enable the expansion of stem cells to any number of desired generations, without needing to terminate the growth or culture.

Cells in culture may be dissociated from the substrate or flask, and "split", subcultured or passaged, by dilution into tissue culture medium and replating.

Cells growing on particles may be passaged back onto particle culture. Alternatively, they may be passaged back onto conventional (2D) cultures. Tissue culture cells growing on plates may be passaged onto particle culture. Each of these methods are described in more detail below.

The term "passage" may generally refer to the process of taking an aliquot of a cell culture, dissociating the cells completely or partially, diluting and inoculating into medium. The passaging may be repeated one or more times. The aliquot may comprise the whole or a portion of the cell culture. The cells of the aliquot may be completely, partially or not confluent. The passaging may comprise at least some of the following sequence of steps: aspiration, rinsing, trypsinization, incubation, dislodging, quenching, re-seeding and aliquoting. The protocol published by the Hedrick Lab, UC San Diego may be used (http://hedricklab.ucsd.edu/Protocol/COSCell.html).

The cells may be dissociated by any suitable means, such as mechanical or enzymatic means known in the art. The cells may be broken up by mechanical dissociation, for example using a cell scraper or pipette. The cells may be dissociated by sieving through a suitable sieve size, such as through 100 micron or 500 micron sieves. The cells may be split by enzymatic dissociation, for example by treatment with collagenase or trypLE harvested. The dissociation may be complete or partial.

The dilution may be of any suitable dilution. The cells in the cell culture may be split at any suitable ratio. For example, the cells may be split at a ratio of 1:2 or more, 1:3 or more, 1:4 or more or 1:5 or more. The cells may be split at a ratio of 1:6 or more, 1:7 or more, 1:8 or more, 1:9 or more or 1:10 or more. The split ratio may be 1:10 or more. It may be 1:11, 1:12, 1:13, 1:14, 1:15, 1:16, 1:17, 1:18, 1:19 or 1:20 or more. The split ratio may be 1:21, 1:22, 1:23, 1:24, 1:25 or 1:26 or more.

Thus, stem cells may be passaged for 1 passage or more. For example, stem cells may be passaged for 2, 3, 4, 5, 6, 7, 8, 9, 10, 11, 12, 13, 14, 15, 16, 17, 18, 19, 20, 21, 22, 23, 24, 25 passages or more. The stem cells may be passaged for 25, 30, 35, 40, 45, 50, 55, 60, 65, 70, 75, 80, 85, 90, 95 or more passages. The stem cells may be propagated indefinitely in culture.

Passages may be expressed as generations of cell growth. Our methods and compositions allow stem cells to propagate for 1, 2, 3, 4, 5, 6, 7, 8, 9, 10, 11, 12, 13, 14, 15, 16, 17, 18, 19, 20, 21, 22, 23, 24, 25 generations or more. The stem cells may be grown for 25, 30, 35, 40, 45, 50, 55, 60, 65, 70, 75, 80, 85, 90, 95 or more generations.

Passages may also be expressed as the number of cell doublings. Our methods and compositions allow stem cells to propagate for 1, 2, 3, 4, 5, 6, 7, 8, 9, 10, 11, 12, 13, 14, 15, 16, 17, 18, 19, 20, 21, 22, 23, 24, 25 cell doublings or more. The stem cells may be grown for 25, 30, 35, 40, 45, 50, 55, 60, 65, 70, 75, 80, 85, 90, 95 or more cell doublings.

The stem cells may be cultured for more than 5, more than 10, more than 15, more than 20, more than 25, more than 30, more than 40, more than 45, more than 50, more than 100, more than 200, more than 500 or more than 800 passages, generations or cell doublings. The stem cells may be maintained for 100, 200, 500 or more passages, generations or cell doublings.

Growth and Productivity

The methods and compositions described here enable the production of stem cells in quantity.

The methods may enable exponential growth of stem cells in culture. The exponential growth may or may not be accompanied by a lag phase. The exponential growth may form part or a substantial period of the growth of the cells in culture. Methods of assessing exponential growth are known in the art.

For example the specific growth rate of the cells may conform to:

$$\mu = \frac{(\ln x1 - \ln x2)}{t1 - t2}$$

Where x=cell concentration and t=time.

The methods and compositions described here may enable greater productivity of cell growth compared to traditional, 2D culture methods (e.g., culture on plates). For example, the volumetric productivity of our methods may be $1 \times 10^6$ cells/well or more, such as $2.5 \times 10^6$ cells/well or more, for example 3, 4, 5, 6 or $7 \times 10^6$ cells/well or more. A well may have a diameter of about 3.5 cm or an area of about 9.5 cm$^2$. The volumetric productivity of our methods may be 1 million cells/ml or more, such as 2 million cells/ml or more, 2.5 million cells/ml or more, 3 million cells/ml or more, 3.5 million cells/ml, 1 million cells/ml or more, such as 4 million cells/ml or more, 4.5 million cells/ml or more, 5 million cells/ml or more.

Maintenance of Stem Cell Characteristics

The propagated stem cells may retain at least one characteristic of a mammalian, primate or human stem cell. The stem cells may retain the characteristic after one or more passages. They may do so after a plurality of passages. They may do so after the stated number of passages as described above.

The characteristic may comprise a morphological characteristic, immunohistochemical characteristic, a molecular biological characteristic, etc. The characteristic may comprise a biological activity.

Stem Cell Characteristics

The stem cells propagated by our methods may display any of the following stem cell characteristics.

Stem cells may display increased expression of Oct4 and/or SSEA-1 and/or TRA-1-60 and/or Mab84. Stem cells which are self-renewing may display a shortened cell cycle compared to stem cells which are not self-renewing.

Stem cells may display defined morphology. For example, in the two dimensions of a standard microscopic image, human embryonic stem cells display high nuclear/cytoplasmic ratios in the plane of the image, prominent nucleoli, and compact colony formation with poorly discernable cell junctions.

Stem cells may also be characterized by expressed cell markers as described in further detail below.

Expression of Pluripotency Markers

The biological activity that is retained may comprise expression of one or more pluripotency markers.

Stage-specific embryonic antigens (SSEA) are characteristic of certain embryonic cell types. Antibodies for SSEA markers are available from the Developmental Studies Hybridoma Bank (Bethesda Md.). Other useful markers are detectable using antibodies designated Tra-1-60 and Tra-1-81 (Andrews et al., Cell Lines from Human Germ Cell Tumors, in E. J. Robertson, 1987, supra). Human embryonic stem cells are typically SSEA-1 negative and SSEA-4 positive. hEG cells are typically SSEA-1 positive. Differentiation of primate pluripotent stem cells (pPS) cells in vitro results in the loss of SSEA-4, Tra-1-60, and Tra-1-81 expression and increased expression of SSEA-1. pPS cells can also be characterized by the presence of alkaline phosphatase activity, which can be detected by fixing the cells with 4% paraformaldehyde, and then developing with Vector Red as a substrate, as described by the manufacturer (Vector Laboratories, Burlingame Calif.).

Embryonic stem cells are also typically telomerase positive and OCT-4 positive. Telomerase activity can be determined using TRAP activity assay (Kim et al., Science 266:2011, 1997), using a commercially available kit (TRAPeze® XK Telomerase Detection Kit, Cat. s7707; Intergen Co., Purchase N.Y.; or TeloTAGGG™ Telomerase PCR ELISA plus, Cat. 2,013,89; Roche Diagnostics, Indianapolis). hTERT expression can also be evaluated at the mRNA level by RT-PCR. The LightCycler TeloTAGGG™ hTERT quantification kit (Cat. 3,012,344; Roche Diagnostics) is available commercially for research purposes.

Any one or more of these pluripotency markers, including FOXD3, PODXL, alkaline phosphatase, OCT-4, SSEA-4, TRA-1-60 and Mab84, etc, may be retained by the propagated stem cells.

Detection of markers may be achieved through any means known in the art, for example immunologically. Histochemical staining, flow cytometry (FACS), Western Blot, enzyme-linked immunoassay (ELISA), etc may be used.

Flow immunocytochemistry may be used to detect cell-surface markers. Immunohistochemistry (for example, of fixed cells or tissue sections) may be used for intracellular or cell-surface markers. Western blot analysis may be conducted on cellular extracts. Enzyme-linked immunoassay may be used for cellular extracts or products secreted into the medium.

For this purpose, antibodies to the pluripotency markers as available from commercial sources may be used.

Antibodies for the identification of stem cell markers including the Stage-Specific Embryonic Antigens 1 and 4 (SSEA-1 and SSEA-4) and Tumor Rejection Antigen 1-60 and 1-81 (TRA-1-60, TRA-1-81) may be obtained commercially, for example from Chemicon International, Inc (Temecula, Calif., USA). The immunological detection of these antigens using monoclonal antibodies has been widely used to characterize pluripotent stem cells (Shamblott M. J. et. al. (1998) PNAS 95: 13726-13731; Schuldiner M. et. al. (2000). PNAS 97: 11307-11312; Thomson J. A. et. al. (1998). Science 282: 1145-1147; Reubinoff B. E. et. al. (2000). Nature Biotechnology 18: 399-404; Henderson J. K. et. al. (2002). Stem Cells 20: 329-337; Pera M. et. al. (2000). J. Cell Science 113: 5-10).

The expression of tissue-specific gene products can also be detected at the mRNA level by Northern blot analysis, dot-blot hybridization analysis, or by reverse transcriptase initiated polymerase chain reaction (RT-PCR) using sequence-specific primers in standard amplification methods. Sequence data for the particular markers listed in this disclosure can be obtained from public databases such as GenBank (URL www.ncbi.nlm.nih.gov:80/entrez). See U.S. Pat. No. 5,843,780 for further details.

Substantially all of the propagated cells, or a substantial portion of them, may express the marker(s). For example, the percentage of cells that express the marker or markers may be 50% or more, 60% or more, 70% or more, 80% or more, 90% or more, 93% or more, 95% or more, 97% or more, 98% or more, 99% or more, or substantially 100%.

Cell Viability

The biological activity may comprise cell viability after the stated number of passages. Cell viability may be assayed in various ways, for example by Trypan Blue exclusion.

A protocol for vital staining follows. Place a suitable volume of a cell suspension (20-200 μL) in an appropriate tube, add an equal volume of 0.4% Trypan blue and gently mix, let stand for 5 minutes at room temperature. Place 10 μl of stained cells in a hemocytometer and count the number of viable (unstained) and dead (stained) cells. Calculate the average number of unstained cells in each quadrant, and multiply by $2 \times 10^4$ to find cells/ml. The percentage of viable cells is the number of viable cells divided by the number of dead and viable cells.

The viability of cells may be 50% or more, 60% or more, 70% or more, 80% or more, 90% or more, 93% or more, 95% or more, 97% or more, 98% or more, 99% or more, or substantially 100%.

Karyotype

The propagated stem cells may retain a normal karyotype during or after propagation. A "normal" karyotype is a karyotype that is identical, similar or substantially similar to a karyotype of a parent stem cell from which the stem cell is derived, or one which varies from it but not in any substantial manner. For example, there should not be any gross anomalies such as translocations, loss of chromosomes, deletions, etc.

Karyotype may be assessed by a number of methods, for example visually under optical microscopy. Karyotypes may be prepared and analyzed as described in McWhir et al. (2006), Hewitt et al. (2007), and Gallimore and Richardson (1973). Cells may also be karyotyped using a standard G-banding technique (available at many clinical diagnostics labs that provide routine karyotyping services, such as the Cytogenetics Lab at Oakland Calif.) and compared to published stem cell karyotypes.

All or a substantial portion of propagated cells may retain a normal karyotype. This proportion may be 50% or more, 60% or more, 70% or more, 80% or more, 90% or more, 93% or more, 95% or more, 97% or more, 98% or more, 99% or more, or substantially 100%.

Pluripotency

The propagated stem cells may retain the capacity to differentiate into all three cellular lineages, i.e., endoderm, ectoderm and mesoderm. Methods of induction of stem cells to differentiate into each of these lineages are known in the art and may be used to assay the capability of the propagated stem cells.

All or a substantial portion of propagated cells may retain this ability. This may be 50% or more, 60% or more, 70% or more, 80% or more, 90% or more, 93% or more, 95% or more, 97% or more, 98% or more, 99% or more, or substantially 100% of the propagated stem cells.

Co-Culture and Feeders

Our methods may comprise culturing stem cells in the presence or absence of co-culture. The term "co-culture" refers to a mixture of two or more different kinds of cells that are grown together, for example, stromal feeder cells. The two or more different kinds of cells may be grown on the same surfaces, such as particles or cell container surfaces, or on different surfaces. The different kinds of cells may be grown on different particles.

Feeder cells, as the term is used in this document, may mean cells which are used for or required for cultivation of cells of a different type. In the context of stem cell culture, feeder cells have the function of securing the survival, proliferation, and maintenance of ES-cell pluripotency. ES-cell pluripotency may be achieved by directly co-cultivating the feeder cells. Alternatively, or in addition, the feeder cells may be cultured in a medium to condition it. The conditioned medium may be used to culture the stem cells.

The inner surface of the container such as a culture dish may be coated with a feeder layer of mouse embryonic skin cells that have been treated so they will not divide. The feeder cells release nutrients into the culture medium which are required for ES cell growth. The stem cells growing on particles may therefore be grown in such coated containers.

The feeder cells may themselves be grown on particles. They may be seeded on particles in a similar way as described for stem cells. The stem cells to be propagated may be grown together with or separate from such feeder particles. The stem cells may therefore be grown on a layer on such feeder cell coated particles. On the other hand, the stem cells may be grown on separate particles. Any combinations of any of these arrangements are also possible, for example, a culture which comprises feeder cells grown on particles, particles with feeder cells and stem cells, and particles with stem cells growing. These combinations may be grown in containers with a feeder layer or without. The particles on which the feeder cells are grown may be either coated or not coated in a matrix coating.

Arrangements in which feeder cells are absent or not required are also possible. For example, the cells may be grown in medium conditioned by feeder cells or stem cells (Conditioned Media).

Media and Feeder Cells

Media for isolating and propagating pluripotent stem cells can have any of several different formulas, as long as the cells obtained have the desired characteristics, and can be propagated further.

Suitable sources are as follows: Dulbecco's modified Eagles medium (DMEM), Gibco#11965-092; Knockout Dulbecco's modified Eagles medium (KO DMEM), Gibco#10829-018; 200 mM L-glutamine, Gibco#15039-027; non-essential amino acid solution, Gibco 11140-050; beta-mercaptoethanol, Sigma#M7522; human recombinant basic fibroblast growth factor (bFGF), Gibco#13256-029. Exemplary serum-containing embryonic stem (ES) medium is made with 80% DMEM (typically KO DMEM), 20% defined fetal bovine serum (FBS) not heat inactivated, 0.1 mM non-essential amino acids, 1 mM L-glutamine, and 0.1 mM beta-mercaptoethanol. The medium is filtered and stored at 4 degrees C. for no longer than 2 weeks. Serum-free embryonic stem (ES) medium is made with 80% KO DMEM, 20% serum replacement, 0.1 mM non-essential amino acids, 1 mM L-glutamine, and 0.1 mM beta-mercaptoethanol. An effective serum replacement is Gibco#10828-028. The medium is filtered and stored at 4 degrees C. for no longer than 2 weeks. Just before use, human bFGF is added to a final concentration of 4 ng/mL (Bodnar et al., Geron Corp, International Patent Publication WO 99/20741). The media may comprise Knockout DMEM media (Invitrogen-Gibco, Grand Island, N.Y.), supplemented with 10% serum replacement media (Invitrogen-Gibco, Grand Island, N.Y.), 5 ng/ml FGF2 (Invitrogen-Gibco, Grand Island, N.Y.) and 5 ng/ml PDGF AB (Peprotech, Rocky Hill, N.J.).

Feeder cells (where used) may be propagated in mEF medium, containing 90% DMEM (Gibco#11965-092), 10% FBS (Hyclone#30071-03), and 2 mM glutamine. mEFs are propagated in T150 flasks (Corning#430825), splitting the cells 1:2 every other day with trypsin, keeping the cells subconfluent. To prepare the feeder cell layer, cells are irradiated at a dose to inhibit proliferation but permit synthesis of important factors that support human embryonic stem cells (about 4000 rads gamma irradiation). Six-well culture plates (such as Falcon#304) are coated by incubation at 37 degrees C. with 1 mL 0.5% gelatin per well overnight, and plated with 375,000 irradiated mEFs per well. Feeder cell layers are typically used 5 h to 4 days after plating. The medium is replaced with fresh human embryonic stem (hES) medium just before seeding pPS cells.

Conditions for culturing other stem cells are known, and can be optimized appropriately according to the cell type. Media and culture techniques for particular cell types referred to in the previous section are provided in the references cited.

Serum Free Media

The methods and compositions described here may include culture of stem cells in a serum-free medium.

The term "serum-free media" may comprise cell culture media which is free of serum proteins, e.g., fetal calf serum. Serum-free media are known in the art, and are described for example in U.S. Pat. Nos. 5,631,159 and 5,661,034. Serum-free media are commercially available from, for example, Gibco-BRL (Invitrogen).

The serum-free media may be protein free, in that it may lack proteins, hydrolysates, and components of unknown composition. The serum-free media may comprise chemically-defined media in which all components have a known chemical structure. Chemically-defined serum-free media is advantageous as it provides a completely defined system which eliminates variability, allows for improved reproducibility and more consistent performance, and decreases possibility of contamination by adventitious agents. It may also be free of animal derived components.

The serum-free media may comprise Knockout DMEM media (Invitrogen-Gibco, Grand Island, N.Y.).

The serum-free media may be supplemented with one or more components, such as serum replacement media, at a concentration of for example, 5%, 10%, 15%, etc. The serum-free media may be supplemented with 10% serum replacement media from Invitrogen-Gibco (Grand Island, N.Y.).

The serum-free medium in which the dissociated or disaggregated embryonic stem cells are cultured may comprise one or more growth factors. A number of growth factors are known in the art, including FGF2, IGF-2, Noggin, Activin A, TGF beta 1, HRG1 beta, LIF, S1P, PDGF, BAFF, April, SCF, Flt-3 ligand, Wnt3A and others. The growth factor(s) may be used at any suitable concentration such as between 1 pg/ml to 500 ng/ml.

Media Supplements

Culture media may be supplemented with one or more additives. For example, these may be selected from one or more of: a lipid mixture, Bovine Serum Albumin (e.g. 0.1% BSA), hydrolysate of soybean protein.

Stem Cells

As used in this document, the term "stem cell" refers to a cell that on division faces two developmental options: the daughter cells can be identical to the original cell (self-renewal) or they may be the progenitors of more specialised cell types (differentiation). The stem cell is therefore capable of adopting one or other pathway (a further pathway exists in which one of each cell type can be formed). Stem cells are therefore cells which are not terminally differentiated and are able to produce cells of other types.

Stem cells as referred to in this document may include totipotent stem cells, pluripotent stem cells, and multipotent stem cells.

In general, reference herein to stem cells (plural) may include the singular (stem cell). In particular, methods of culturing and differentiating stem cells may include single cell and aggregate culturing techniques.

In the present invention stem cell cultures may be of aggregates or single cells.

Totipotent Stem Cells

The term "totipotent" cell refers to a cell which has the potential to become any cell type in the adult body, or any cell of the extraembryonic membranes (e.g., placenta). Thus, the only totipotent cells are the fertilized egg and the first 4 or so cells produced by its cleavage.

Pluripotent Stem Cells

"Pluripotent stem cells" are true stem cells, with the potential to make any differentiated cell in the body. However, they cannot contribute to making the extraembryonic membranes which are derived from the trophoblast. Several types of pluripotent stem cells have been found.

Embryonic Stem Cells

Embryonic Stem (ES) cells may be isolated from the inner cell mass (ICM) of the blastocyst, which is the stage of embryonic development when implantation occurs.

Embryonic Germ Cells

Embryonic Germ (EG) cells may be isolated from the precursor to the gonads in aborted fetuses.

Embryonic Carcinoma Cells

Embryonic Carcinoma (EC) cells may be isolated from teratocarcinomas, a tumor that occasionally occurs in a gonad of a fetus. Unlike the first two, they are usually aneuploid. All three of these types of pluripotent stem cells can only be isolated from embryonic or fetal tissue and can be grown in culture. Methods are known in the art which prevent these pluripotent cells from differentiating.

Adult Stem Cells

Adult stem cells comprise a wide variety of types including neuronal, skin and the blood forming stem cells which are the active component in bone marrow transplantation. These latter stem cell types are also the principal feature of umbilical cord-derived stem cells. Adult stem cells can mature both in the laboratory and in the body into functional, more specialised cell types although the exact number of cell types is limited by the type of stem cell chosen. For example, adult stem cells may be mesenchymal stem cells, haematopoietic stem cells, mammary stem cells, endothelial stem cells, or neural stem cells. Adult stem cells may be multipotent.

Multipotent Stem Cells

Multipotent stem cells are true stem cells but can only differentiate into a limited number of types. For example, the bone marrow contains multipotent stem cells that give rise to all the cells of the blood but not to other types of cells. Multipotent stem cells are found in adult animals. It is thought that every organ in the body (brain, liver) contains them where they can replace dead or damaged cells.

Methods of characterising stem cells are known in the art, and include the use of standard assay methods such as clonal assay, flow cytometry, long-term culture and molecular biological techniques e.g. PCR, RT-PCR and Southern blotting.

In addition to morphological differences, human and murine pluripotent stem cells differ in their expression of a number of cell surface antigens (stem cell markers). Markers for stem cells and methods of their detection are described elsewhere in this document (under "Maintenance of Stem Cell Characteristics").

Sources of Stem Cells

U.S. Pat. No. 5,851,832 reports multipotent neural stem cells obtained from brain tissue. U.S. Pat. No. 5,766,948 reports producing neuroblasts from newborn cerebral hemispheres. U.S. Pat. Nos. 5,654,183 and 5,849,553 report the use of mammalian neural crest stem cells.

U.S. Pat. No. 6,040,180 reports in vitro generation of differentiated neurons from cultures of mammalian multipotential CNS stem cells. WO 98/50526 and WO 99/01159 report generation and isolation of neuroepithelial stem cells, oligodendrocyte-astrocyte precursors, and lineage-restricted neuronal precursors.

U.S. Pat. No. 5,968,829 reports neural stem cells obtained from embryonic forebrain and cultured with a medium comprising glucose, transferrin, insulin, selenium, progesterone, and several other growth factors.

Primary liver cell cultures can be obtained from human biopsy or surgically excised tissue by perfusion with an appropriate combination of collagenase and hyaluronidase. Alternatively, EP 0 953 633 A1 reports isolating liver cells by preparing minced human liver tissue, resuspending concentrated tissue cells in a growth medium and expanding the cells in culture. The growth medium comprises glucose, insulin, transferrin, T3, FCS, and various tissue extracts that allow the hepatocytes to grow without malignant transformation.

The cells in the liver are thought to contain specialized cells including liver parenchymal cells, Kupffer cells, sinusoidal endothelium, and bile duct epithelium, and also precursor cells (referred to as "hepatoblasts" or "oval cells") that have the capacity to differentiate into both mature hepatocytes or biliary epithelial cells (L. E. Rogler, Am. J. Pathol. 150:591, 1997; M. Alison, Current Opin. Cell Biol. 10:710, 1998; Lazaro et al., Cancer Res. 58:514, 1998).

U.S. Pat. No. 5,192,553 reports methods for isolating human neonatal or fetal hematopoietic stem or progenitor cells. U.S. Pat. No. 5,716,827 reports human hematopoietic cells that are Thy-1 positive progenitors, and appropriate growth media to regenerate them in vitro. U.S. Pat. No. 5,635,387 reports a method and device for culturing human hematopoietic cells and their precursors. U.S. Pat. No. 6,015,554 describes a method of reconstituting human lymphoid and dendritic cells.

U.S. Pat. No. 5,486,359 reports homogeneous populations of human mesenchymal stem cells that can differentiate into cells of more than one connective tissue type, such as bone, cartilage, tendon, ligament, and dermis. They are obtained from bone marrow or periosteum. Also reported are culture conditions used to expand mesenchymal stem cells. WO 99/01145 reports human mesenchymal stem cells isolated from peripheral blood of individuals treated with growth factors such as G-CSF or GM-CSF. WO 00/53795 reports adipose-derived stem cells and lattices, substantially free of adipocytes and red cells. These cells reportedly can be expanded and cultured to produce hormones and conditioned culture media.

Stem cells of any vertebrate species can be used. Included are stem cells from humans; as well as non-human primates, domestic animals, livestock, and other non-human mammals such as rodents, mice, rats, etc.

Amongst the stem cells suitable for use in the methods and compositions described here are primate or human pluripotent stem cells derived from tissue formed after gestation, such as a blastocyst, or fetal or embryonic tissue taken any time during gestation. Non-limiting examples are primary cultures or established lines of embryonic stem cells.

Embryonic Stem Cells

Embryonic stem cells may be isolated from blastocysts of members of primate species (Thomson et al., Proc. Natl. Acad. Sci. USA 92:7844, 1995). Human embryonic stem (hES) cells can be prepared from human blastocyst cells using the techniques described by Thomson et al. (U.S. Pat. No. 5,843,780; Science 282:1145, 1998; Curr. Top. Dev. Biol. 38:133 ff., 1998) and Reubinoff et al, Nature Biotech. 18:399, 2000.

Briefly, human blastocysts may be obtained from human in vivo preimplantation embryos. Alternatively, in vitro fertilized (IVF) embryos can be used, or one cell human embryos can be expanded to the blastocyst stage (Bongso et al., Hum Reprod 4: 706, 1989). Human embryos are cultured to the blastocyst stage in G1.2 and G2.2 medium (Gardner et al., Fertil. Steril. 69:84, 1998). Blastocysts that develop are selected for embryonic stem cell isolation. The zona pellucida is removed from blastocysts by brief exposure to pronase (Sigma). The inner cell masses are isolated by immunosurgery, in which blastocysts are exposed to a 1:50 dilution of rabbit anti-human spleen cell antiserum for 30 minutes, then washed for 5 minutes three times in DMEM, and exposed to a 1:5 dilution of Guinea pig complement (Gibco) for 3 minutes (see Solter et al., Proc. Natl. Acad. Sci. USA 72:5099, 1975). After two further washes in DMEM, lysed trophectoderm cells are removed from the intact inner cell mass (ICM) by gentle pipetting, and the ICM plated on mEF feeder layers.

After 9 to 15 days, inner cell mass-derived outgrowths are dissociated into clumps either by exposure to calcium and magnesium-free phosphate-buffered saline (PBS) with 1 mM EDTA, by exposure to dispase or trypsin, or by mechanical dissociation with a micropipette; and then replated on mEF in fresh medium. Dissociated cells are replated on mEF feeder layers in fresh embryonic stem (ES) medium, and observed for colony formation. Colonies demonstrating undifferentiated morphology are individually selected by micropipette, mechanically dissociated into clumps, and replated. Embryonic stem cell-like morphology is characterized as compact colonies with apparently high nucleus to cytoplasm ratio and prominent nucleoli. Resulting embryonic stem cells are then routinely split every 1-2 weeks by brief trypsinization, exposure to Dulbecco's PBS (without calcium or magnesium and with 2 mM EDTA), exposure to type IV collagenase (about. 200 U/mL; Gibco) or by selection of individual colonies by micropipette. Clump sizes of about 50 to 100 cells are optimal.

Embryonic Germ Cells

Human Embryonic Germ (hEG) cells may be prepared from primordial germ cells present in human fetal material taken about 8-11 weeks after the last menstrual period. Suitable preparation methods are described in Shamblott et al., Proc. Natl. Acad. Sci. USA 95:13726, 1998 and U.S. Pat. No. 6,090,622.

Briefly, genital ridges are rinsed with isotonic buffer, then placed into 0.1 mL 0.05% trypsin/0.53 mM sodium EDTA solution (BRL) and cut into <1 $mm^3$ chunks. The tissue is then pipetted through a 100/µL tip to further disaggregate the cells. It is incubated at 37 degrees C. for about 5 min, then about 3.5 mL EG growth medium is added. EG growth medium is DMEM, 4500 mg/L D-glucose, 2200 mg/L mM sodium bicarbonate; 15% embryonic stem (ES) qualified fetal calf serum (BRL); 2 mM glutamine (BRL); 1 mM sodium pyruvate (BRL); 1000-2000 U/mL human recombinant leukemia inhibitory factor (LIF, Genzyme); 1-2 ng/ml human recombinant basic fibroblast growth factor (bFGF, Genzyme); and 10 µM forskolin (in 10% DMSO). In an alternative approach, EG cells are isolated using hyaluronidase/collagenase/DNAse. Gonadal anlagen or genital ridges with mesenteries are dissected from fetal material, the genital ridges are rinsed in PBS, then placed in 0.1 ml HCD digestion solution (0.01% hyaluronidase type V, 0.002% DNAse I, 0.1% collagenase type IV, all from Sigma prepared in EG growth medium). Tissue is minced and incubated 1 h or overnight at 37 degrees C., resuspended in 1-3 mL of EG growth medium, and plated onto a feeder layer.

Ninety-six well tissue culture plates are prepared with a sub-confluent layer of feeder cells cultured for 3 days in modified EG growth medium free of LIF, bFGF or forskolin, inactivated with 5000 rad γ-irradiation. Suitable feeders are STO cells (ATCC Accession No. CRL 1503). 0.2 mL of primary germ cell (PGC) suspension is added to each of the wells. The first passage is conducted after 7-10 days in EG growth medium, transferring each well to one well of a 24-well culture dish previously prepared with irradiated STO mouse fibroblasts. The cells are cultured with daily replacement of medium until cell morphology consistent with EG cells are observed, typically after 7-30 days or 1-4 passages.

Induced Pluripotent Stem Cells

The methods and compositions described here may be used for the propagation of induced pluripotent stem cells.

Induced pluripotent stem cells, commonly abbreviated as iPS cells or iPSCs, are a type of pluripotent stem cell artificially derived from a non-pluripotent cell, typically an adult somatic cell, for example fibroblasts, lung or B cells, by inserting certain genes.

iPS cells are reviewed and discussed in Takahashi, K. & Yamanaka (Induction of pluripotent stem cells from mouse embryonic and adult fibroblast cultures by defined factors. Cell 2006; 126:663-676), Yamanaka S, et. al. (Yamanaka S, et al. Induction of Pluripotent Stem Cells from Adult Human Fibroblasts by Defined Factors. doi:10.1016/j.cell.2007.11.019, and Yamanaka S, et. al. Generation of germline-competent induced pluripotent stem cells. Nature 2007; 448:313-7), Wernig M, et. al. (In vitro reprogramming of fibroblasts into a pluripotent ES-cell-like state. Nature 2007; 448:318-24), Maherali N, et. al. (Directly reprogrammed fibroblasts show global epigenetic remodeling and widespread tissue contribution. Cell Stem Cell 2007; 1:55-70) and Thomson J A, Yu J, et al. (Induced Pluripotent Stem Cell Lines Derived from Human Somatic Cells. Science DOI: 10.1126/science.1151526) and Takahashi et al., (Induction of pluripotent stem cells from adult human fibroblasts by defined factors. Cell. (2007) 131(5):861-72), all incorporated herein by reference iPS cells are typically derived by transfection of certain stem cell-associated genes into non-pluripotent cells, such as adult fibroblasts. Transfection is typically achieved through viral vectors, such as retroviruses. Transfected genes include the master transcriptional regulators Oct-3/4 (Pouf51) and Sox2, although it is suggested that other genes enhance the efficiency of induction. After 3-4 weeks, small numbers of transfected cells begin to become morphologically and biochemically similar to pluripotent stem cells, and are typically isolated through morphological selection, doubling time, or through a reporter gene and antibiotic infection.

Sources of Pluripotent Cells

Some aspects and embodiments of the present invention are concerned with the use of pluripotent cells. Embryonic stem cells and induced pluripotent stem cells are described as examples of such cells.

Embryonic stem cells have traditionally been derived from the inner cell mass (ICM) of blastocyst stage embryos (Evans, M. J., and Kaufman, M. H. (1981). Establishment in culture of pluripotential cells from mouse embryos. Nature 292, 154-156. Martin, G. R. (1981). Isolation of a pluripotent cell line from early mouse embryos cultured in medium conditioned by teratocarcinoma stem cells. Proc. Natl. Acad. Sci. USA 78, 7634-7638. Thomson, J. A., Itskovitz-Eldor, J., Shapiro, S. S., Waknitz, M. A., Swiergiel, J. J., Marshall, V. S., and Jones, J. M. (1998). Embryonic stem cell lines derived from human blastocysts. Science 282, 1145-1147). In isolating embryonic stem cells these methods may cause the destruction of the embryo.

Several methods have now been provided for the isolation of pluripotent stem cells that do not lead to the destruction of an embryo, e.g. by transforming adult somatic cells or germ cells. These methods include:

1. Reprogramming by nuclear transfer. This technique involves the transfer of a nucleus from a somatic cell into an oocyte or zygote. In some situations this may lead to the creation of an animal-human hybrid cell. For example, cells may be created by the fusion of a human somatic cell with an animal oocyte or zygote or fusion of a human oocyte or zygote with an animal somatic cell.

2. Reprogramming by fusion with embryonic stem cells. This technique involves the fusion of a somatic cell with an embryonic stem cell. This technique may also lead to the creation of animal-human hybrid cells, as in 1 above.

3. Spontaneous re-programming by culture. This technique involves the generation of pluripotent cells from non-pluripotent cells after long term culture. For example, pluripotent embryonic germ (EG) cells have been generated by long-term culture of primordial germ cells (PGC) (Matsui et al., Derivation of pluripotential embryonic stem cells from murine primordial germ cells in culture. Cell 70, 841-847, 1992, incorporated herein by reference). The development of pluripotent stem cells after prolonged culture of bone marrow-derived cells has also been reported (Jiang et al., Pluripotency of mesenchymal stem cells derived from adult marrow. Nature 418, 41-49, 2002, incorporated herein by reference). They designated these cells multipotent adult progenitor cells (MAPCs). Shinohara et al also demonstrated that pluripotent stem cells can be generated during the course of culture of germline stem (GS) cells from neonate mouse testes, which they designated multipotent germline stem (mGS) cells (Kanatsu-Shinohara et al., Generation of pluripotent stem cells from neonatal mouse testis. Cell 119, 1001-1012, 2004, incorporated herein by reference).

4. Reprogramming by defined factors. For example the generation of IFS cells by the retrovirus-mediated introduction of transcription factors (such as Oct-3/4, Sox2, c-Myc, and KLF4) into mouse embryonic or adult fibroblasts, e.g. as described above. Kaji et al (Virus-free induction of pluripotency and subsequent excision of reprogramming factors. Nature. Online publication 1 Mar. 2009, incorporated herein by reference) also describe the non-viral transfection of a single multiprotein expression vector, which comprises the coding sequences of c-Myc, Klf4, Oct4 and Sox2 linked with 2A peptides, that can reprogram both mouse and human fibroblasts. iPS cells produced with this non-viral vector show robust expression of pluripotency markers, indicating a reprogrammed state confirmed functionally by in vitro differentiation assays and formation of adult chimaeric mice. They succeeded in establishing reprogrammed human cell lines from embryonic fibroblasts with robust expression of pluripotency markers.

Methods 1-4 are described and discussed by Shinya Yamanaka in Strategies and New Developments in the Generation of Patient-Specific Pluripotent Stem Cells (Cell Stem Cell 1, July 2007 *a*2007 Elsevier Inc), incorporated herein by reference.

5. Derivation of hESC lines from single blastomeres or biopsied blastomeres. See Klimanskaya I, Chung Y, Becker S, Lu S J, Lanza R. Human embryonic stem cell lines derived from single blastomeres. Nature 2006; 444:512, Lei et al Xeno-free derivation and culture of human embryonic stem cells: current status, problems and challenges. Cell Research (2007) 17:682-688, Chung Y, Klimanskaya I, Becker S, et al. Embryonic and extraembryonic stem cell lines derived from single mouse blastomeres. Nature. 2006; 439:216-219. Klimanskaya I, Chung Y, Becker S, et al. Human embryonic stem cell lines derived from single blastomeres. Nature. 2006; 444: 481-485. Chung Y, Klimanskaya I, Becker S, et al. Human embryonic stem cell lines generated without embryo destruction. Cell Stem Cell. 2008; 2:113-117 and Dusko 111c et al (Derivation of human embryonic stem cell lines from biopsied blastomeres on human feeders with a minimal exposure to xenomaterials. Stem Cells And Development—paper in pre-publication), all incorporated herein by reference.

6. hESC lines obtained from arrested embryos which stopped cleavage and failed to develop to morula and blastocysts in vitro. See Zhang X, Stojkovic P, Przyborski S, et al. Derivation of human embryonic stem cells from developing and arrested embryos. Stem Cells 2006; 24:2669-2676 and Lei et al Xeno-free derivation and culture of human embryonic stem cells: current status, problems and challenges. Cell Research (2007) 17:682-688, both incorporated herein by reference.

7. Parthogenesis (or Parthenogenesis). This technique involves chemical or electrical stimulation of an unfertilised egg so as to cause it to develop into a blastomere from which embryonic stem cells may be derived. For example, see Lin et al. Multilineage potential of homozygous stem cells derived from metaphase II oocytes. Stem Cells. 2003; 21(2):152-61 who employed the chemical activation of nonfertilized metaphase II oocytes to produce stem cells.

8. Stem cells of fetal origin. These cells lie between embryonic and adult stem cells in terms of potentiality and may be used to derive pluripotent or multipotent cells. Human umbilical-cord-derived fetal mesenchymal stem cells (UC fMSCs) expressing markers of pluripotency (including Nanog, Oct-4, Sox-2, Rex-1, SSEA-3, SSEA-4, Tra-1-60, and Tra-1-81, minimal evidence of senescence as shown by β-galactosidase staining, and the consistent expression of telomerase activity) have been successfully derived by Chris H. Jo et al (Fetal mesenchymal stem cells derived from human umbilical cord sustain primitive characteristics during extensive expansion. Cell Tissue Res (2008) 334:423-433, incorporated herein by reference). Winston Costa Pereira et at (Reproducible methodology for the isolation of mesenchymal stem cells from human umbilical cord and its potential for cardiomyocyte generation J Tissue Eng Regen Med 2008; 2: 394-399, incorporated herein by reference) isolated a pure population of mesenchymal stem cells from Wharton's jelly of the human umbilical cord. Mesenchymal stem cells derived from Wharton's jelly are also reviewed in Troyer & Weiss (Concise Review: Wharton's Jelly-Derived Cells Are a primitive Stromal Cell Population. Stem Cells 2008:26:591-599, incorporated herein by reference). Kim et al (Ex vivo characteristics of human amniotic membrane-derived stem cells. Cloning Stem Cells 2007 Winter; 9(4):581-94, incorporated herein by reference) succeeded in isolating human amniotic membrane-derived mesenchymal cells from human amniotic membranes. Umbilical cord is a tissue that is normally discarded and stem cells derived from this tissue have tended not to attract moral or ethical objection.

The present invention includes the use of pluripotent or multipotent stem cells obtained from any of these sources or created by any of these methods. In some embodiments, the pluripotent or multipotent cells used in the methods of the present invention have been obtained by a method that does not cause the destruction of an embryo. More preferably in some embodiments, the pluripotent or multipotent cells used in the methods of the present invention have been obtained by a method that does not cause the destruction of a human or mammalian embryo. As such, methods of the invention may be performed using cells that have not been prepared exclusively by a method which necessarily involves the destruction of human embryos from which those cells may be derived. This optional limitation is specifically intended to take account of Decision G0002/06 of 25 Nov. 2008 of the Enlarged Board of Appeal of the European Patent Office.

Differentiation/Embryoid Bodies

The cultured stem cells may be differentiated into any suitable cell type by using differentiation techniques known to those of skill in the art.

We describe a process for producing differentiated cells, the method comprising propagating a stem cell by a method as described herein, and then differentiating the stem cell in accordance with known techniques. For example, we provide for methods of differentiating to ectoderm, mesoderm and endoderm, as well as to cardiomyocytes, adipocytes, chondrocytes and osteocytes, etc. We further provide embryoid bodies and differentiated cells obtainable by such methods. Cell lines made from such stem cells and differentiated cells are also provided.

Methods of differentiating stem cells are known in the art and are described in for example Itskovitz-Eldor (J Itskovitz-Eldor, M Schuldiner, D Karsenti, A Eden, O Yanuka, M Amit, H Soreq, N Benvenisty. Differentiation of human embryonic stem cells into embryoid bodies compromising the three embryonic germ layers. Mol. Med. 2000 February; 6 (2):88-95) and Graichen et al (2007), Kroon et at (2008) and Hay et at (2008. Highly efficient differentiation of hESCs to functional hepatic endoderm requires ActivinA and Wnt3a signalling. PNAS Vol. 105. No. 34 12310-12306), WO 2007/030870, WO 2007/070964, Niebrugge et at (Generation of Human Embryonic Stem Cell-Derived Mesoderm and Cardiac Cells Using Size-Specified Aggregates in an Oxygen-Controlled Bioreactor. Biotechnology and Bioengineering. Vol. 102, no. 2, Feb. 1, 2009), R Passier et al. (Serum free media in cocultures (FBS inhibits cardiomyocytes differentiation). Curr Opin Biotechnol. 2005 October; 16(5):498-502. Review. Stem Cells. 2005 June-July; 23(6):772-80), P W Burridge et al. (Defined Medium with polyvinyl alcohol (PVA), Activin A and bFGF. Stem Cells. 2007 April; 25(4): 929-38. Epub 2006 Dec. 21), M A Laflamme et al. (Culture sequentially supplemented with Activin A for 24 h, and BMP 4 for 4 days. Nat. Biotechnol. 2007 September; 25(9):1015-24. Epub 2007 Aug. 26), L Yang et al. (Defined medium supplemented with BMP4 (1 day), BMP4, Activin A and bFGF (days 1-4), Activin A and bFGF (days 4-8), and DKK1 and VEGF. Nature. 2008 May 22; 453(7194):524-8. Epub 2008 Apr. 23), and X Q Xu et al. (SB203580 (p38 MAP kinase inhibitor) PGI2 (prostaglandin member accumulated in END2-CM). Differentiation. 2008 November; 76(9):958-70. Epub 2008 Jun. 13).

The cultured stem cells may also be used for the formation of embryoid bodies. Embryoid bodies, and methods for making them, are known in the art. The term "embryoid body" refers to spheroid colonies seen in culture produced by the growth of embryonic stem cells in suspension. Embryoid bodies are of mixed cell types, and the distribution and timing of the appearance of specific cell types corresponds to that observed within the embryo. Embryoid bodies may be generated by plating out embryonic stem cells onto media such as semi-solid media. Methylcellulose media may be used as described in Lim et al, Blood. 1997; 90:1291-1299.

Embryonic stem cells may be induced to form embryoid bodies, for example using the methods described in ltskovitz-Eldor (2000). The embryoid bodies contain cells of all three embryonic germ layers.

The embryoid bodies may be further induced to differentiate into different lineages for example by exposure to the appropriate induction factor or an environmental change. Graichen et at (2007) describes the formation of cardiomyocytes from human embryonic stem cells by manipulation of the p38MAP kinase pathway. Graichen demonstrates induction of cardiomyocyte formation from stem cells by exposure to a specific inhibitor of p38 MAP kinase such as SB203580 at less than 10 micromolar.

Differentiated cells may be employed for any suitable purpose, such as regenerative therapy, as known in the art.

Stem cells obtained through culture methods and techniques according to this invention may be used to differentiate into another cell type for use in a method of medical treatment. Thus, the differentiated cell type may be derived from a stem cell obtained by the culture methods and techniques described herein which has subsequently been permitted to differentiate. The differentiated cell type may be considered as a product of a stem cell obtained by the culture methods and techniques described herein which has subsequently been permitted to differentiate. Pharmaceutical compositions may be provided comprising such differentiated cells, optionally together with a pharmaceutically acceptable carrier, adjuvant or diluent. Such pharmaceutical composition may be useful in a method of medical treatment.

Differentiation on Microcarriers

In accordance with our earlier findings (see US patent applications U.S. 61/069,694 filed 17 Mar. 2009, U.S. 61/110,256 filed 31 Oct. 2008, U.S. 61/148,064 filed 29 Jan. 2009 and U.S. 61/155,940 filed 27 Feb. 2009) stem cells, particularly embryonic stem cells and iPS, may be induced to differentiate during suspension culture on microcarriers.

Embryonic stem cells may be induced to differentiate into the three primary germ layers: ectoderm, endoderm and mesoderm and their derivatives. Embryonic stem cells may be induced to form embryoid bodies. A range of cell types or tissues may therefore be obtained, for example cardiomyocytes, cardiac mesoderm, hepatocytes, hepatic endoderm, pancreatic islet cells, pancreatic endoderm, insulin producing cells, neural tissue, neuroectoderm, epidermal tissue, surface ectoderm, bone, cartilage, muscle, ligament, tendon or other connective tissue.

Methods for the differentiation of stem cells and the formation of embryoid bodies are described above, and are applicable to the differentiation of stem cells in microcarrier culture.

Methods of differentiation of stem cells during microcarrier culture may r be carried out in the presence or absence of a ROCK inhibitor. For example, stem cells propagated on microcarriers in the presence of a ROCK inhibitor in accordance with the present invention may be induced to differentiate by exposing the cells (and microcarriers) to culture conditions that will induce differentiation. Such culture conditions may include the continued exposure of the stem cells to a ROCK inhibitor (which may be the same or different to the ROCK inhibitor used for propagation of the cells), or the culture conditions may exclude a ROCK inhibitor.

Methods of differentiation of stem cells during microcarrier culture may require the microcarrier to be uncoated or coated in a matrix coating as described above. For example, suitable coatings may include one or more of: Matrigel, Laminin, Fibronectin, Vitronectin, Hyaluronic Acid.

Methods of differentiation of stem cells during microcarrier culture may include the addition of supplements to the culture media. For example, supplements may include Bovine Serum Albumin, Lipids or Hy-Soy (Sigma-Aldrich—this is an enzymatic hydrolysate of soybean protein).

Methods of differentiation of stem cells during microcarrier culture may involve an initial culture and propagation of the stem cells in either 2D culture or in 3D suspension microcarrier culture followed by induction of differentiation during microcarrier culture.

Uses

The methods and compositions described here may be employed for various means.

For example, the particles described here may be provided as research tools or lab reagents for simpler culture of stem cells. They may be used for expansion of undifferentiated stem cells on microcarriers for generating differentiated cells. This could be developed into a contract manufacturing capability. Stem cells may be expanded and optionally differentiated for use in drug testing. The particles or microcarriers may be labelled for combinatorial differentiation of stem cells in different media conditions. Stem cells propagated by the methods described here may be used for a variety of commercially important research, diagnostic, and therapeutic purposes. The stem cells may be used directly for these purposes, or may be differentiated into any chosen cell type using methods known in the art. Progenitor cells may also be derived from the stem cells. The differentiated cells or progenitor cells, or both, may be used in place of, or in combination with, the stem cells for the same purposes. Thus, any use described in this document for stem cells applies equally to progenitor cells and differentiated cells derived from the stem cells. Similarly, any uses of differentiated cells will equally apply to those stem cells for which they are progenitors, or progenitor cells.

The uses for stem cells, etc are generally well known in the art, but will be described briefly here.

Therapeutic Uses

The methods and compositions described here may be used to propagate stem cells for regenerative therapy. Stem cells may be expanded and directly administered into a patient. They may be used for the repopulation of damaged tissue following trauma. Embryonic stem cells may be used directly, or used to generate ectodermal, mesodermal or endodermal progenitor cell populations, for regenerative therapy. Progenitor cells may be made by ex vivo expansion or directly administered into a patient. They may also be used for the re-population of damaged tissue following trauma.

Thus, hematopoietic progenitor cells may be used for bone marrow replacement, while cardiac progenitor cells may be used for cardiac failure patients. Skin progenitor cells may be employed for growing skin grafts for patients and endothelial progenitor cells for endothelization of artificial prosthetics such as stents or artificial hearts.

Embryonic stem cells may be used as sources of ectodermal, mesodermal or endodermal progenitor cells for the treatment of degenerative diseases such as diabetes, Alzheimer's disease, Parkinson's disease, etc. Embryonic stem cells may be used as sources of mesodermal or endodermal progenitors for NK or dendritic cells for immunotherapy for cancer.

The methods and compositions described here enable the production of ectodermal, mesodermal or endodermal progenitor cells, which may of course be made to further differentiate using methods known in the art to terminally differentiated cell types.

Thus, any uses of terminally differentiated cells will equally attach to those ectodermal, mesodermal or endodermal progenitor cells (or stem cells) for which they are sources.

Stem cells, ectodermal, mesodermal or endodermal progenitor cells and differentiated cells produced by the methods and compositions described here may be used for, or for the preparation of a pharmaceutical composition for, the treatment of a disease. Such disease may comprise a disease treatable by regenerative therapy, including cardiac failure, bone marrow disease, skin disease, burns, degenerative disease such as diabetes, Alzheimer's disease, Parkinson's disease, etc and cancer.

Libraries

For example, populations of undifferentiated and differentiated cells may be used to prepare antibodies and cDNA libraries that are specific for the differentiated phenotype. General techniques used in raising, purifying and modifying antibodies, and their use in immunoassays and immunoisolation methods are described in Handbook of Experimental Immunology (Weir & Blackwell, eds.); Current Protocols in Immunology (Coligan et al., eds.); and Methods of Immunological Analysis (Masseyeff et al., eds., Weinheim: VCH Verlags GmbH). General techniques involved in preparation of mRNA and cDNA libraries are described in RNA Methodologies: A Laboratory Guide for Isolation and Characterization (R. E. Farrell, Academic Press, 1998); cDNA Library Protocols (Cowell & Austin, eds., Humana Press); and Functional Genomics (Hunt & Livesey, eds., 2000). Relatively homogeneous cell populations are particularly suited for use in drug screening and therapeutic applications.

Drug Screening

Stem cells and differentiated cells may also be used to screen for factors (such as solvents, small molecule drugs, peptides, polynucleotides, and the like) or environmental conditions (such as culture conditions or manipulation) that affect the characteristics of stem cells or differentiated cells.

Stem cells may be used to screen for factors that promote pluripotency, or differentiation. In some applications, differentiated cells are used to screen factors that promote maturation, or promote proliferation and maintenance of such cells in long-term culture. For example, candidate maturation factors or growth factors are tested by adding them to cells in different wells, and then determining any phenotypic change that results, according to desirable criteria for further culture and use of the cells.

Particular screening applications relate to the testing of pharmaceutical compounds in drug research. The reader is referred generally to the standard textbook "In vitro Methods in Pharmaceutical Research", Academic Press, 1997, and U.S. Pat. No. 5,030,015), as well as the general description of drug screens elsewhere in this document. Assessment of the activity of candidate pharmaceutical compounds generally involves combining the stem cells or differentiated cells with the candidate compound, determining any change in the morphology, marker phenotype, or metabolic activity of the cells that is attributable to the compound (compared with untreated cells or cells treated with an inert compound), and then correlating the effect of the compound with the observed change.

The screening may be done, for example, either because the compound is designed to have a pharmacological effect on certain cell types, or because a compound designed to have effects elsewhere may have unintended side effects. Two or more drugs can be tested in combination (by combining with the cells either simultaneously or sequentially), to detect possible drug-drug interaction effects. In some applications, compounds are screened initially for potential toxicity (Castell et al., pp. 375-410 in "In vitro Methods in Pharmaceutical Research," Academic Press, 1997). Cytotoxicity can be determined in the first instance by the effect on cell viability, survival, morphology, and expression or release of certain markers, receptors or enzymes. Effects of a drug on chromosomal DNA can be determined by measuring DNA synthesis or repair. [$^3$H]thymidine or BrdU incorporation, especially at unscheduled times in the cell cycle, or above the level required for cell replication, is consistent with a drug effect. Unwanted effects can also include unusual rates of sister chromatid exchange, determined by metaphase spread. The reader is referred to A. Vickers (PP 375-410 in "In vitro Methods in Pharmaceutical Research," Academic Press, 1997) for further elaboration.

Tissue Regeneration

Stem cells propagated according to the methods and compositions described here (and differentiated cells derived therefrom) may be used for therapy, for example tissue reconstitution or regeneration in an individual patient in need thereof. The cells may be administered in a manner that permits them to graft to the intended tissue site and reconstitute or regenerate the functionally deficient area.

Propagated stem cells or differentiated cells derived therefrom may be used for tissue engineering, such as for the growing of skin grafts. They may be used for the bioengineering of artificial organs or tissues, or for prosthetics, such as stents.

Differentiated cells may also be used for tissue reconstitution or regeneration in a human patient in need thereof. The cells are administered in a manner that permits them to graft to the intended tissue site and reconstitute or regenerate the functionally deficient area. For example, the methods and compositions described here may be used to modulate the differentiation of stem cells. Differentiated cells may be used for tissue engineering, such as for the growing of skin grafts. Modulation of stem cell differentiation may be used for the bioengineering of artificial organs or tissues, or for prosthetics, such as stents.

In another example, neural stem cells are transplanted directly into parenchymal or intrathecal sites of the central nervous system, according to the disease being treated. Grafts are done using single cell suspension or small aggregates at a density of 25,000-500,000 cells per mu.L (U.S. Pat. No. 5,968,829). The efficacy of neural cell transplants can be assessed in a rat model for acutely injured spinal cord as described by McDonald at al. (Nat. Med. 5:1410, 1999. A successful transplant will show transplant-derived cells present in the lesion 2-5 weeks later, differentiated into astrocytes, oligodendrocytes, and/or neurons, and migrating along the cord from the lesioned end, and an improvement in gate, coordination, and weight-bearing.

Certain neural progenitor cells are designed for treatment of acute or chronic damage to the nervous system. For example, excitotoxicity has been implicated in a variety of conditions including epilepsy, stroke, ischemia, Huntington's disease, Parkinson's disease and Alzheimer's disease. Certain differentiated cells as made according to the methods described here may also be appropriate for treating dysmyelinating disorders, such as Pelizaeus-Merzbacher disease, multiple sclerosis, leukodystrophies, neuritis and neuropathies. Appropriate for these purposes are cell cultures enriched in oligodendrocytes or oligodendrocyte precursors to promote remyelination.

Hepatocytes and hepatocyte precursors prepared using our methods can be assessed in animal models for ability to repair liver damage. One such example is damage caused by intraperitoneal injection of D-galactosamine (Dabeva et al., Am. J. Pathol. 143:1606, 1993). Efficacy of treatment can be determined by immunohistochemical staining for liver cell markers, microscopic determination of whether canalicular structures form in growing tissue, and the ability of the treatment to restore synthesis of liver-specific proteins. Liver cells can be used in therapy by direct administration, or as part of a bioassist device that provides temporary liver function while the subject's liver tissue regenerates itself following fulminant hepatic failure.

Cardiomyocytes may be prepared by inducing differentiation of stem cells by modulation of the MAP kinase pathway for example with SB203580, a specific p38 MAP kinase inhibitor, as described in Graichen et al (2007). The efficacy of such cardiomyocytes may be assessed in animal models for cardiac cryoinjury, which causes 55% of the left ventricular wall tissue to become scar tissue without treatment (Li et al., Ann. Thorac. Surg. 62:654, 1996; Sakai et al., Ann. Thorac. Surg. 8:2074, 1999, Sakai et al., J. Thorac. Cardiovasc. Surg. 118:715, 1999). Successful treatment will reduce the area of the scar, limit scar expansion, and improve heart function as determined by systolic, diastolic, and developed pressure. Cardiac injury can also be modelled using an embolization coil in the distal portion of the left anterior descending artery (Watanabe et al., Cell Transplant. 7:239, 1998), and efficacy of treatment can be evaluated by histology and cardiac function. Cardiomyocyte preparations can be used in therapy to regenerate cardiac muscle and treat insufficient cardiac function (U.S. Pat. No. 5,919,449 and WO 99/03973).

Cancer

Stem cells propagated according to the methods and compositions described here and differentiated cells derived therefrom may be used for the treatment of cancer.

The terms "cancer" and "cancerous" refer to or describe the physiological condition in mammals that is typically characterized by unregulated cell growth. Examples of cancer include but are not limited to, carcinoma, lymphoma, blastoma, sarcoma, and leukemia. More particular examples of such cancers include squamous cell cancer, small-cell lung cancer, non-small cell lung cancer, gastric cancer, pancreatic cancer, glial cell tumors such as glioblastoma and neurofibromatosis, cervical cancer, ovarian cancer, liver cancer, bladder cancer, hepatoma, breast cancer, colon cancer, colorectal cancer, endometrial carcinoma, salivary gland carcinoma, kidney cancer, renal cancer, prostate cancer, vulval cancer, thyroid cancer, hepatic carcinoma and various types of head and neck cancer. Further examples are solid tumor cancer including colon cancer, breast cancer, lung cancer and prostrate cancer, hematopoietic malignancies including leukemias and lymphomas, Hodgkin's disease, aplastic anemia, skin cancer and familiar adenomatous polyposis. Further examples include brain neoplasms, colorectal neoplasms, breast neoplasms, cervix neoplasms, eye neoplasms, liver neoplasms, lung neoplasms, pancreatic neoplasms, ovarian neoplasms, prostatic neoplasms, skin neoplasms, testicular neoplasms, neoplasms, bone neoplasms, trophoblastic neoplasms, fallopian tube neoplasms, rectal neoplasms, colonic neoplasms, kidney neoplasms, stomach neoplasms, and parathyroid neoplasms. Breast cancer, prostate cancer, pancreatic cancer, colorectal cancer, lung cancer, malignant melanoma, leukaemia, lympyhoma, ovarian cancer, cervical cancer and biliary tract carcinoma are also included. Stem cells propagated and optionally differentiated according to the methods and compositions described here may also be used in combination with anticancer agents such as endostatin and angiostatin or cytotoxic agents or chemotherapeutic agent. For example, drugs such as adriamycin, daunomycin, cis-platinum, etoposide, taxol, taxotere and alkaloids, such as vincristine, and antimetabolites such as methotrexate. The term "cytotoxic agent" as used herein refers to a substance that inhibits or prevents the function of cells and/or causes destruction of cells. The term is intended to include radioactive isotopes (e.g. I, Y, Pr), chemotherapeutic agents, and toxins such as enzymatically active toxins of bacterial, fungal, plant or animal origin, or fragments thereof.

Also, the term includes oncogene product/tyrosine kinase inhibitors, such as the bicyclic ansamycins disclosed in WO 94/22867; 1,2-bis(arylamino)benzoic acid derivatives disclosed in EP 600832; 6,7-diamino-phthalazin-1-one derivatives disclosed in EP 600831; 4,5-bis(arylamino)-phthalimide derivatives as disclosed in EP 516598; or peptides which inhibit binding of a tyrosine kinase to a SH2-containing substrate protein (see WO 94/07913, for example). A "chemotherapeutic agent" is a chemical compound useful in the treatment of cancer. Examples of chemotherapeutic agents include Adriamycin, Doxorubicin, 5-Fluorouracil (5-FU), Cytosine arabinoside (Ara-C), Cyclophosphamide, Thiotepa, Busulfan, Cytoxin, Taxol, Methotrexate, Cisplatin, Melphalan, Vinblastine, Bleomycin, Etoposide, Ifosfamide, Mitomycin C, Mitoxantrone, Vincristine, VP-16, Vinorelbine, Carboplatin, Teniposide, Daunomycin, Caminomycin, Aminopterin, Dactinomycin, Mitomycins, Nicotinamide, Esperamicins (see U.S. Pat. No. 4,675,187), Melphalan and other related nitrogen mustards, and endocrine therapies (such as diethylstilbestrol (DES), Tamoxifen, LHRH antagonizing drugs, progestins, anti-progestins etc).

The practice of the present invention will employ, unless otherwise indicated, conventional techniques of chemistry, molecular biology, microbiology, recombinant DNA and immunology, which are within the capabilities of a person of ordinary skill in the art. Such techniques are explained in the literature. See, for example, J. Sambrook, E. F. Fritsch, and T. Maniatis, 1989, Molecular Cloning: A Laboratory Manual, Second Edition, Books 1-3, Cold Spring Harbor Laboratory Press; Ausubel, F. M. et al. (1995 and periodic supplements; Current Protocols in Molecular Biology, ch. 9, 13, and 16, John Wiley & Sons, New York, N.Y.); B. Roe, J. Crabtree, and A. Kahn, 1996, DNA Isolation and Sequencing: Essential Techniques, John Wiley & Sons; J. M. Polak and James O'D. McGee, 1990, Oligonucleotide Synthesis: A Practical Approach, In Press; D. M. J. Lilley and J. E. Dahlberg, 1992, Methods of Enzymology: DNA Structure Part A: Synthesis and Physical Analysis of DNA Methods in Enzymology, Academic Press; Using Antibodies: A Laboratory Manual: Portable Protocol NO. I by Edward Harlow, David Lane, Ed Harlow (1999, Cold Spring Harbor Laboratory Press, ISBN 0-87969-544-7); Antibodies: A Laboratory Manual by Ed Harlow (Editor), David Lane (Editor) (1988, Cold Spring Harbor Laboratory Press, ISBN 0-87969-3,4-2), 1855; and Lab Ref: A Handbook of Recipes, Reagents, and Other Reference Tools for Use at the Bench, Edited Jane Roskams and Linda Rodgers, 2002, Cold Spring Harbor Laboratory, ISBN 0-87969-630-3: Each of these general texts is herein incorporated by reference.

The invention includes the combination of the aspects and preferred features described except where such a combination is clearly impermissible or expressly avoided.

The section headings used herein are for organizational purposes only and are not to be construed as limiting the subject matter described.

Aspects and embodiments of the present invention will now be illustrated, by way of example, with reference to the accompanying figures. Further aspects and embodiments will be apparent to those skilled in the art. All documents mentioned in this text are incorporated herein by reference.

BRIEF DESCRIPTION OF THE FIGURES

Embodiments and experiments illustrating the principles of the invention will now be discussed with reference to the accompanying figures in which.

EXAMPLES

Figure 1:
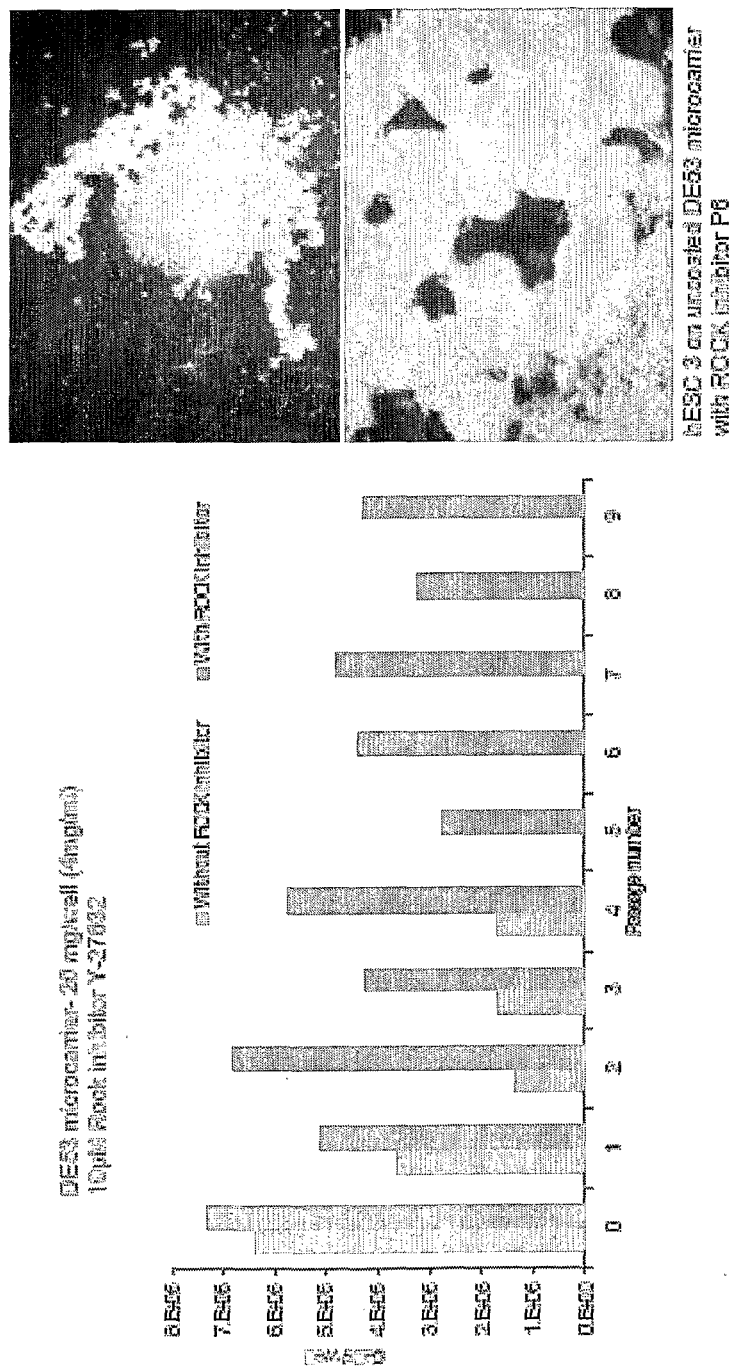
FIG. 1. Chart showing results of nine consecutive weeks of passaging hESC on DE53 cellulose microcarriers without Matrigel but with Rock inhibitor Y-27632. Without ROCK Inhibitor, hESC cannot be passaged after week 4.

The following Examples provide evidence of the stable, long term propagation of human embryonic stem cells on a variety of microcarriers (DE53, QA52, Tosoh, Cytodex 1, Cytodex 3) without the use of an extracellular matrix, but with supplements of ROCK inhibitors (Y-27632, HA1077 or Fasudil, and Aurothioglucose). hESC retained their growth, final cell densities, expression of the pluripotent markers Oct4, mAb 84 and TRA-1-60, and normal karyotypes after 5 or more passages.

Example 1

Human Embryonic Stem Cells (hESC)

Human embryonic stem cell lines, HES-2 (46 X, X), and HES-3 (46x, X) are obtained from ES Cell International. The cells are frozen and stored in liquid nitrogen as a suspension of 200×200 μm cell clumps obtained from 2D colony culture or as cell-microcarrier aggregates obtained from microcarrier cultures.

Example 2

Cell Culture: 2D Colony Culture

For maintenance of hESC, cells can be cultured at 37° C./5% $CO_2$ on Matrigel-coated culture dishes (incubated at 4 degrees C. overnight with Matrigel (Becton Dickinson), diluted in cold KO-DMEM, 1:30 dilution). Cells are routinely maintained in organ culture dishes (OCD) with 1 ml of media.

Media used are either Conditioned Media (CM) from MEF feeders, StemPro hESC serum free media (Invitrogen) or mTeSR-1 serum free media (Cell Technologies). Medium is changed daily. The static colony cultures are passaged weekly either by enzymatic treatment with collagenase (Choo et al, 2004) or trypLE Express (Invitrogen) or by mechanical dissection using the StemPro EZPassage Stem Cell Passaging Tool (Invitrogen)

Example 3

Cell Culture: 3D Microcarrier Cultures

Cells suspension obtained either from dispersed 2D colony culture or directly from liquid nitrogen storage (200×200 μm tissue obtained from 2D colony culture or as cell-microcarriers aggregates) are seeded at concentrations of $0.1-0.3 \times 10^6$/ml on microcarrier suspension (4 mg/ml).

In some experiments, in order to ensure more homogeneous culture, the cell inoculum is screened through 100 and 500 μm mesh sieve before its addition to the microcarrier suspension. Cells are cultured at 37° C./5% $CO_2$ on non attachment 6 well dishes (Corning) in static condition or agitated at 100 or 150 rpm (IKA Orbital Shaker). The media used are either MEF-CM or defined media. Medium is changed daily. The cultures are passaged weekly following either enzymatic treatment with collagenase or trypLE or following mechanical dissociating by repeated pipetting at a split ratio of 1:2 to 1:10. Replating of microcarrier cultures to 2D colony culture is done by placing confluent cell-microcarrier aggregates on Matrigel coated 6 cm tissue culture petridish with 8 mls of media, and culturing the cells for 7 days.

Example 4

Spinner Cultures hESC are seeded to a siliconised (Sigmacote, SL2 Sigma-Aldrich) 100 ml Bellco spinner flask at a density of $3 \times 10^5$ cells/ml to 5 mg/ml of microcarriers, in an initial volume of 25 ml without agitation inside a controlled incubator with 37° C. and 5% $CO_2$.

The reactor volume is increased to 50 ml with fresh conditioned medium and agitated at 30 rpm, 12 h after inoculation. 80% of the spent medium is removed daily and replaced with fresh conditioned medium. Daily samples are taken for cell counts and metabolite analysis.

Example 5

Culture on Microcarriers in the Absence of Matrigel and in the Presence of ROCK Inhibitor Materials and Methods
Preparation of Conditioned Media for hESC Culture on Microcarriers Conditioned media was prepared following our published protocol—Choo et al., 2007 (Identification of proteins from feeder conditioned medium that support human embryonic stem cells. J. Biotechnol. 130, 320-328).

Seeding of hESC on DE53, QA52, Tosoh, Cytodex 1 and Cytodex 3 microcarriers hESC were seeded on uncoated microcarriers and passaged weekly following the protocol of Example 3 and that of Oh et al., 2009 (Long term microcarrier suspension cultures of human embryonic stem cells, Stem Cell Research (2009)).

Preparation of Rock Inhibitors
Y-27632—For 10 mM stock: Dissolve 5 mg in 1.48 ml of water.
HA1077 (Fasudil)—For 10 mM stock: Dissolve 5 mg in 1.37 mlwater.
Aurothioglucose (AuTG)—For 10 mM stock: Dissolve 5 mg in 1.28 ml water All chemicals were purchased from Calbiochem. All inhibitors were diluted to their final working concentration in conditioned media prior to feeding hESC on microcarriers.

FACS Characterization of Pluripotent Markers
Characterisation was performed according to our recent paper by Oh et al., 2009 (Long term microcarrier suspension cultures of human embryonic stem cells, *Stem Cell Research* (2009)).

Briefly, expression levels of extracellular antigens TRA-1-60 and intracellular transcription factor, Oct-4 in hESC populations are assessed by immunofluorescence using flow cytometry. Cells are harvested as single cell suspensions using trypsin or trypLE express, filtered through a 40 μm sieve (BD) fixed, permeabilised (Caltag Laboratories) and incubated with primary antibodies to TRA-1-60 (1:50 dilution, Chemicon, MAB4360/4381) and to Oct-4 (1:20 dilution, Santa Cruz).

Cells are then washed with 1% BSA/PBS, and incubated in the dark with a 1:500 dilution of goat α-mouse antibody FITC-conjugated (DAKO). After incubation, the cells are again washed and resuspended in 1% BSA/PBS for analysis on a FACScan (Becton Dickinson FACS Calibur). All incubations are performed at room temperature for 15 min.

Karyotyping
Actively growing cultures of hESC are arrested in the metaphase stage following incubation with colcemid solution diluted in 1 ml KO-medium for 15-16 h at 37 degrees C./5% $CO_2$. Cytogenetics analysis is outsourced to the Cytogenetics Laboratories at the KK Women's and Children's Hospital, Singapore.

SEM
Scanning electron micrographs were performed at the SEM Unit, Institute of Molecular Cell Biology, Singapore.

Results
In the following discussion, culture of hESC on Matrigel free microcarriers is presented under the following headings:—
1. Long term culture of hESC on cellulose DE53 microcarriers for 9 weeks with ROCK inhibitor Y-27632.
2. Long term culture of hESC on spherical Tosoh microcarriers for 6 weeks with ROCK inhibitor Y-27632.

3. Comparison of long term culture of hESC on cellulose DE53, Tosoh, Cytodex1 and Cytodex 3 microcarriers for 5 weeks with ROCK inhibitor Y-27632.
4. Scanning electron micrographs of hESC on cellulose DE53 with ROCK inhibitor Y-27632.
5. Karyotypes of hESC on cellulose DE53, QA52, Tosoh, and Cytodex 3 microcarriers between 5 to 10 weeks with ROCK inhibitor Y-27632.
6. Culture of hESC on cellulose DE53 microcarriers for 2 weeks with alternative ROCK inhibitors, HA1077 (Fasudil) and Aurothioglucose.

Long Term Culture of hESC on Cellulose DE53 Microcarriers for 9 Weeks with ROCK Inhibitor Y-27632

Figure 2:
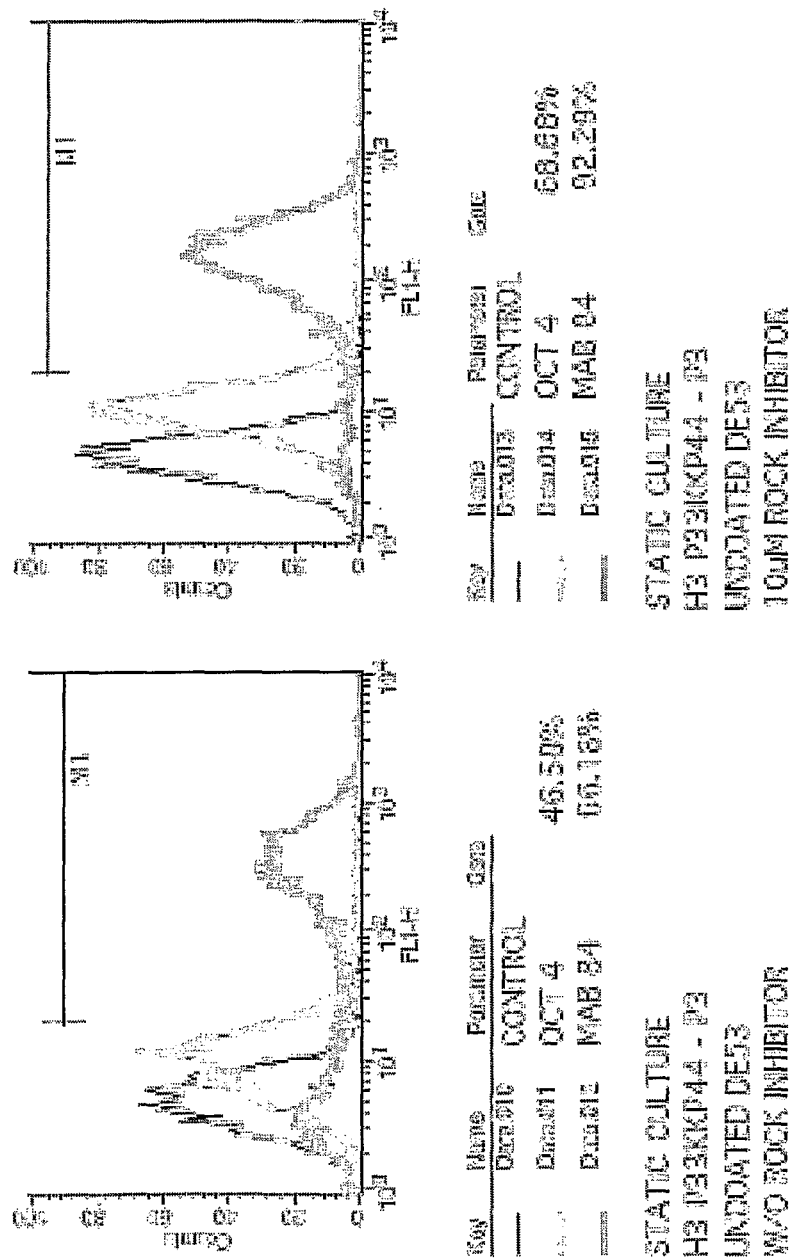
FIG. 2. FACS analysis. Stable expression of pluripotent markers Oct4 and mAb 84 over 3 weeks in microcarrier cultures without Matrigel but with ROCK inhibitor, showing down regulation of markers without ROCK inhibitor.
Figure 3:
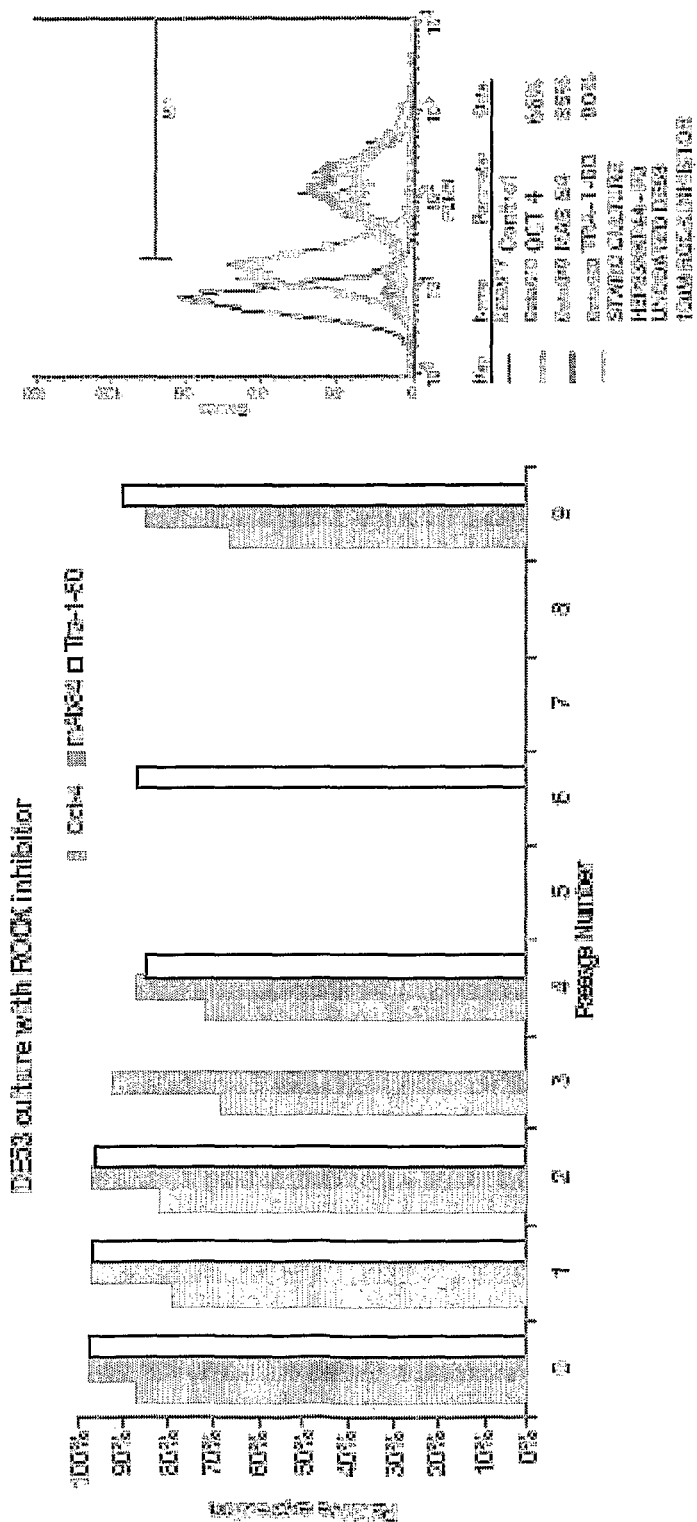
FIG. 3. Chart showing stable expression of pluripotent markers Oct4, mAb 84 and Tra-1-60 over 9 weeks in microcarrier cultures without Matrigel but with ROCK inhibitor.

FIG. 1 shows that hESC can be passaged consecutively for 9 weeks on cellulose DE53 microcarriers with ROCK inhibitor Y-27632 supplemented at 10 µM. Cell densities achieved vary from 3 to 7.5 million/well in 6 well plates (each well volume is 4 ml). However, in the absence of ROCK inhibitor Y-27632, cell numbers decline sharply and cannot be passaged beyond week 4. hESC form confluent aggregates around the microcarriers. FIG. 2 shows stable expression of pluripotent markers Oct4 and mAb 84 over 3 weeks in microcarrier cultures without Matrigel but with ROCK inhibitor, but significant down regulation of markers without ROCK inhibitor. By 9 weeks, expression of pluripotent markers Oct4, mAb 84 and Tra-1-60 are still robust in microcarrier cultures without Matrigel but with ROCK inhibitor Y-27632 (FIG. 3).

Long Term Culture of hESC on Spherical Tosoh Microcarriers for 6 Weeks with ROCK Inhibitor Y-27632

Figure 4:
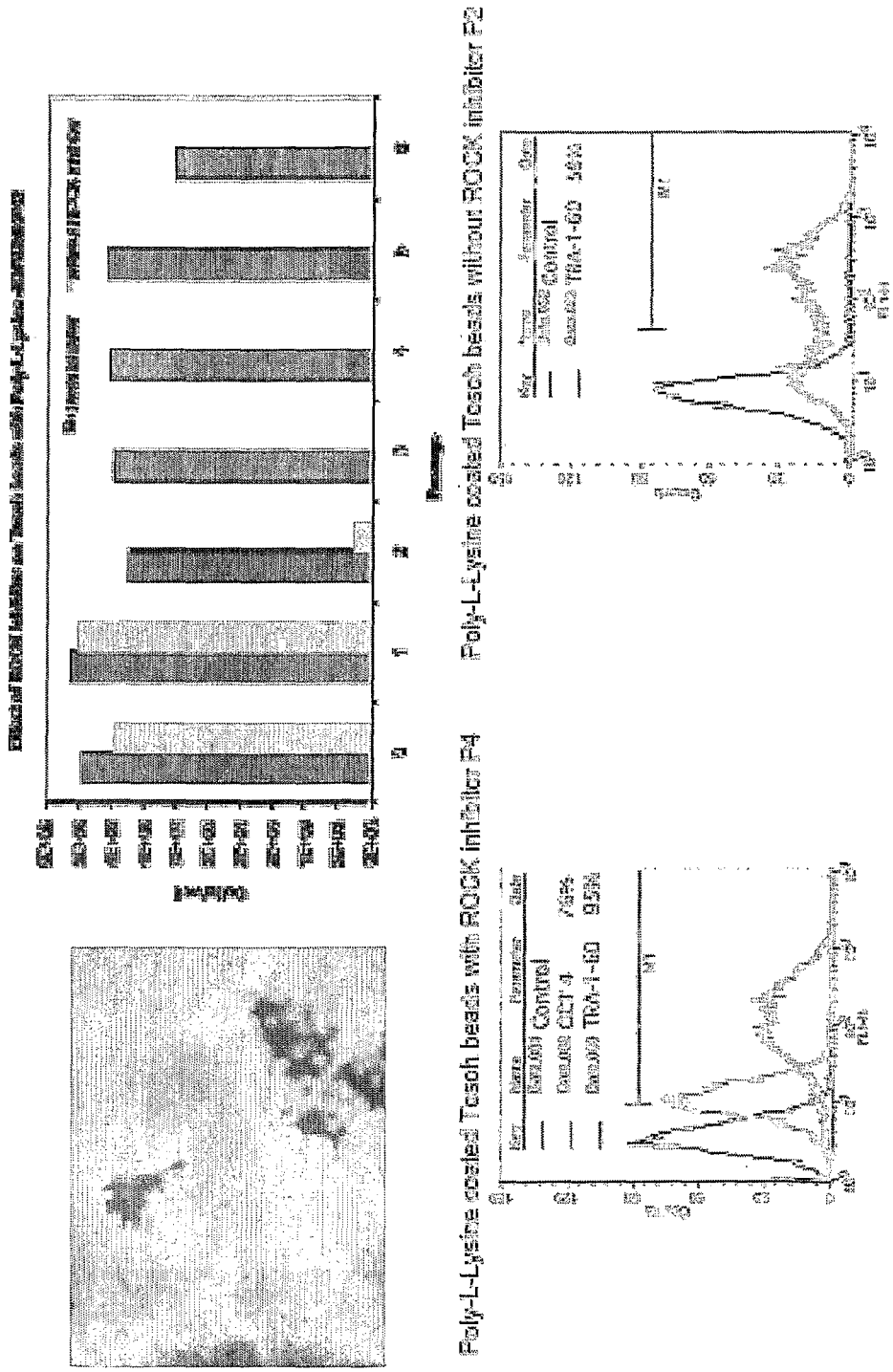
FIG. 4. Chart and FACS analysis showing results of six consecutive weeks of passaging hESC on spherical polylysine coated Tosoh microcarriers without Matrigel but with Rock inhibitor Y-27632. Without ROCK Inhibitor, hESC cannot be passaged after week 2.

FIG. 4 shows six consecutive weeks of passaging hESC on spherical Tosoh 65 micron microcarriers that have been positively charged with polylysine without Matrigel but supplemented with Rock inhibitor Y-27632. Cell numbers range from 3 to 5 million/well. Pluripotent markers Oct4, and Tra-1-60 are strongly expressed at passage 4. However, in the absence of Rock inhibitor Y-27632 the cell numbers dropped drastically at passage 2 and what cells are left show significant down regulation of pluripotent marker Tra-1-60.

Comparison of Long Term Culture of hESC on Cellulose DE53, Tosoh, Cytodex1 and Cytodex 3 Microcarriers for 5 Weeks with ROCK Inhibitor Y-27632

Figure 5:
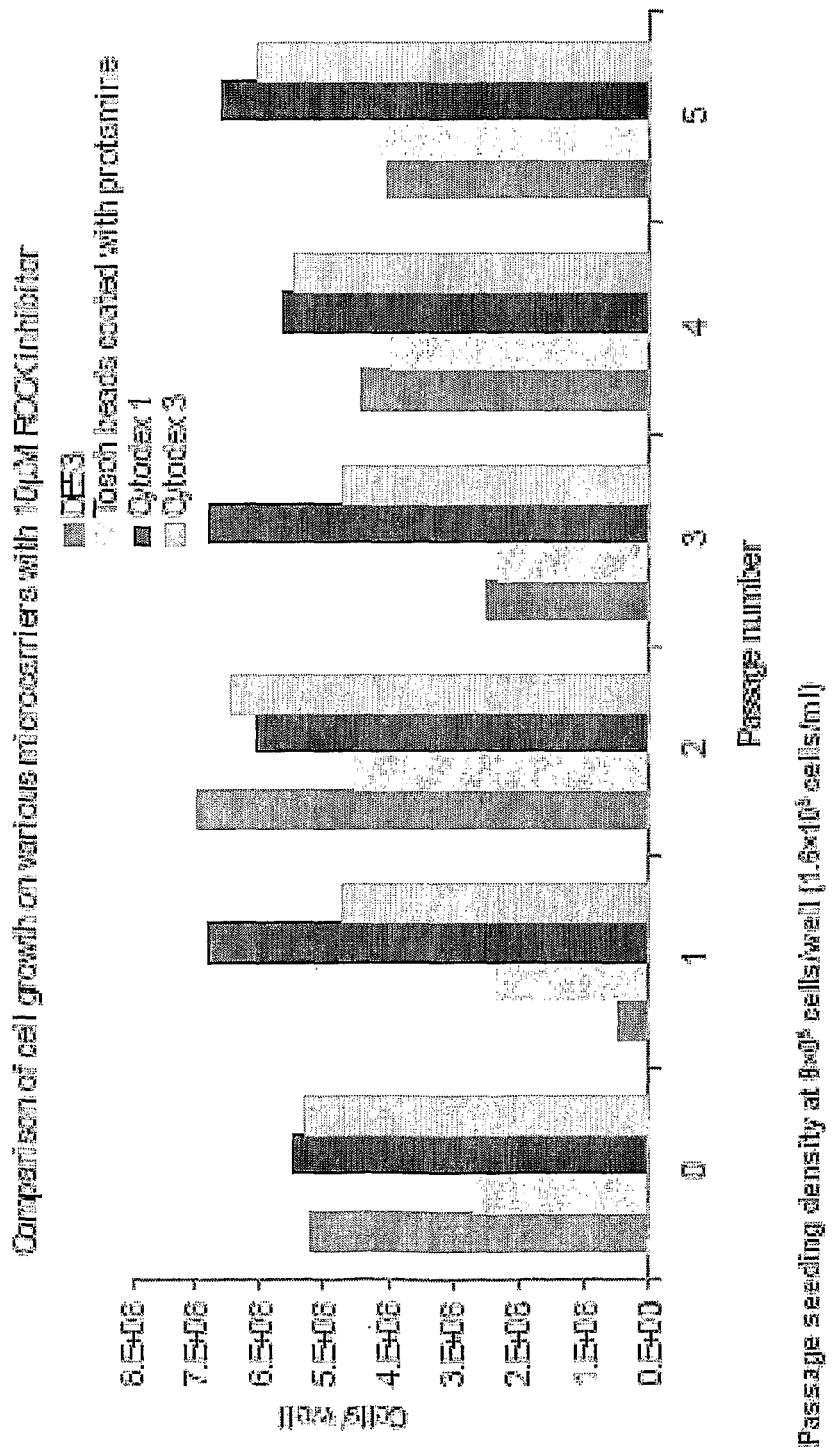
FIG. 5. Chart showing results of five consecutive weeks of passaging hESC on cellulose DE53, Tosoh, Cytodex 1 and Cytodex 3 microcarriers without Matrigel but with Rock inhibitor Y-27632.
Figure 6:
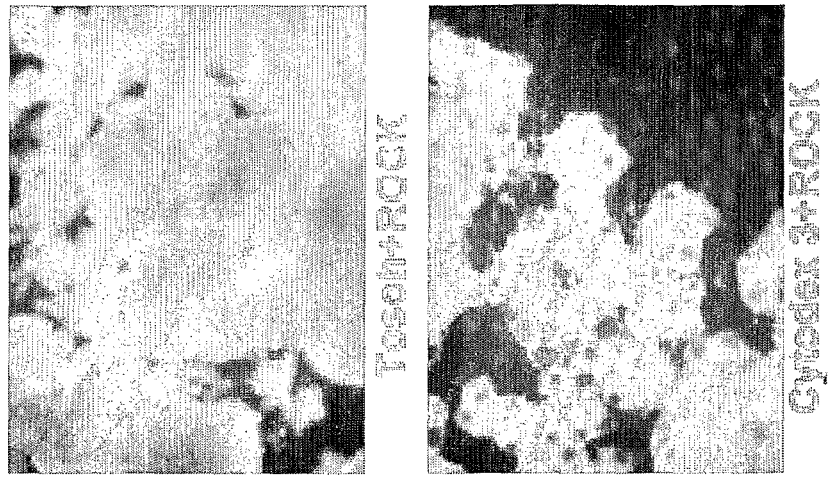
FIG. 6. Micrographs of hESC on cellulose DE53, Tosoh, Cytodex 1 and Cytodex 3 microcarriers without Matrigel but with Rock inhibitor Y-27632.
Figure 6:
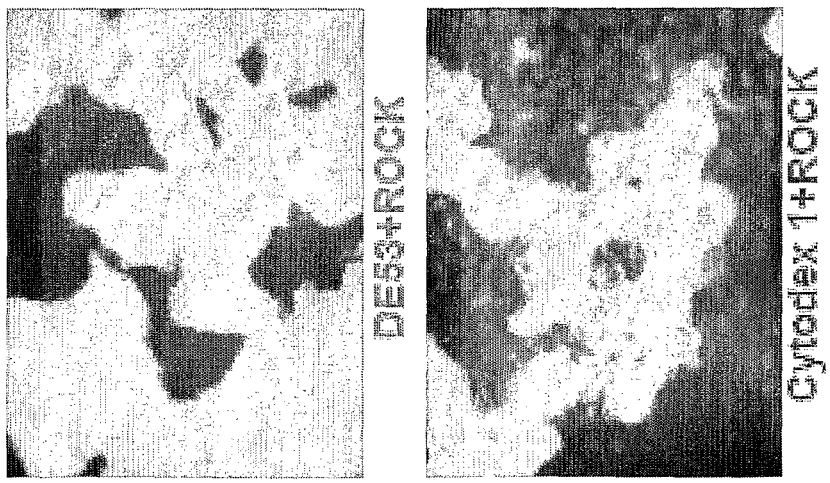
Figure 7:
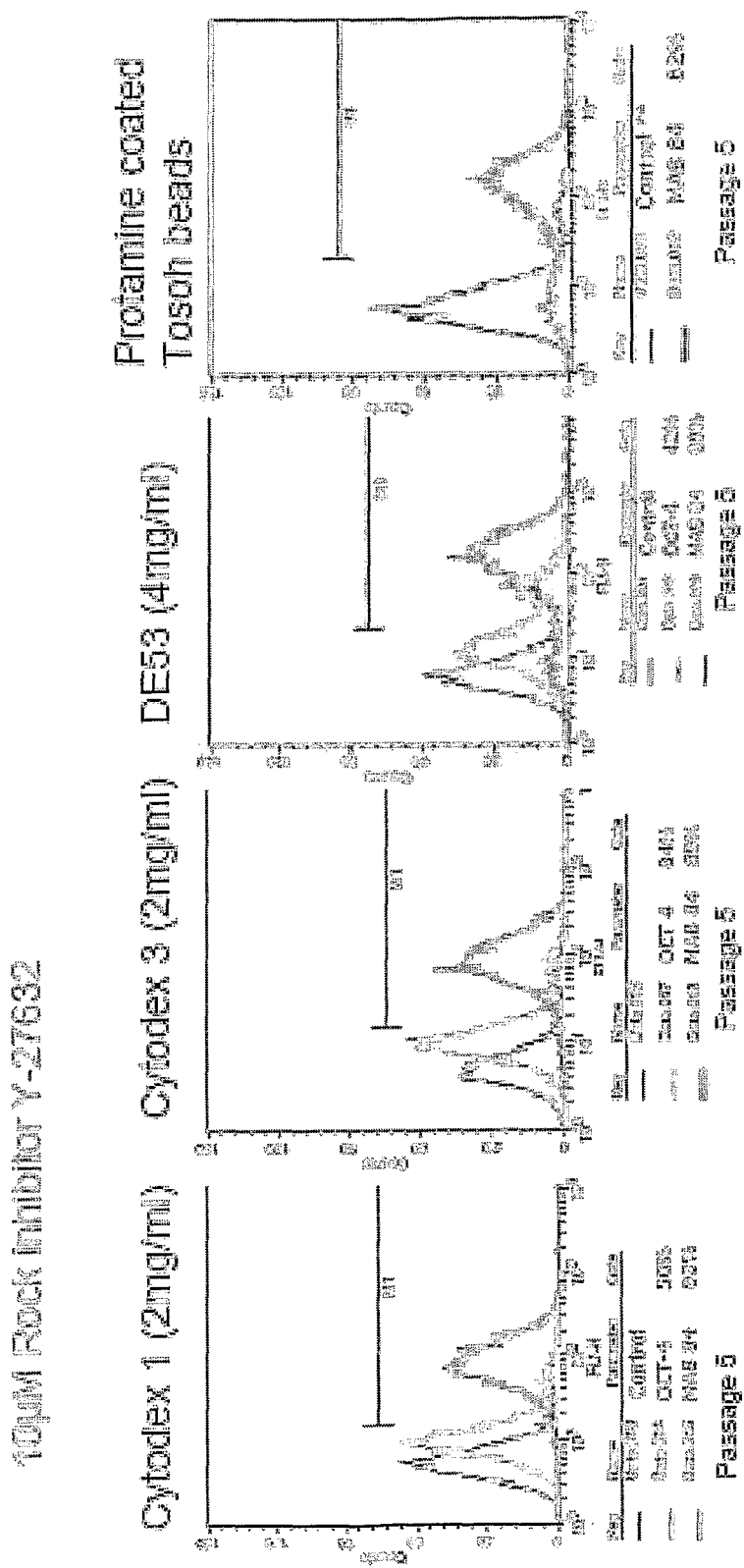
FIG. 7. FACS analysis. Oct4 and mAb 84 expression in hESC cultured on cellulose, Tosoh, Cytodex 1 and Cytodex 3 microcarriers without Matrigel but with Rock inhibitor Y-27632 at passage 5.

FIG. 5 shows five consecutive weeks of passaging hESC on cellulose, Tosoh, Cytodex 1 and Cytodex 3 microcarriers without Matrigel but with Rock inhibitor Y-27632. In particular, cell numbers achieved on Cytodex 1 and Cytodex 3 microcarriers appear to be higher ranging from 5 to 7 million/well, while cellulose and Tosoh microcarriers achieved 4 million/well at passage 5. Pictures of hESC on cellulose, Tosoh, Cytodex 1 and Cytodex 3 microcarriers without Matrigel but with Rock inhibitor Y-27632 are shown (FIG. 6). hESC clusters appear confluent on all these microcarrier cultures. FIG. 7 shows that there is robust expression of pluripotent markers Oct4 and mAb 84 by hESC cultured on Cytodex 1, Cytodex 3, cellulose, and Tosoh microcarriers without Matrigel but with Rock inhibitor Y-27632 at passage 5.

Scanning Electron Micrographs of hESC on Cellulose DE53 with ROCK Inhibitor Y-27632

Figure 8:
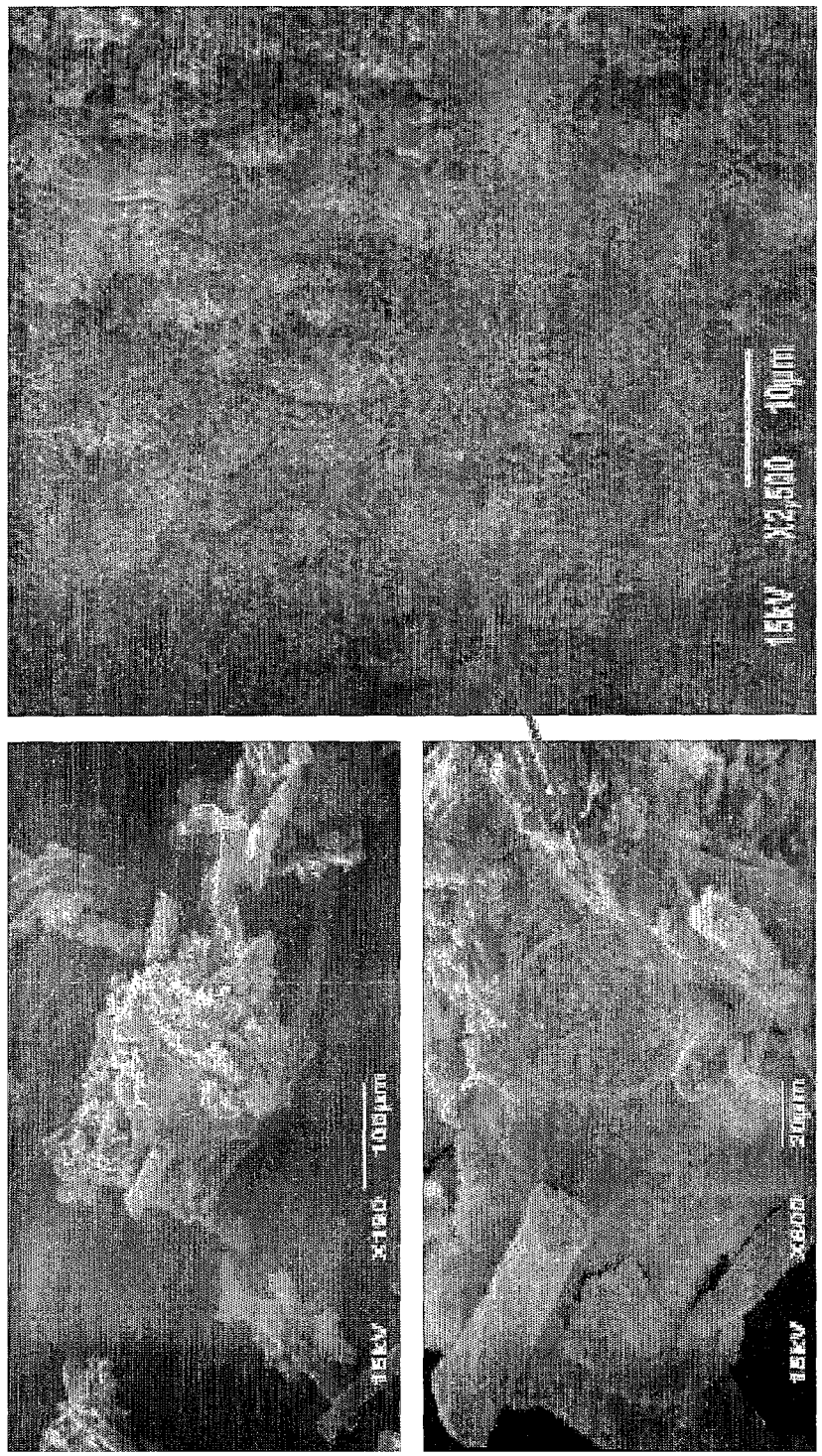
FIG. 8. Scanning electron micrographs (SEM) of hESC on cellulose microcarrier without Matrigel but with Rock inhibitor Y-27632.
Figure 9:
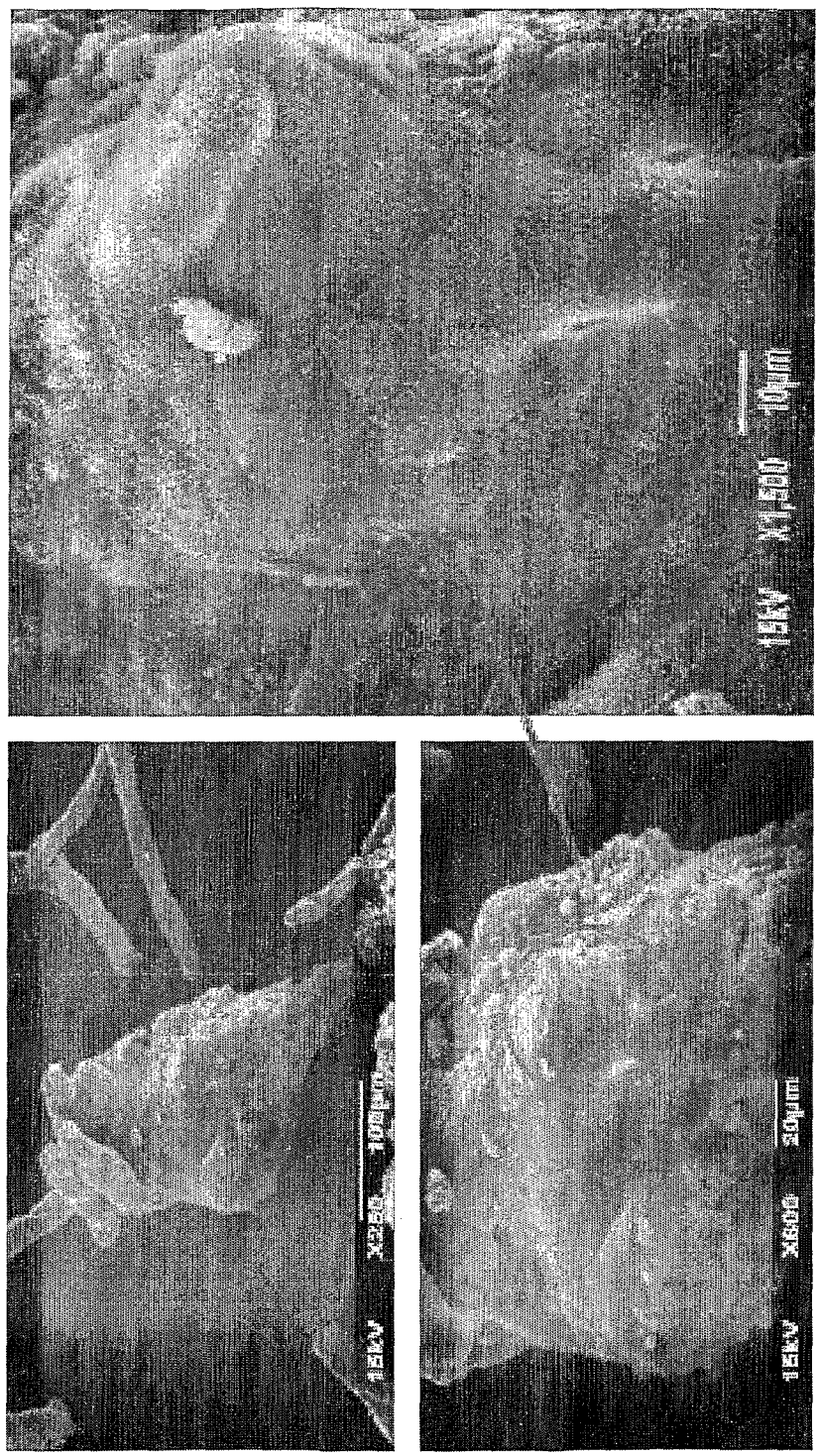
FIG. 9. SEM of hESC cellulose microcarriers without Matrigel but with Rock inhibitor Y-27632.

FIG. 8 shows scanning electron micrographs (SEM) of hESC on cellulose microcarrier without Matrigel but with Rock inhibitor Y-27632. hESC form tight and confluent aggregates of cells surrounding the cellulose microcarriers. FIG. 9 shows a second example of a SEM of hESC on microcarriers on cellulose microcarrier without Matrigel but with Rock inhibitor Y-27632

Karyotypes of hESC on Cellulose DE53, QA52, Tosoh, and Cytodex 3 Microcarriers Between 5 to 10 Weeks with ROCK Inhibitor Y-27632

Figure 10:
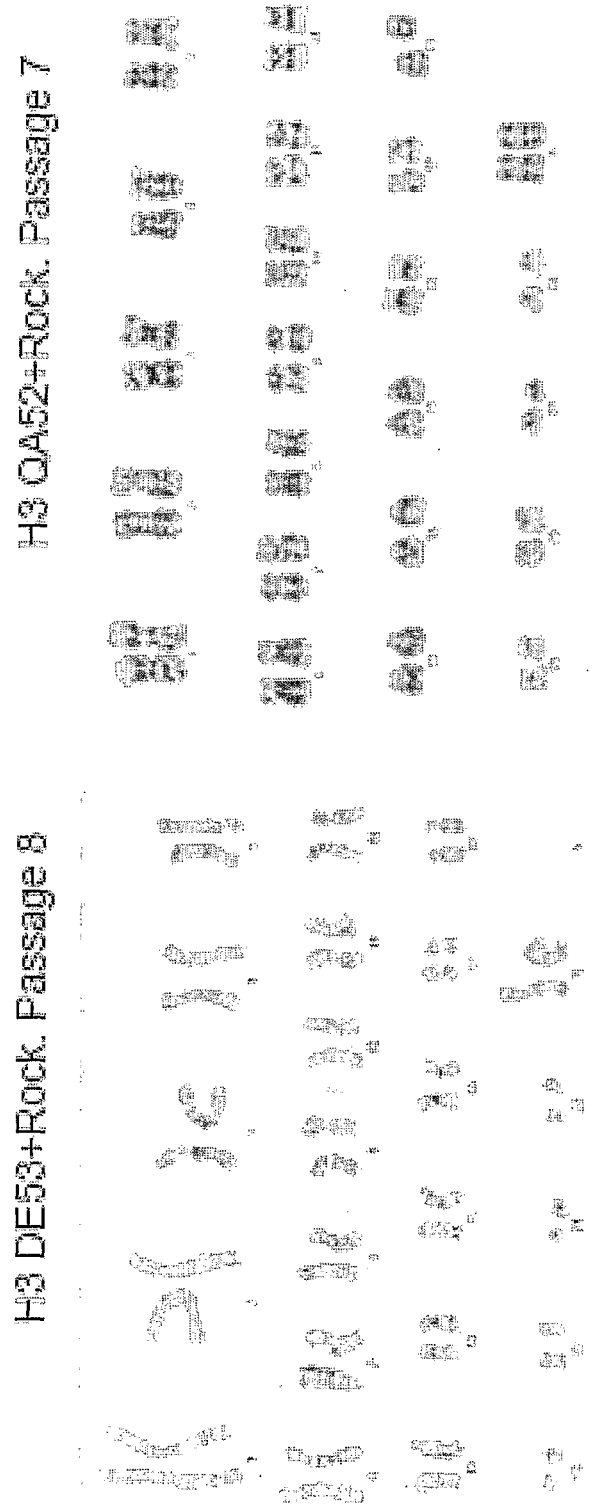
FIG. 10. Stable karyotype of hESC cultured on DE53 and QA52 cellulose microcarriers at passage 8 and 7 respectively.
Figure 11:
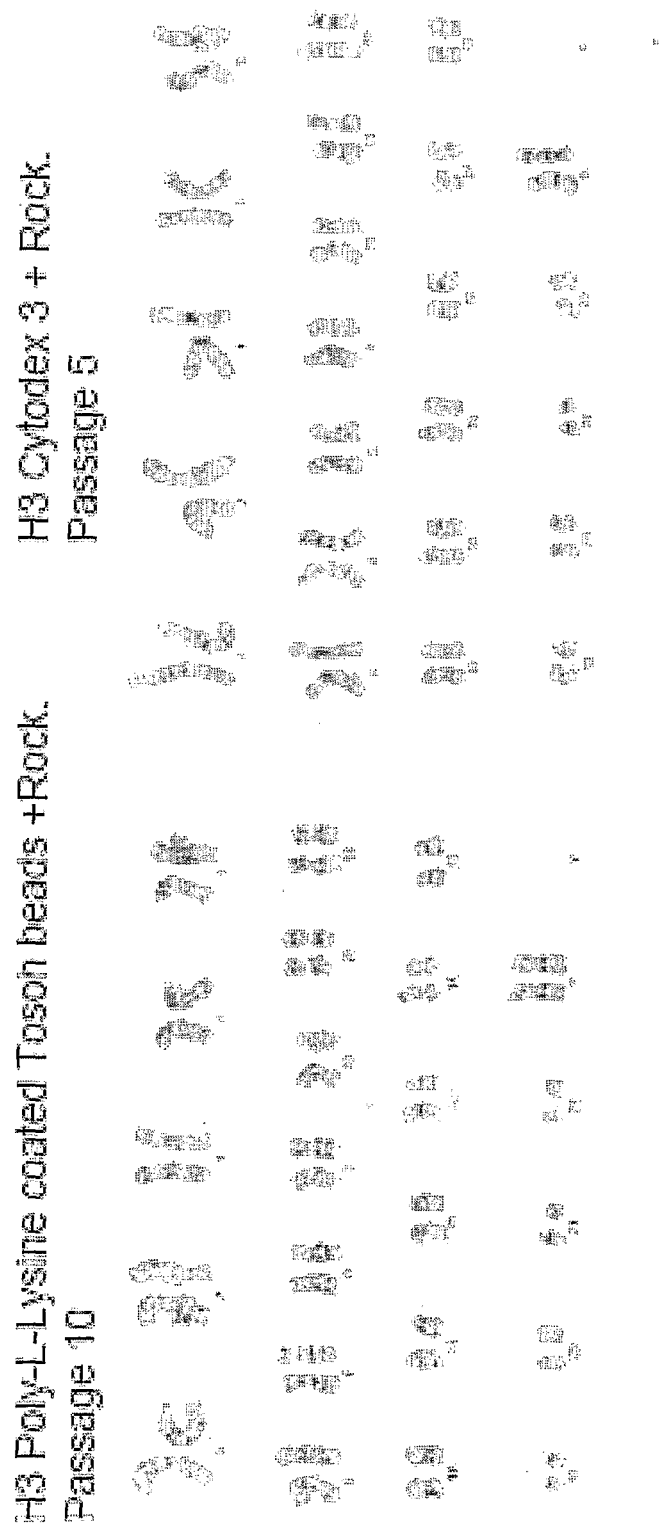
FIG. 11. Stable karyotype of hESC cultured on spherical Tosoh and Cytodex 3 microcarriers at passage 10 and 5 respectively.

FIG. 10 shows that hESC cultured on DE53 and QA52 cellulose microcarriers retain a stable karyotype at passage 8 and 7 respectively. Similarly, FIG. 11 shows stable karyotype of hESC cultured on spherical, polylysine coated Tosoh and Cytodex 3 microcarriers at passage 10 and 5 respectively.

Culture of hESC on Cellulose DE53 Microcarriers for 2 Weeks with Alternative ROCK Inhibitors, HA1077 (Fasudil) and Aurothioqlucose Other types of ROCK inhibitor were evaluated, including:
1. HA1077 (Fasudil): ROCK inhibitor
2. Aurothioglucose: NF-κB inhibitor
3. LY 294002: P13K inhibitor
4. Hydroxyfasudil: ROCK inhibitor
5. Rho Kinase Inhibitor I: ROCK inhibitor
6. Rho Kinase Inhibitor II: ROCK inhibitor Controls used were DE53 microcarriers coated with Matrigel. Blanks comprising 0.02 µl DMSO spiked in uncoated DE53 were also used.

Figure 12:
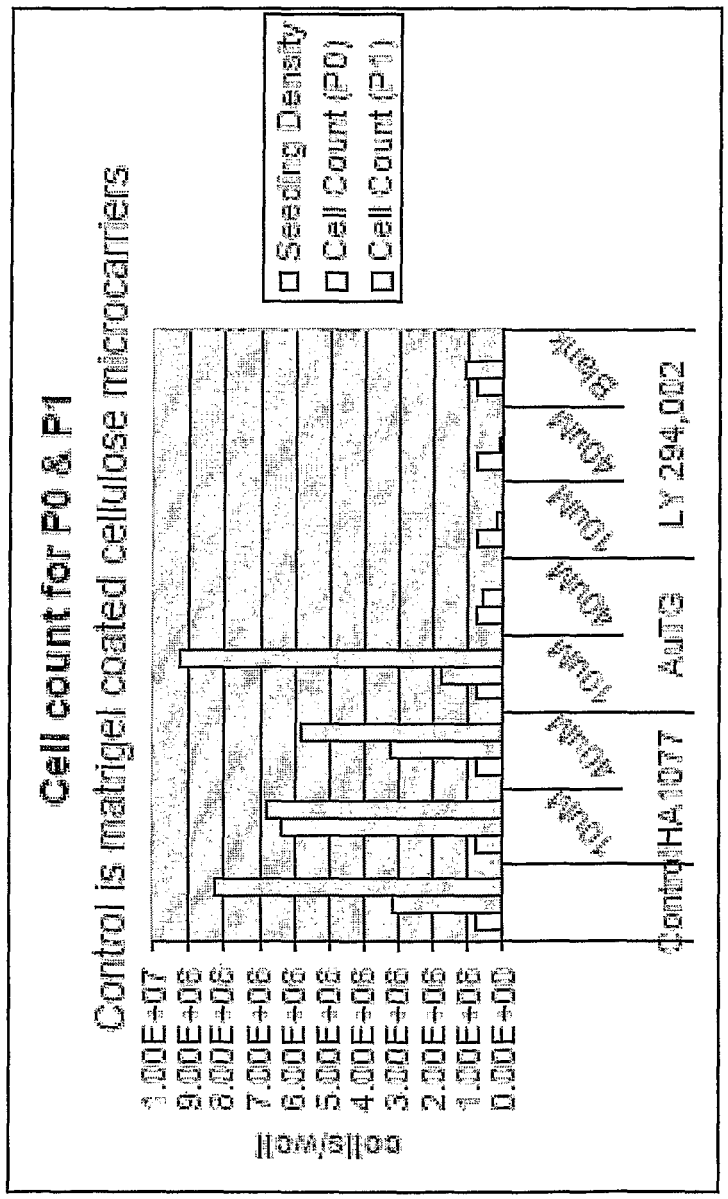
FIG. 12. Chart showing inhibitors HA1077 and Aurothioglucose to support the growth of hESC on cellulose microcarriers without Matrigel at passage 0 and 1.
Figure 13:
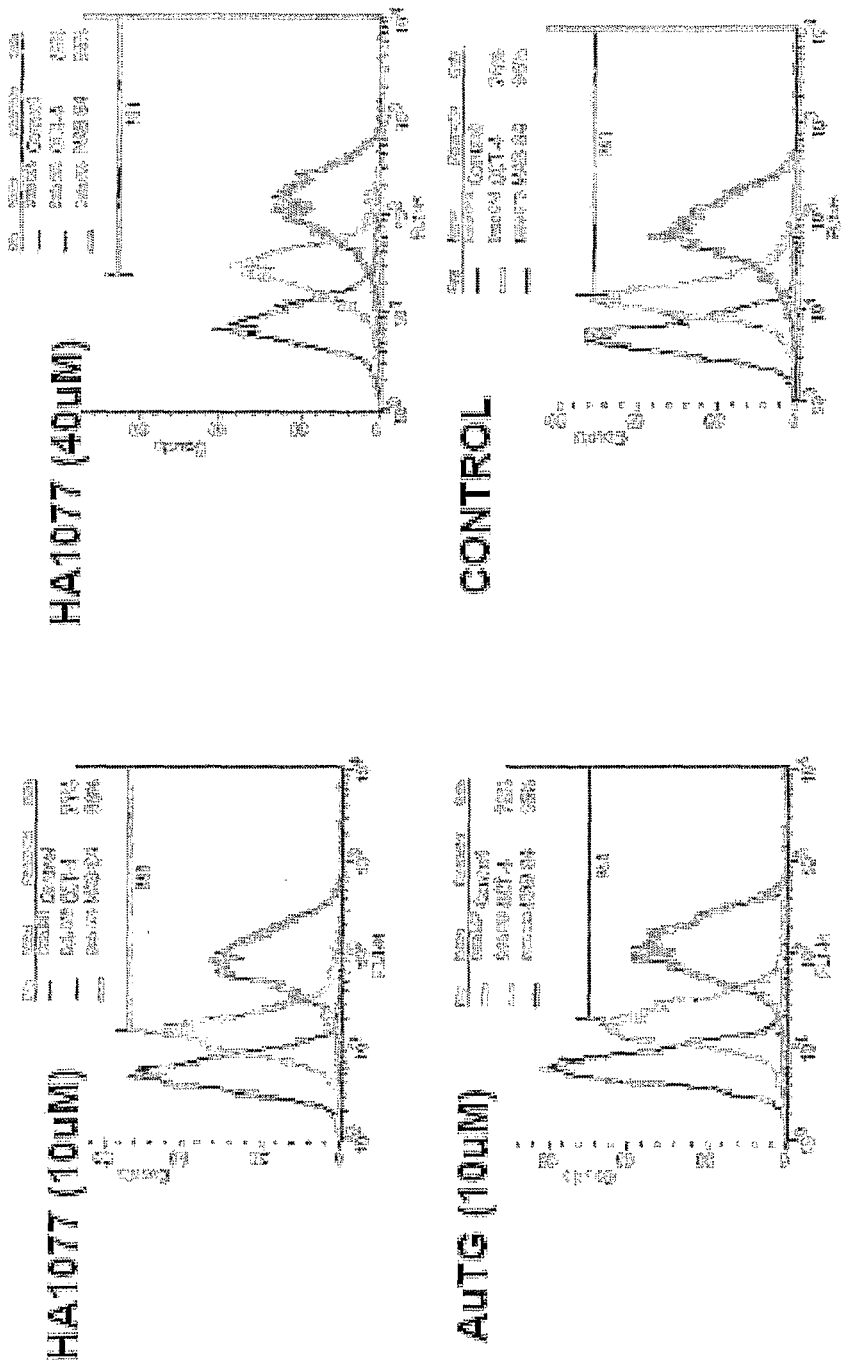
FIG. 13. FACS analysis. Stable expression of pluripotent markers Oct4 and mAb 84 of hESC cultures with inhibitors HA1077 and Aurothioglucose at passage 0.
Figure 14:
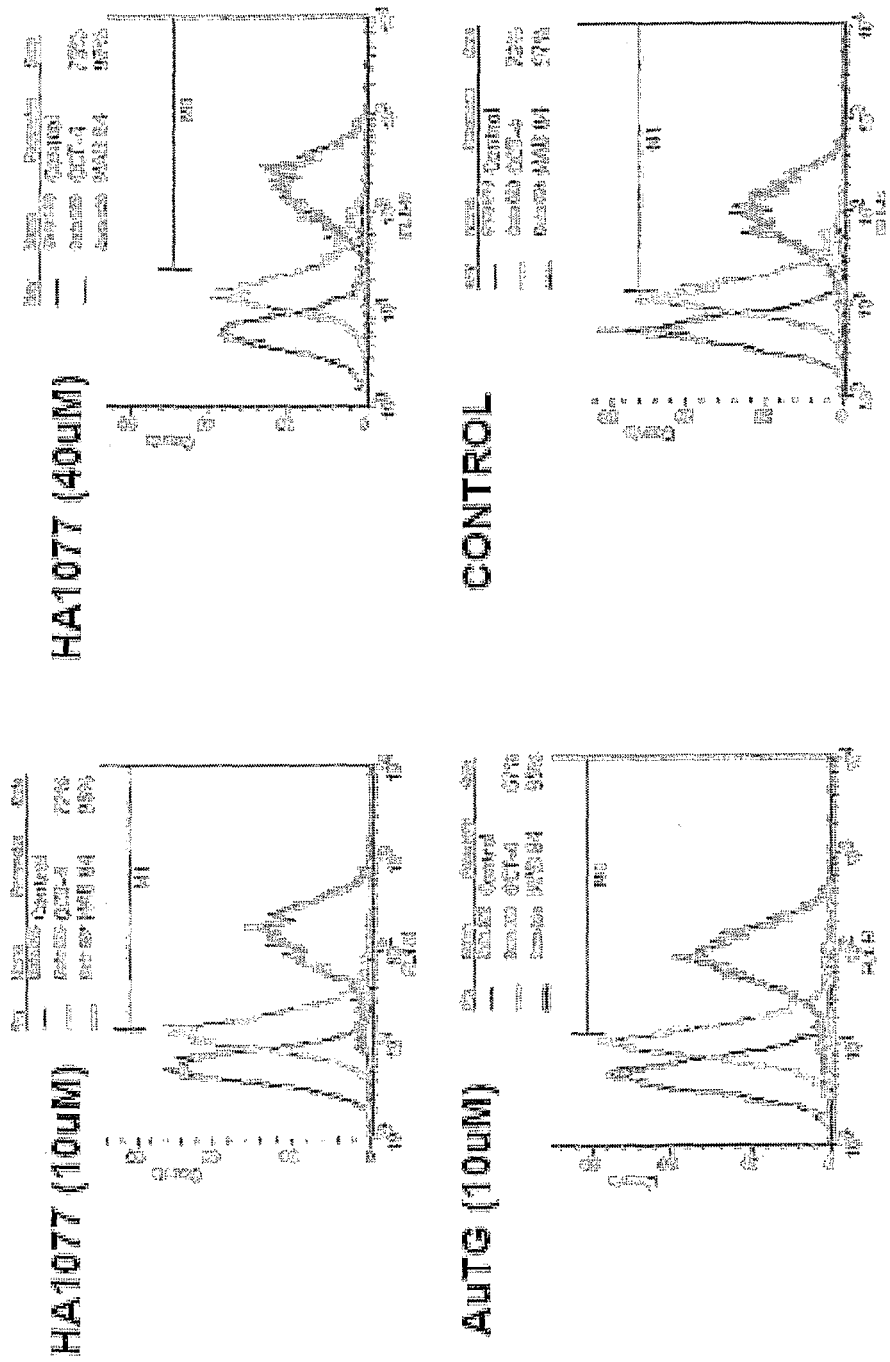
FIG. 14. FACS analysis. Stable expression of FACS of pluripotent markers Oct4 and mAb 84 of hESC cultures with inhibitors HA1077 and Aurothioglucose at passage 1.
Figure 15:
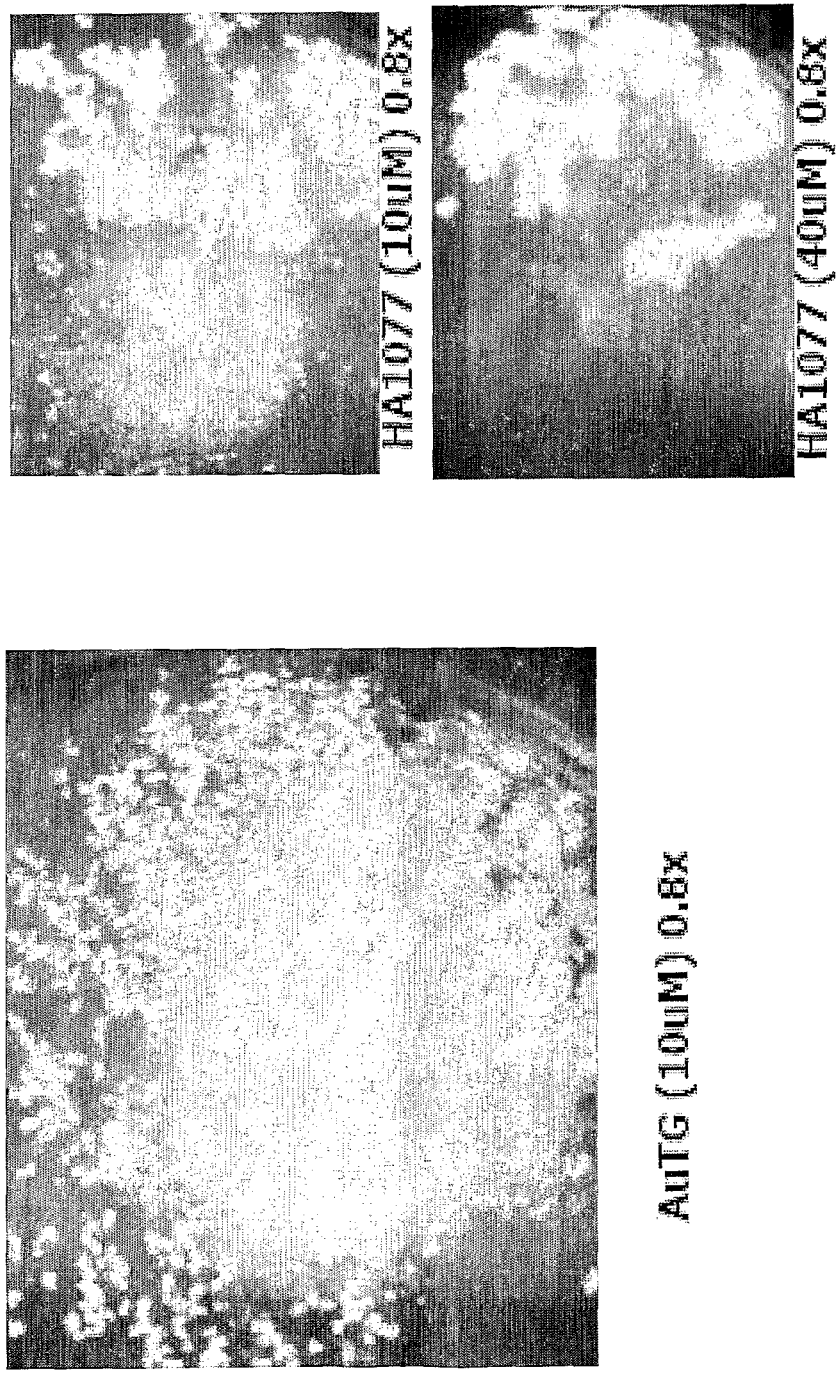
FIG. 15. Micrographs of confluent cultures of hESC on microcarriers with alternative ROCK inhibitors.
Figure 16:
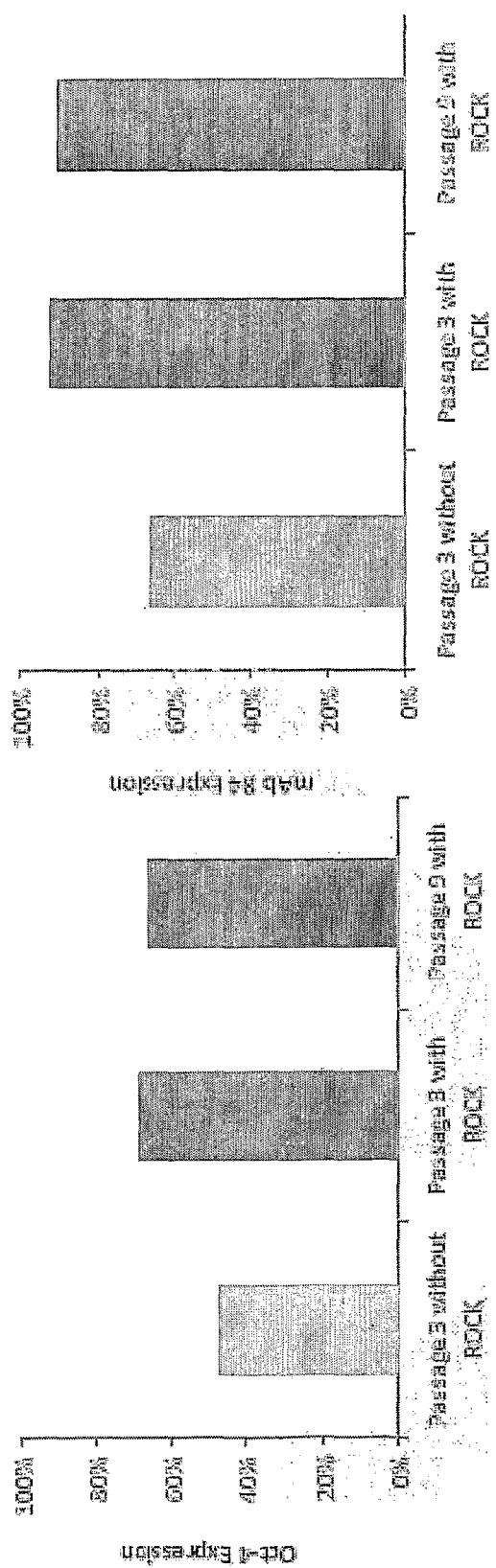
FIG. 16. Chart showing effect of long term hESC culture on cellulose microcarriers with ROCK Inhibitor Y-27632. Down regulation of Oct4 and mAb 84 without ROCK Inhibitor and stable expression of Oct4 and mAb 84 over 9 weeks with ROCK inhibitor.
Figure 17:
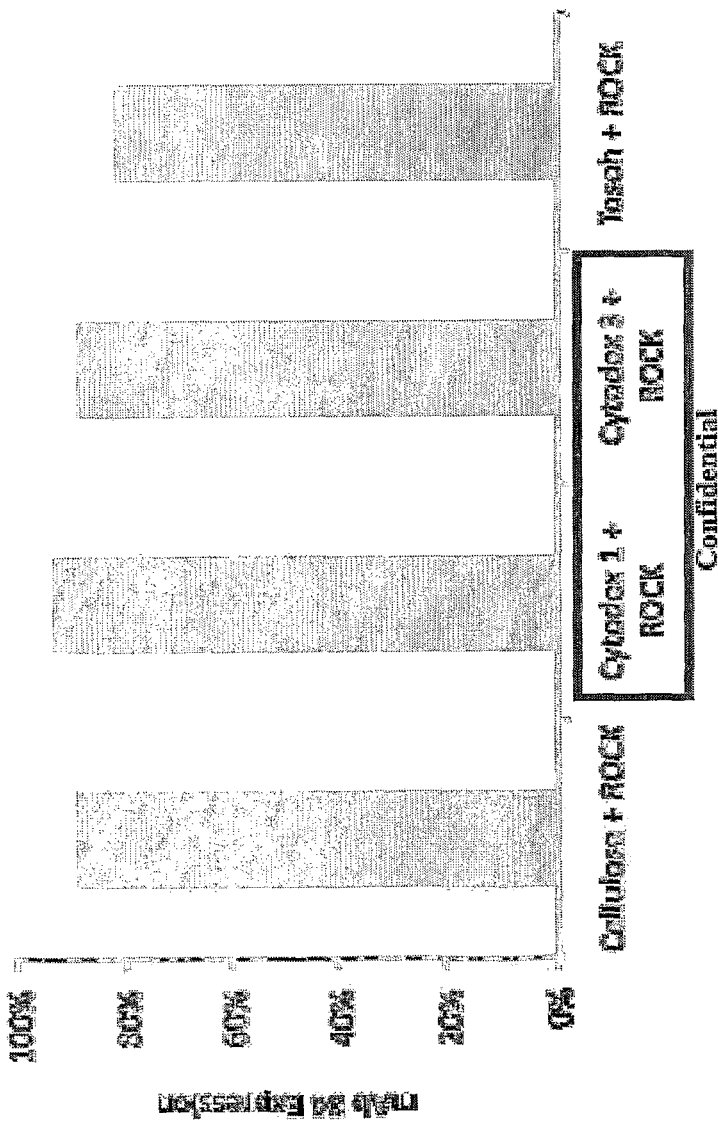
FIG. 17. Chart showing comparison of hESC culture on cellulose DE53, Tosoh, Cytodex1 and Cytodex 3 microcarriers with and without ROCK Inhibitor (Y-27632).
Figure 18:
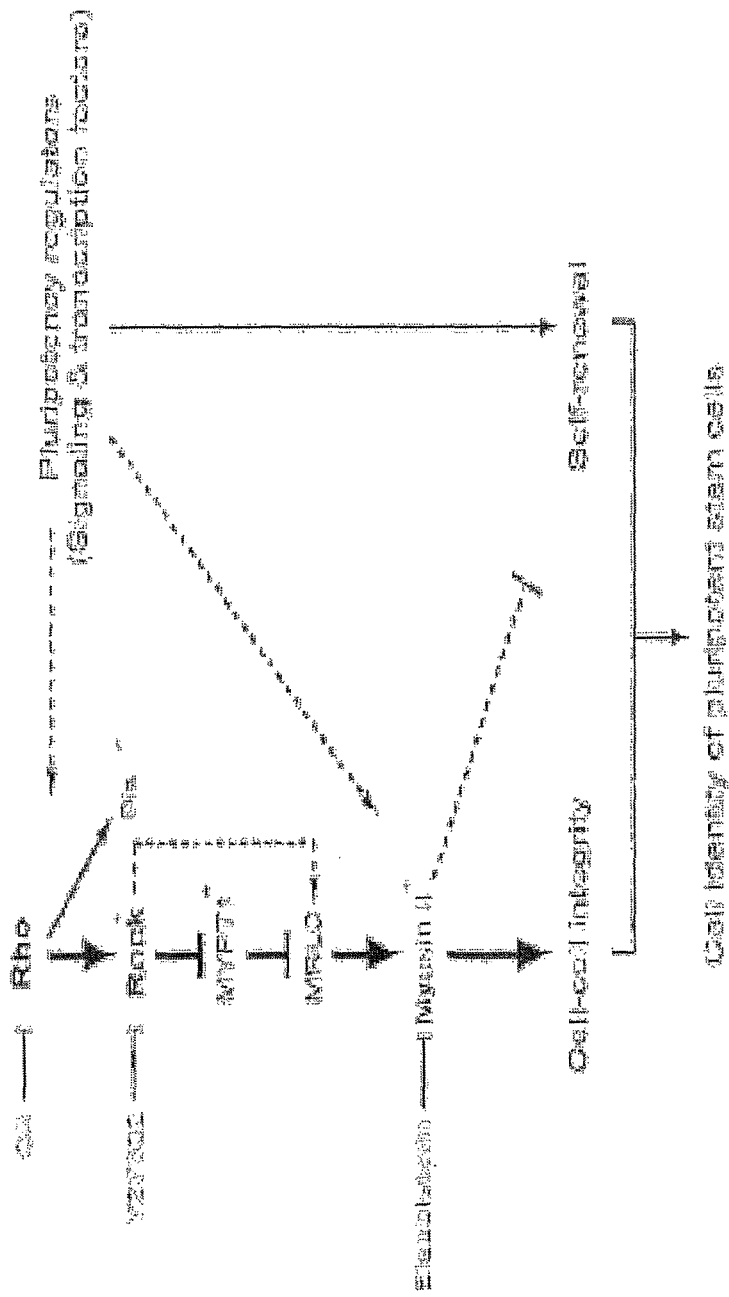
FIG. 18. Diagram representing a summary of the Rho-Rock-Myosin pathway that regulates basic cell-cell interaction in embryonic stem cells. Dotted lines show potential mechanistic actions within or between cell integrity and cell renewal pathways (from Harb et al. The Rho-Rock-Myosin Signaling Axis Determines Cell-Cell Integrity of Self-Renewing Pluripotent Stem Cells. PLoS ONE 3(8): e3001. doi: 10:1371/journal.pone.0003001).

Inhibitors HA1077 (supplemented at 10 and 40 µM) and Aurothioglucose (at 10 µM) support the robust growth of hESC on cellulose microcarriers without Matrigel at passage 0 and 1 (FIG. 12). Cell numbers reach between 6 and 9 million/well which are equivalent to the control culture with Matrigel coating which achieved 8 million/well at passage 1. FIGS. 13 and 14 show stable expression of pluripotent markers Oct4 and mAb 84 of hESC cultures with inhibitors HA1077 and Aurothioglucose at passage 0 and 1 compared to the control with Matrigel coating. Finally, FIG. 15 shows pictures of confluent cultures of hESC on microcarriers with alternative ROCK inhibitors, Aurothioglucose and HA1077 (Fasudil).

Figure 19:
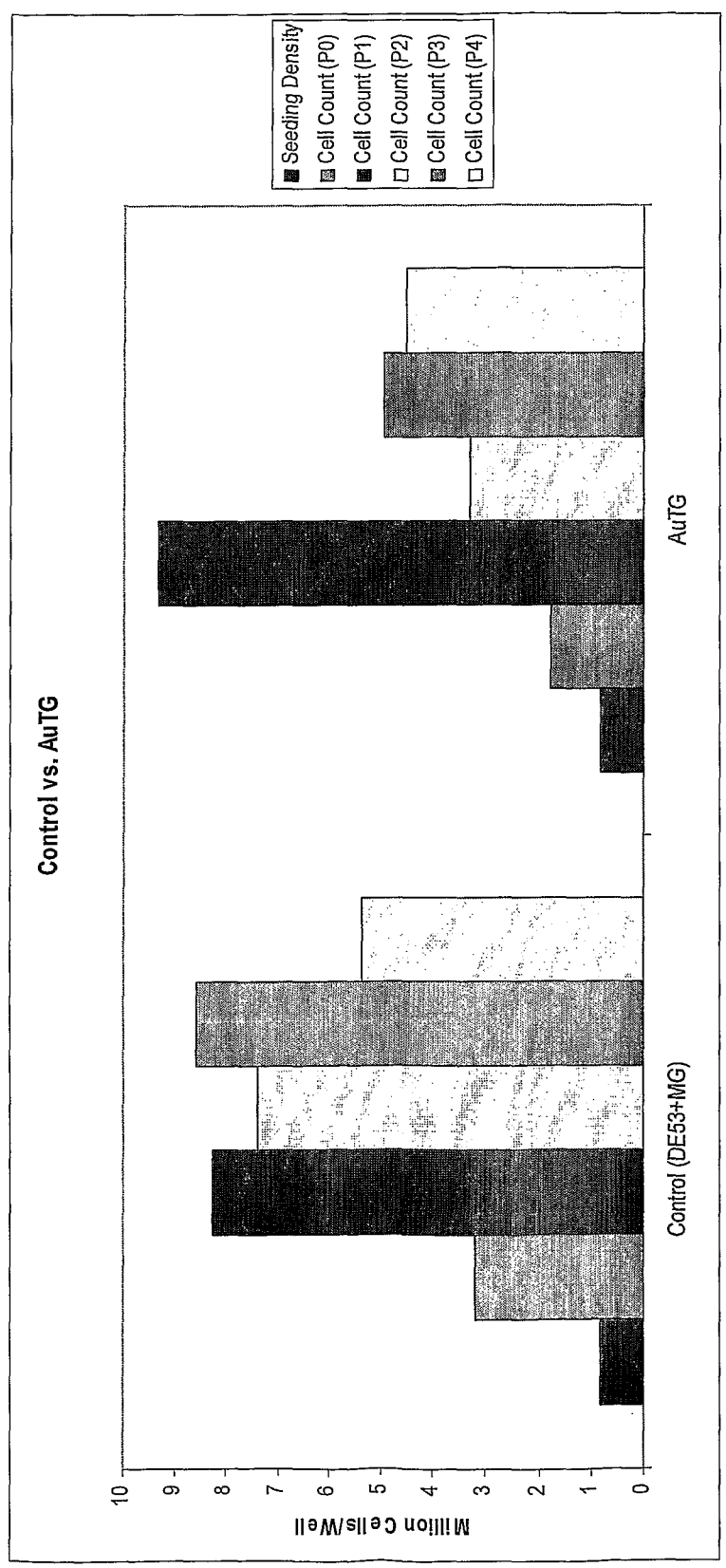
FIG. 19. Chart showing cell densities (million cells/well) of hESC on Matrigel coated cellulose DE53 microcarriers vs. uncoated microcarriers with the addition of Aurothioglucose from passage 0 to passage 4.
Figure 20:
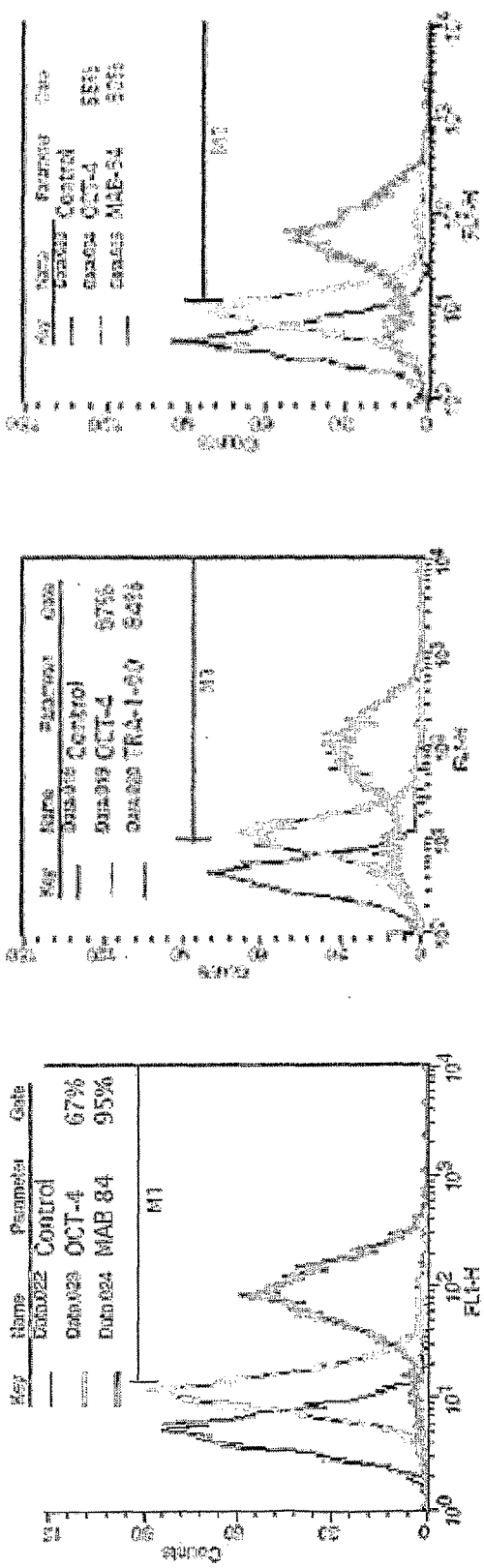
FIG. 20. FACS analysis. Expression of pluripotent markers Oct4 and mAb 84 of hESC cultures with Aurothioglucose at passages 1, 3 and 4.

To date, we have successfully passaged hESCs in the presence of Aurothioglucose through passage 4, with continued strong expression of pluripotency markers Oct4 and mAb84 (see FIGS. 19 and 20).

This data demonstrates that 5 types of microcarriers: cellulose DE53, QA52, Tosoh, Cytodex 1 and Cytodex 3, all uncoated are able to support hESC in long term culture with ROCK inhibitor Y-27632. Other inhibitors such as HA1077 (Fasudil) and Aurothioglucose are also capable of supporting hESC culture without Matrigel.

Example 6

A range of ROCK inhibitors (at 10 µM) were tested for their ability to allow hESC (HES-2) cell culture on matrix free cellulose DE53 microcarriers. These included fasudil, hydroxyfasudil and aurothioglucose and were compared to a control (DE53 microcarriers coated in Matrigel).

Figure 21A:
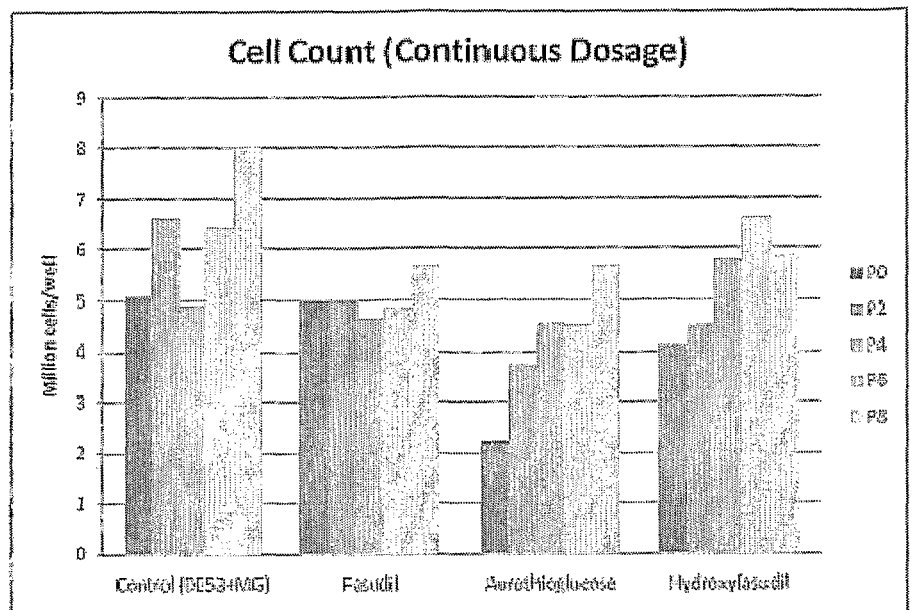
FIG. 21. Effect of daily continuous addition for 9 weeks of Fasudil, Hydroxyfasudil and Aurothioglucose on support of hESC cell expansion. (A) Chart showing effect of daily continuous addition for 9 weeks of Fasudil, Hydroxyfasudil and Aurothioglucose on support of hESC cell expansion to similar cell densities as control DE53 microcarriers. (B) Chart showing expression of pluripotent marker Tra-1-60 is about 80% for Fasudil and Hydroxyfasudil and 60% with Aurothioglucose after 9 weeks, compared to control of 90%. (C) Chart showing expression of pluripotent marker Oct4 is about 30-40% for Fasudil and Hydroxyfasudil and 50% with Aurothioglucose after 9 weeks, compared to control of 55%.
Figure 21B:
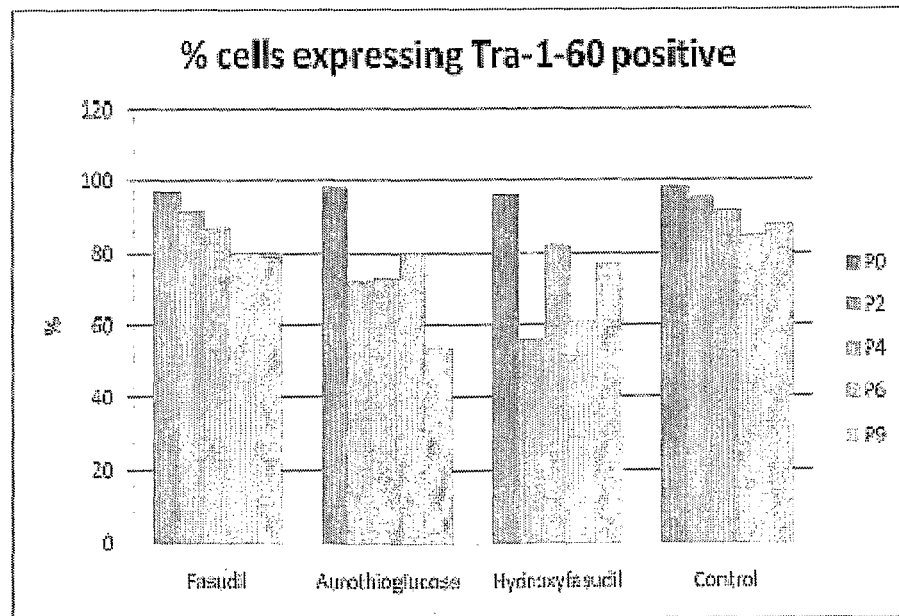
Figure 21C:
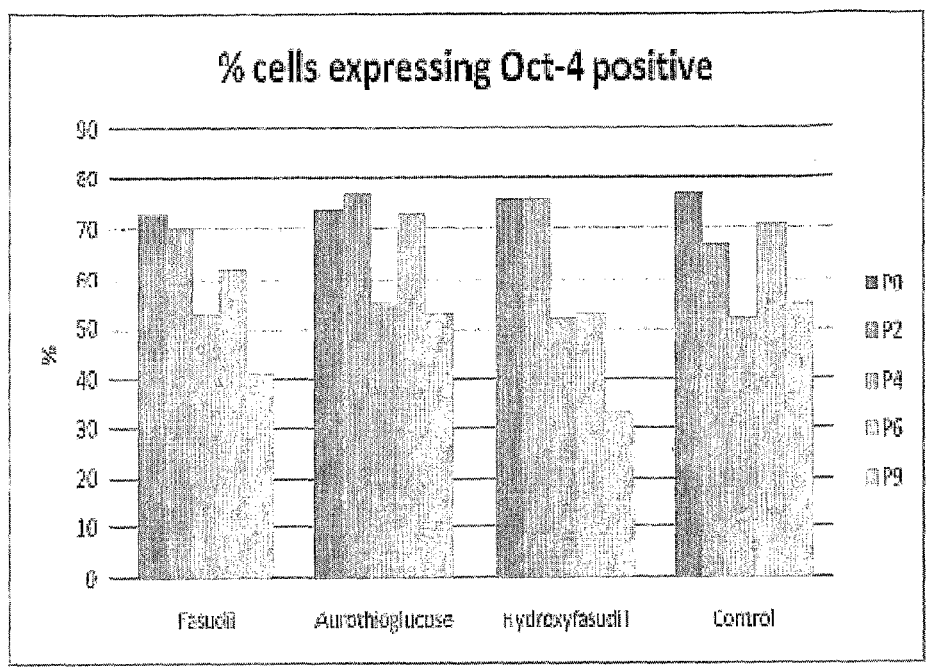
Figure 22:
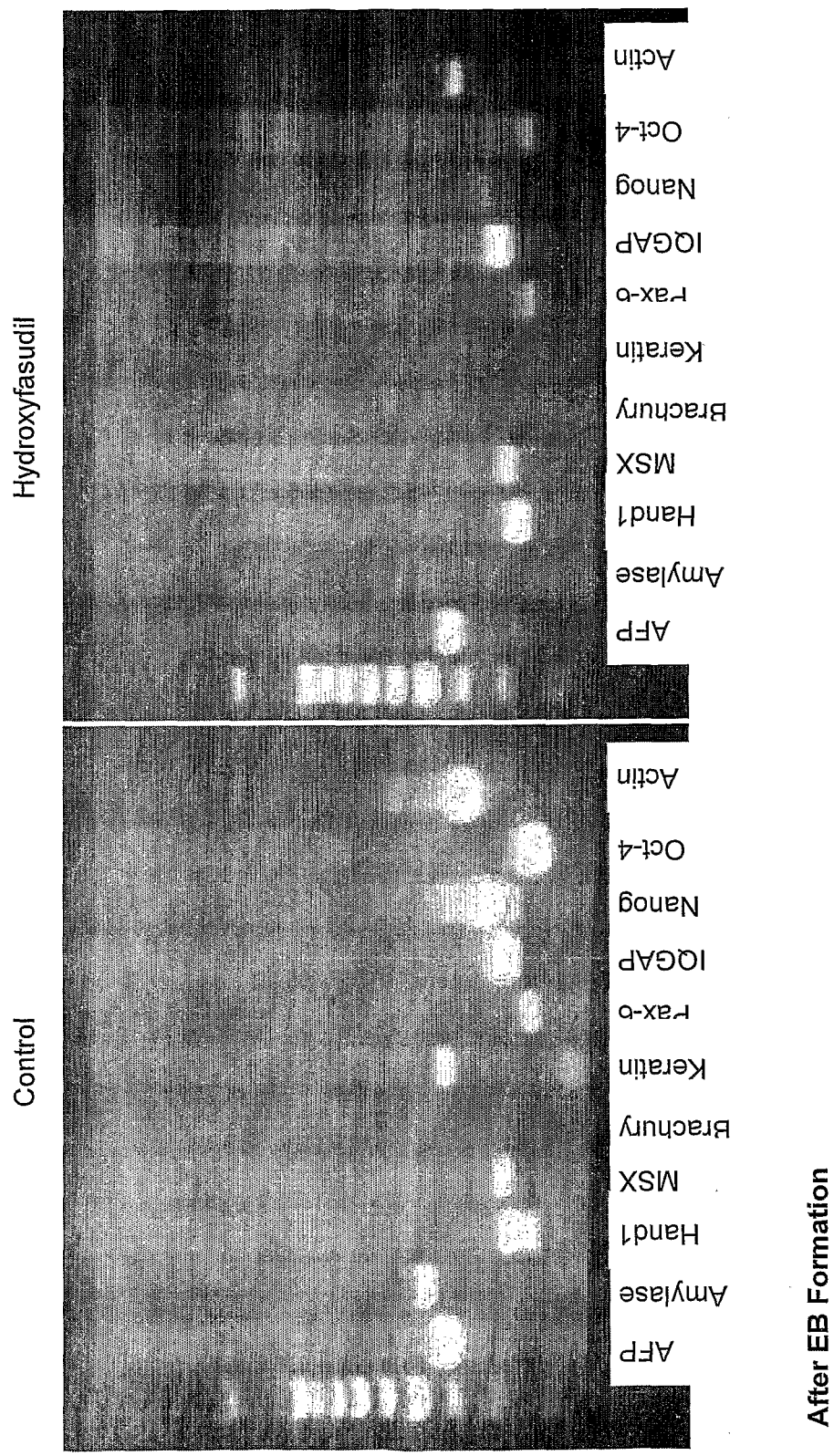
FIG. 22. Photographs showing results of gel electrophoresis for differentiation markers after embryoid body formation in control microcarriers vs. Hydroxyfasudil treated microcarrier cultured hESC. Includes expression of pluripotent genes Nanog & Oct4.
Figure 23:
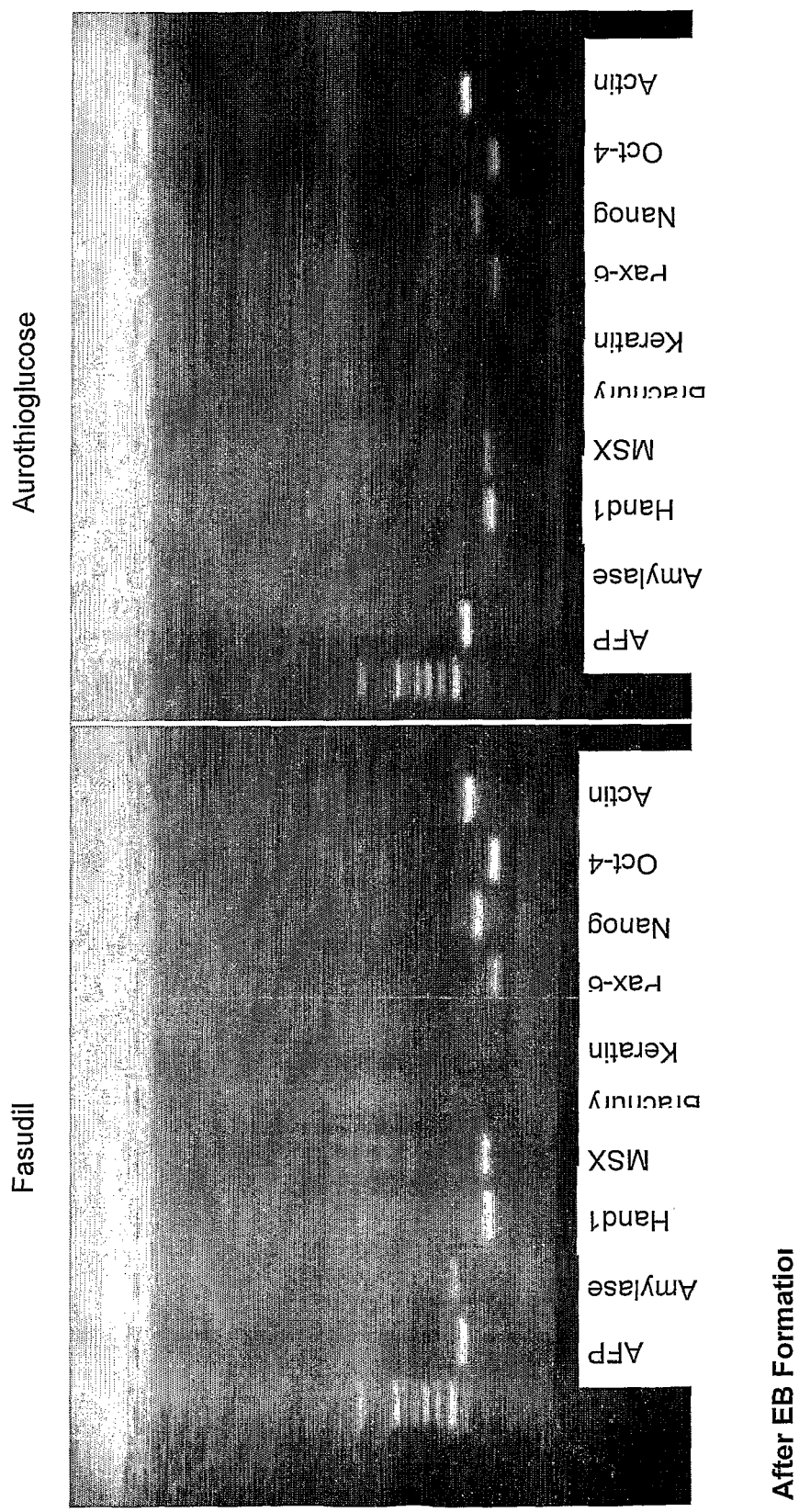
FIG. 23. Photographs showing results of gel electrophoresis for differentiation markers after embryoid body formation in Fasudil and Aurothioglucose treated microcarrier cultured hESC. Includes expression of pluripotent genes Nanog & Oct4.

Continuous addition of ROCK inhibitor was tested over 9 weeks (one passage per week), with results shown in FIGS. 21(A-C). Daily continuous addition for 9 weeks of Fasudil, Hydroxyfasudil and Aurothioglucose was able to support hESC cell expansion to similar cell densities as control DE53 microcarriers (FIG. 21A). Expression of the pluripotent marker Tra-1-60 was about 80% for Fasudil and Hydroxyfasudil and 60% with Aurothioglucose after 9 weeks, compared to control of 90% (FIG. 21B). Expression of pluripotent marker Oct4 was about 30-40% for Fasudil and Hydroxyfasudil and 50% with Aurothioglucose after 9 weeks, compared to control of 55% (FIG. 21C).

Figure 24A:
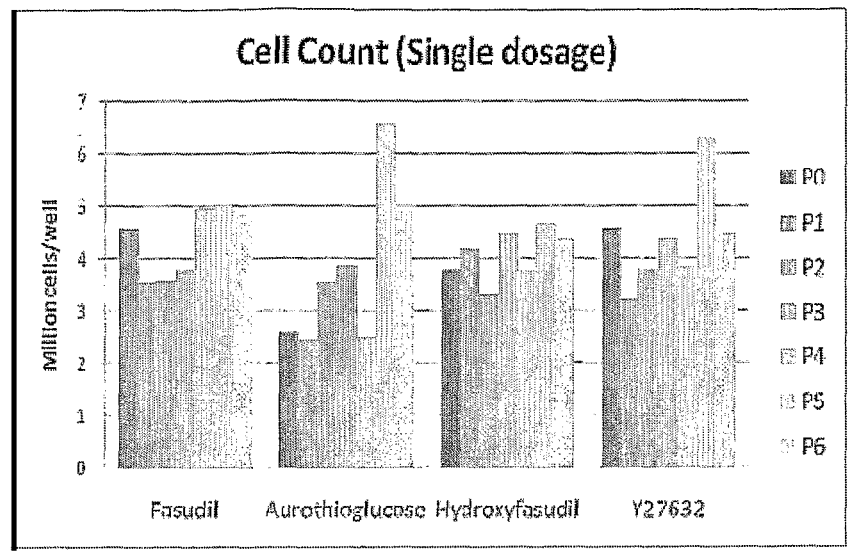
FIG. 24. (A) Chart showing that single dose addition (10 μM) for 6 weeks (one passage, P, per week) of Fasudil, Hydroxyfasudil, Aurothioglucose and Y27632 ROCK inhibitors are able to support hESC cell expansion to similar cell densities as control DE53 microcarriers (5 million/well). (B) Chart showing expression of pluripotent marker Tra-1-60 is about 80% for Fasudil and Y27632 ROCK inhibitor, 70% for Aurothioglucose and 50% with Hydroxyfasudil after 6 weeks (P6—one passage (P) per week).
Figure 24B:
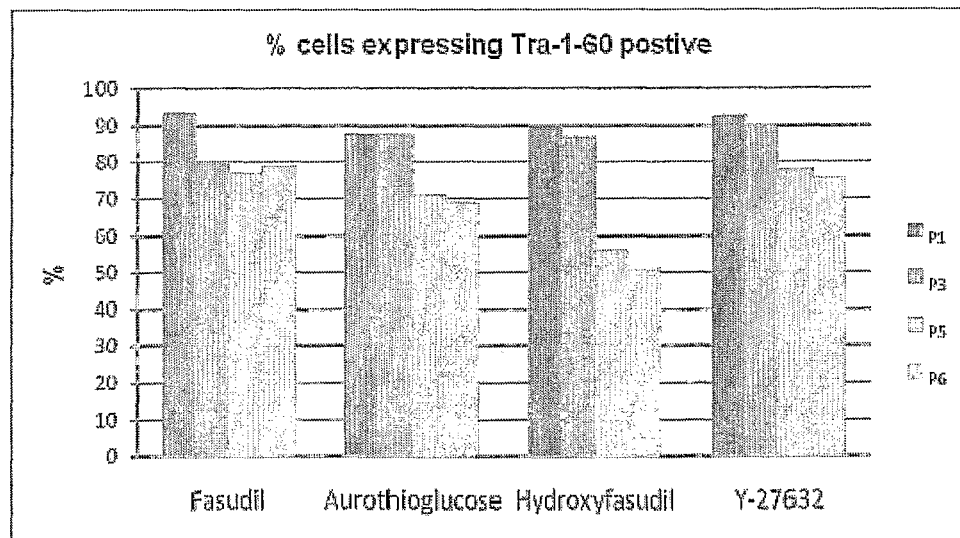
Figure 25:
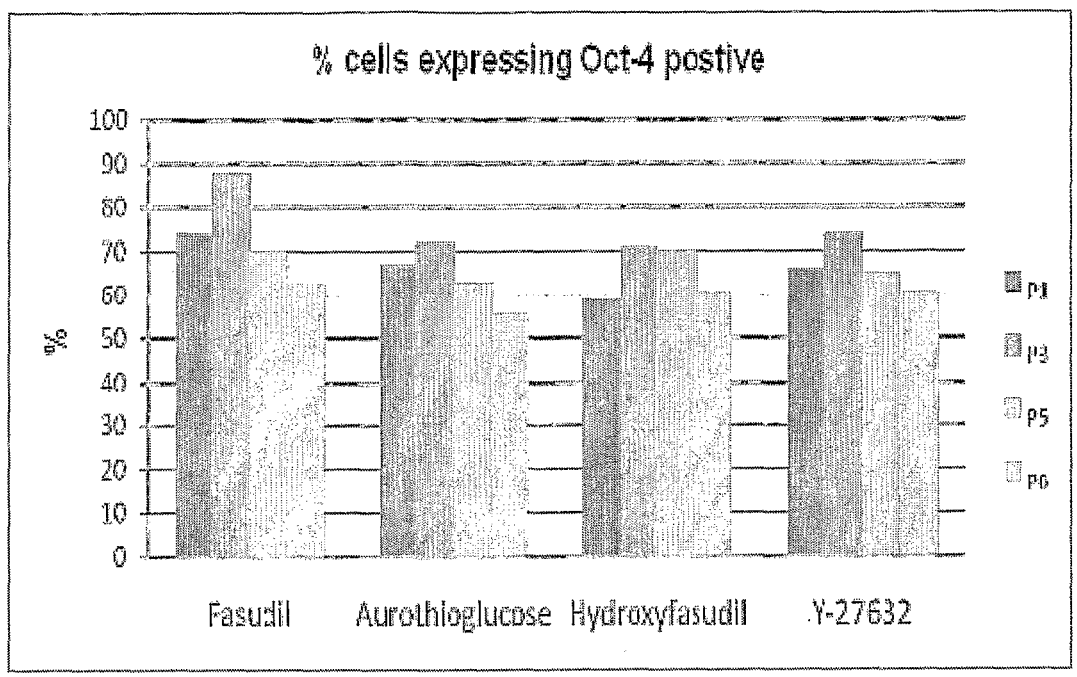
FIG. 25. Chart showing expression of pluripotent marker Oct4 is very similar for Fasudil and Hydroxyfasudil, Aurothioglucose and Y27632 ROCK inhibitor at 60% after 6 weeks (P6—one passage (P) per week).

Single dose addition for 6 weeks of Fasudil, Hydroxyfasudil, Aurothioglucose and Y27632 was able to support hESC (HES-2) cell expansion to similar cell densities as control DE53 microcarriers (5 million/well) (FIG. 24A). Expression of pluripotent marker Tra-1-60 was about 80% for Fasudil and Y27632, 70% for Aurothioglucose and 50% with Hydroxyfasudil after 6 weeks (FIG. 24B). Expression of pluripotent marker Oct4 was very similar for Fasudil and Hydroxyfasudil, Aurothioglucose and Y27632 ROCK inhibitor at 60% after 6 weeks (FIG. 25).

Example 7

Culture of IPS Cells with ROCK Inhibitor on Microcarriers

Figure 26:
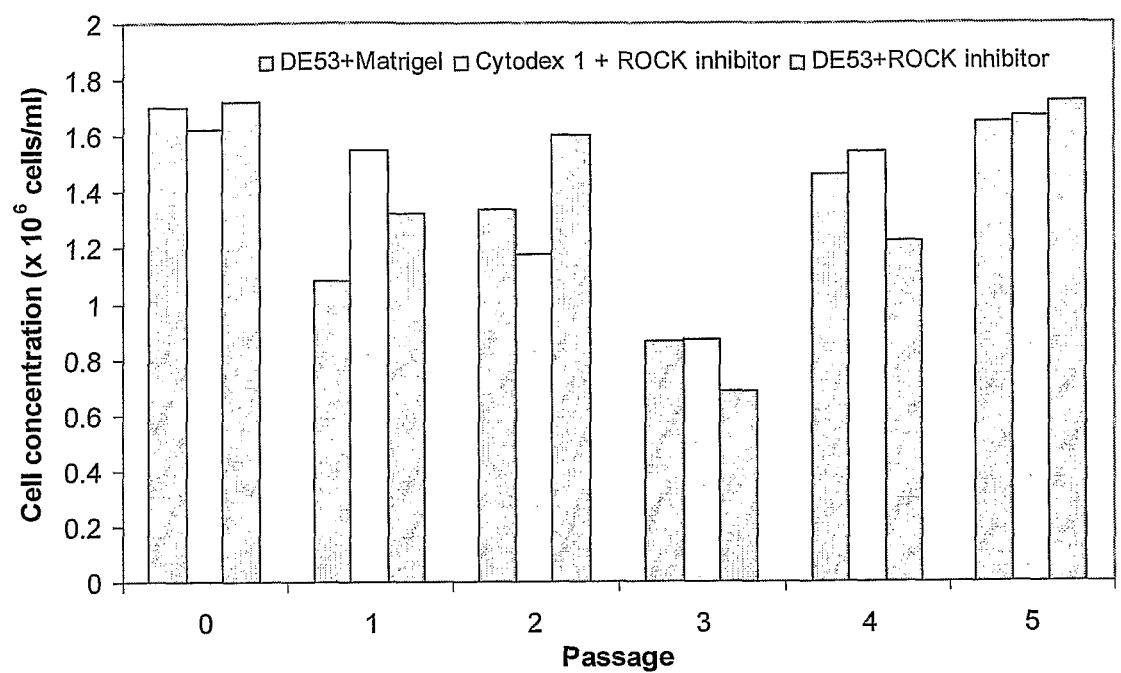
FIG. 26. Chart showing cells from the hESC cell line HES-2 (seeding density $0.8 \times 10^5$ cells/ml) cultured on Cytodex 1 (5 mg/well, 1 mg/ml) and DE53 (20 mg/well, 4 mg/ml) microcarriers with ROCK inhibitor (Y-27632 (10 μM)) have similar cell concentrations compared with as control (Matrigel) cultures.
Figure 27A:
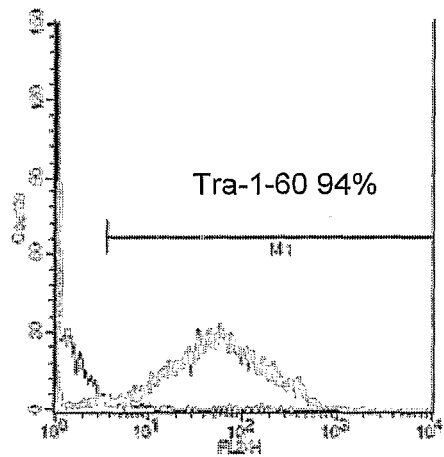
FIG. 27. Pluripotent marker expression (Tra-1-60) in cells from the hESC cell line HES-2 (seeding density $0.8 \times 10^5$ cells/ml) cultured on Cytodex 1 (5 mg/well, 1 mg/ml) and DE53 (20 mg/well, 4 mg/ml) microcarriers with ROCK inhibitor (Y-27632 (10 μM)) compared to control (Matrigel coated microcarriers) cultures. FACS Analysis showing expression of Tra-1-60 on (A) Cytodex 1 plus Y-27632 (10 μM) at passage 5 is ~94%, (B) DE53 plus Matrigel at passage 5 is ~88%, and (C) DE53 plus Y-27632 (10 μM) at passage 5 is ~92%.
Figure 27B:
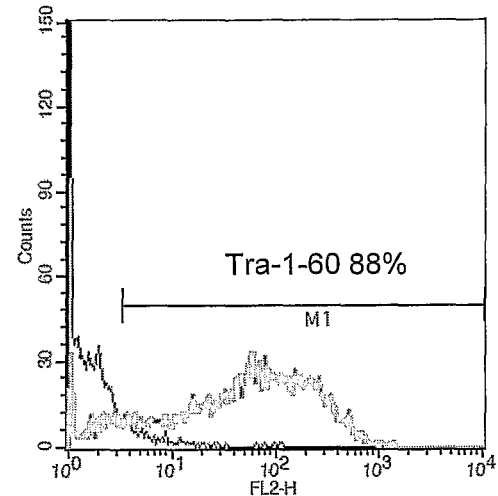
Figure 27C:
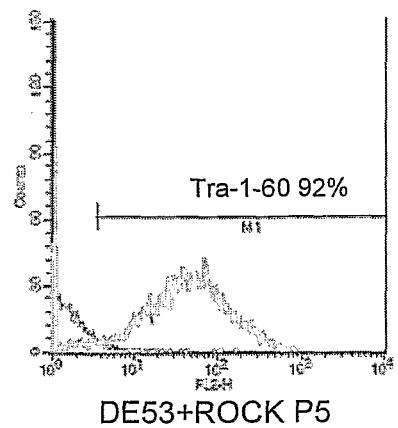

HES-2 cells cultured on Cytodex 1 and DE53 microcarriers with Y-27632 (10 μM) showed similar cell concentrations and pluripotent marker expression (Tra-1-60) as control cultures (Cytodex 1 or DE53 coated in Matrigel) (FIG. 26 and FIG. 27).

Example 8

Culture of iPS Cells with ROCK Inhibitor on Microcarriers iPS IMR90 cells (1.6×105 cells/ml) were cultured in wells of a 6-well plate with 20 mg of uncoated DE53, 5 ml of serum free media mTeSR1, 4 μl of ROCK inhibitor (Y27632) [10 μM]. 80% media refreshment and addition of inhibitor was carried out daily.

Figure 28:
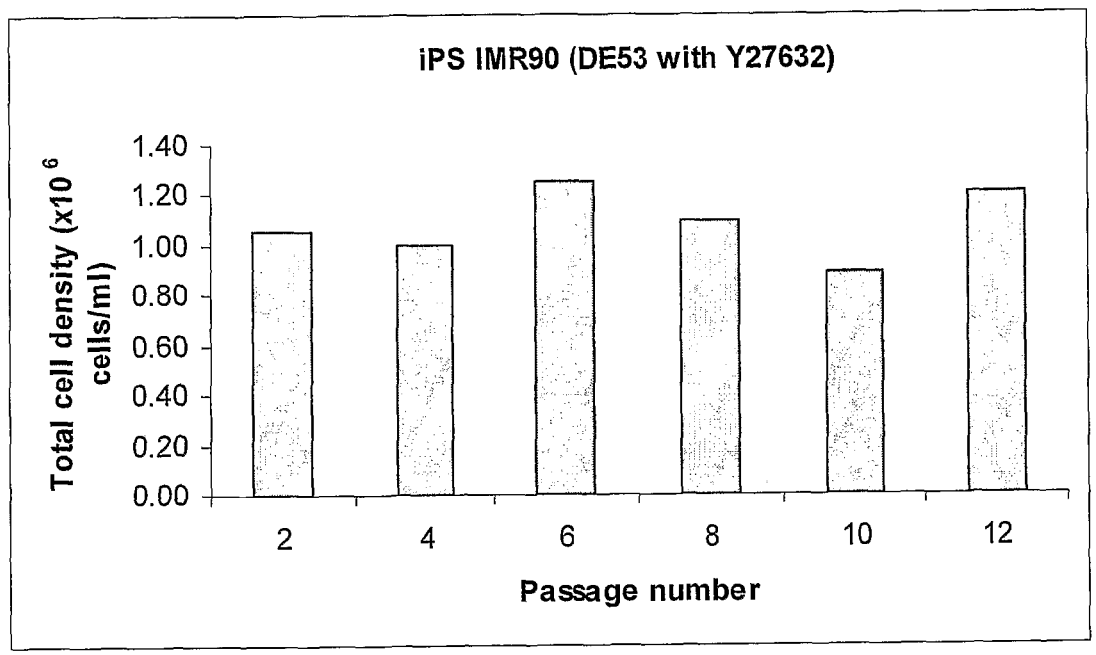
FIG. 28. Chart showing cell densities over 12 passages of human iPS cells (IMR90) cultured on DE53 microcarriers with Y-27632 (10 μM) in serum free media mTeSR1.
Figure 29A:
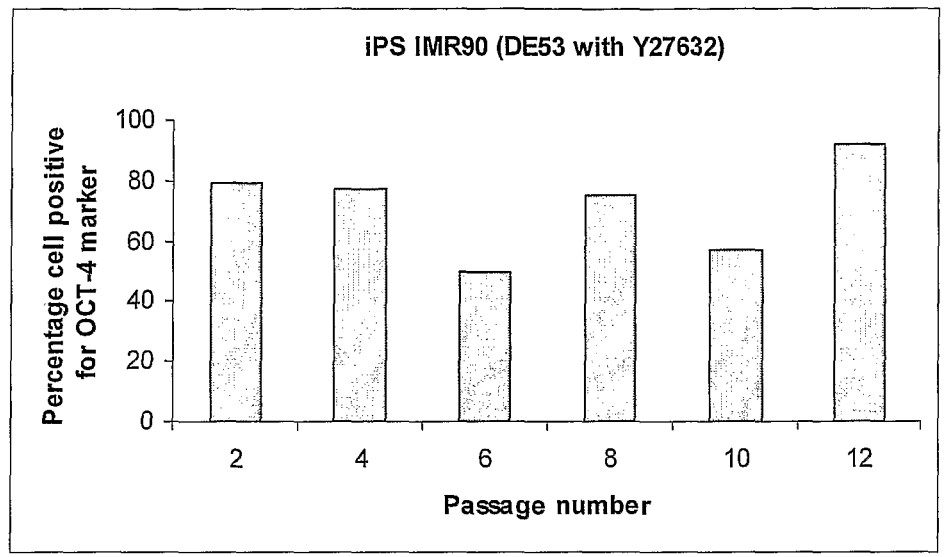
FIG. 29. Charts showing expression of pluripotent markers (A) Oct4 and (B) Tra-1-60 over 12 passages by human iPS cells (IMR90) cultured on DE53 microcarriers with Y-27632 (10 μM) in mTeSR1 media.
Figure 29B:
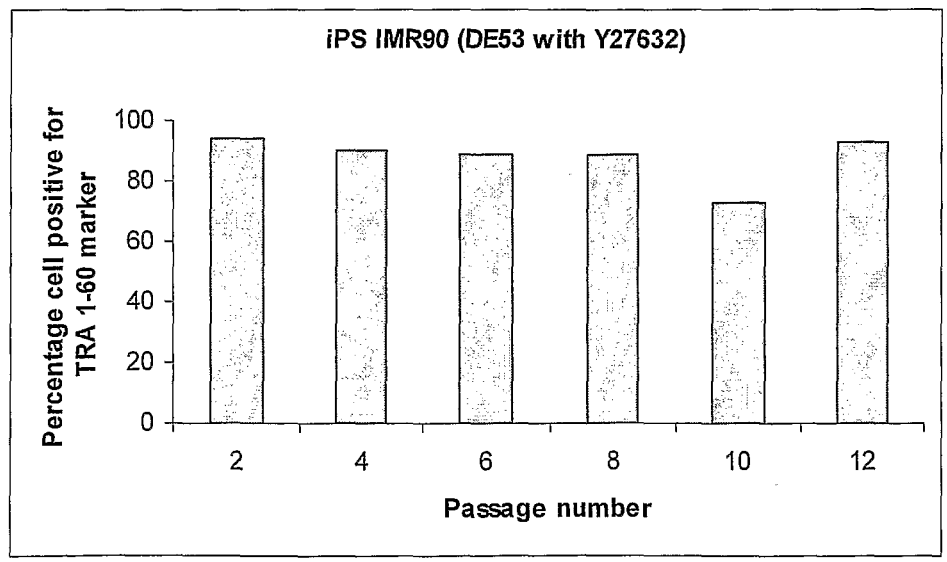
Figure 30A:
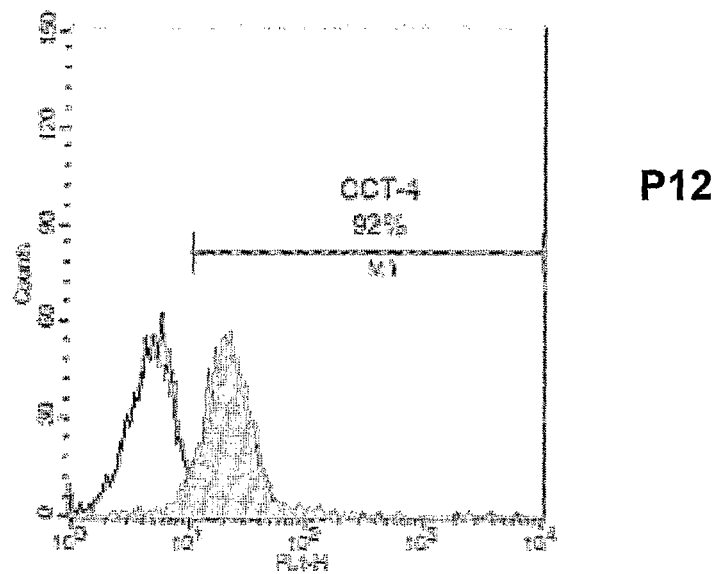
FIG. 30. FACS analysis at passage 12 of (A) Oct4 and (B) Tra-1-60 in human iPS cells (IMR90) cultured on DE53 microcarriers with Y-27632 (10 μM) in mTeSR1 media.
Figure 30B:
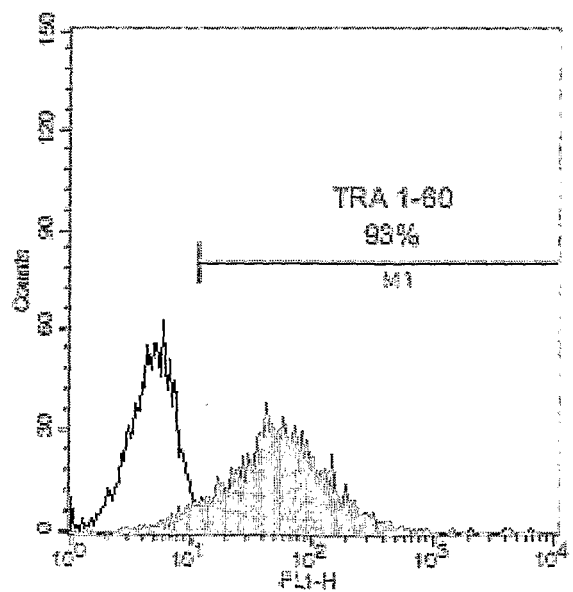

Cell density was stable over 12 passages (FIG. 28). Oct4 and Tra-1-60 expression was stable over 12 passages (FIG. 29 and FIG. 30).

Example 9

How Does ROCK Inhibitor Maintain hESC and hiPS Microcarrier Cultures in the Absence of Matrigel?

We demonstrated that 2 hESC (HES2 and HESS) and 2 human iPS (IMR90 and foreskin) cell lines can be maintained for greater than 10 weeks in the absence of Matrigel on a variety of microcarriers (DE53, Cytodex and Tosoh) while retaining their pluripotency.

Whilst examining this unusual phenomenon of long term culture of hESC with the ROCK inhibitor, we compared gene expression by microarray studies of ROCK inhibitor microcarrier culture without Matrigel vs. microcarrier cultures with Matrigel and conventional monolayer cultures with Matrigel and found that a common set of 141 genes were more than 2-fold differentially up- or down-regulated upon treatment with the ROCK inhibitor (results not shown).

A pathway-based analysis on the 162 pathways in the Panther database (http://www.pantherdb.org/) revealed 5 relevant pathways that were enriched with differentially expressed genes. Within these pathways, several genes associated with integrin/collagen synthesis, the FOX transcription factors and TGF-beta genes were upregulated, while a number of Cadherin genes were down-regulated.

REFERENCES

Chin, A. C. P., Fong, W. J., Goh, L. T., Philp, R., Oh, S. K., Choo, A. B., 2007. Identification of proteins from feeder conditioned medium that support human embryonic stem cells. J. Biotechnol. 130, 320-328.

Oh, S K W, Chen A K, Mok Y, Chen X, Lim U M, Chin A, Choo A B H, and Reuveny S. Long-term microcarrier suspension cultures of human embryonic stem cells. Stem Cell Research. 2: 219-230. 2009.

Each of the applications and patents mentioned in this document, and each document cited or referenced in each of the above applications and patents, including during the prosecution of each of the applications and patents ("application cited documents") and any manufacturer's instructions or catalogues for any products cited or mentioned in each of the applications and patents and in any of the application cited documents, are hereby incorporated herein by reference. Furthermore, all documents cited in this text, and all documents cited or referenced in documents cited in this text, and any manufacturer's instructions or catalogues for any products cited or mentioned in this text, are hereby incorporated herein by reference.

Various modifications and variations of the described methods and system of the invention will be apparent to those skilled in the art without departing from the scope and spirit of the invention. Although the invention has been described in connection with specific preferred embodiments, it should be understood that the invention as claimed should not be unduly limited to such specific embodiments and that many modifications and additions thereto may be made within the scope of the invention. Indeed, various modifications of the described modes for carrying out the invention which are obvious to those skilled in molecular biology or related fields are intended to be within the scope of the claims. Furthermore, various combinations of the features of the following dependent claims can be made with the features of the independent claims without departing from the scope of the present invention.

The invention claimed is:

1. A method of culturing human pluripotent cells in vitro, the method comprising:
   (i) attaching human pluripotent cells to a plurality of uncoated microcarriers to form microcarrier-cell complexes, and
   (ii) culturing the microcarrier-cell complexes in suspension culture in the presence of a ROCK inhibitor;
   (iii) passaging the cultured cells from (ii), wherein cells after passaging are pluripotent, and
   (iv) repeating steps (i)-(iii) through at least 7 passages; wherein human pluripotent cells are expanded between each passage; and whereby stable, long-term culture and expansion of human pluripotent cells is achieved in suspension in vitro.

2. The method of claim 1 wherein the ROCK inhibitor is chosen from: Y-27632, HA-1077 (Fasudil), HA-1100 (HydroxyFasudil), H-1152, 3-(4-Pyridyl)-1H-indole, N-(4-Pyridyl)-N'-(2,4,6-trichlorophenyl) urea, Aurothioglucose, LY294002 or a salt, base, ester or prodrug thereof.

3. The method of claim 1 wherein the cells are stem cells, embryonic stem cells or induced pluripotent stem cells.

4. The method of claim 1 wherein all or a substantial portion of cells in the culture after step (iv) retain a normal karyotype, preferably wherein said substantial portion is 70% or more.

5. The method of claim 1 wherein in step (iv), steps (i)-(iii) are repeated through at least 9 passages.

6. The method of claim 1 wherein the microcarriers comprise or consist of one or more of cellulose, dextran, hydroxylated methacrylate, collagen, gelatin, polystyrene, plastic, glass, ceramic, or silicone.

7. The method of claim 1 wherein the microcarriers are macroporous or microporous carboseed microcarriers.

8. The method of claim 1 wherein the microcarriers are coupled with protamine or polylysine.

9. The method of claim 1 wherein the microcarriers are positively charged, preferably having a positive surface charge.

10. The method of claim 1 wherein the microcarriers are hydrophilic.

11. The method of claim 1 wherein the microcarriers are rod-shaped or have a substantially spherical shape.

12. The method of claim 1 wherein in step (ii) the cells are cultured for a period of time sufficient to expand the number of cells in the culture.

13. The method of claim 1 wherein after step (iv) at least 60% of the cells in the culture are pluripotent or at least 60% of the cells in the culture express one, two, three or all of Oct4, SSEA4, TRA-1-60 and Mab84.

14. The method of claim 1 wherein the method comprises culturing the cells in serum free media, or stem cell conditioned media, or feeder cell free conditions, optionally where feeder cells are also attached to the microcarriers.

15. The method of claim 1 wherein the culture further comprises feeder cells attached to microcarriers which are different from the microcarriers to which the pluripotent cells are attached.

16. A method of propagating human pluripotent cells comprising the steps of:
  (a) providing an uncoated microcarrier;
  (b) allowing a human pluripotent cell to attach to the uncoated microcarrier; and
  (c) aggregating microcarriers with human pluripotent cells attached thereon to thereby propagate the human pluripotent cells,
  wherein in one or more, or all, of steps (a), (b) or (c) the microcarrier and/or cells are contacted with a ROCK Inhibitor.

17. The method of claim 1 wherein in step (iv), steps (i)-(iii) are repeated through at least 15 passages.

18. The method of claim 1 wherein in step (iv), steps (i)-(iii) are repeated through at least 30 passages.

* * * * *